United States Patent
Barbash et al.

(10) Patent No.: US 11,197,857 B2
(45) Date of Patent: Dec. 14, 2021

(54) COMBINATION THERAPY

(71) Applicant: GlaxoSmithKline Intellectual Property Development Limited, Middlesex (GB)

(72) Inventors: Olena I. Barbash, Collegeville, PA (US); Andy Fedoriw, Collegeville, PA (US); Sarah Gerhart, Collegeville, PA (US); Ryan G. Kruger, Collegeville, PA (US); Jenny Laraio, Collegeville, PA (US); Helai Mohammad, Collegeville, PA (US); Shane W. Obrien, Collegeville, PA (US); Jacob Rubin, Collegeville, PA (US); Niyant Shah, Collegeville, PA (US); Ping Zhang, Collegeville, PA (US)

(73) Assignee: GlaxoSmithKline Intellectual Property Development Limited, Middlesex (GB)

( * ) Notice: Subject to any disclaimer, the term of this patent is extended or adjusted under 35 U.S.C. 154(b) by 212 days.

(21) Appl. No.: 16/464,439

(22) PCT Filed: Nov. 30, 2017

(86) PCT No.: PCT/IB2017/057546
§ 371 (c)(1),
(2) Date: May 28, 2019

(87) PCT Pub. No.: WO2018/100532
PCT Pub. Date: Jun. 7, 2018

(65) Prior Publication Data
US 2021/0106580 A1 Apr. 15, 2021

Related U.S. Application Data

(60) Provisional application No. 62/428,751, filed on Dec. 1, 2016.

(51) Int. Cl.
*A61K 31/415* (2006.01)
*A61K 31/506* (2006.01)
*A61P 35/04* (2006.01)

(52) U.S. Cl.
CPC .......... *A61K 31/506* (2013.01); *A61K 31/415* (2013.01); *A61P 35/04* (2018.01)

(58) Field of Classification Search
CPC . A61K 31/415; A61K 31/4725; A61K 31/506
See application file for complete search history.

(56) References Cited

FOREIGN PATENT DOCUMENTS

| WO | WO 2014/100719 A2 | 6/2014 |
| WO | WO 2014/153226 A1 | 9/2014 |

OTHER PUBLICATIONS

Zheng, et al., "Arginine Methylation-Dependent Reader-Writer Interplay Governs Growth Control by E2F-1", *Molecular Cell*, 52(1):37-51 (2013).

*Primary Examiner* — Deepak R Rao
(74) *Attorney, Agent, or Firm* — Robert H. Brink; Scott Young; Duke M. Fitch

(57) ABSTRACT

The present invention provides a combination of a Type I protein arginine methyltransferase (Type I PRMT) inhibitor and a Type II protein arginine methyltransferase (Type II PRMT) inhibitor. The present invention also provides methods for treating cancer in a human in need thereof, the methods comprising administering to the human a combination of a Type I PRMT inhibitor and a Type II PRMT inhibitor, together with at least one of: a pharmaceutically acceptable carrier and a pharmaceutically acceptable diluent, thereby treating the cancer in the human. The present invention further provide a pharmaceutical composition comprising a therapeutically effective amount of a Type I PRMT inhibitor and a second pharmaceutical composition comprising a therapeutically effective amount of a Type II PRMT inhibitor.

7 Claims, 46 Drawing Sheets

FIG. 4
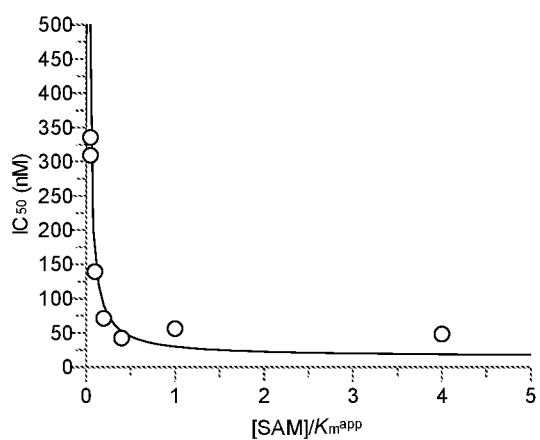
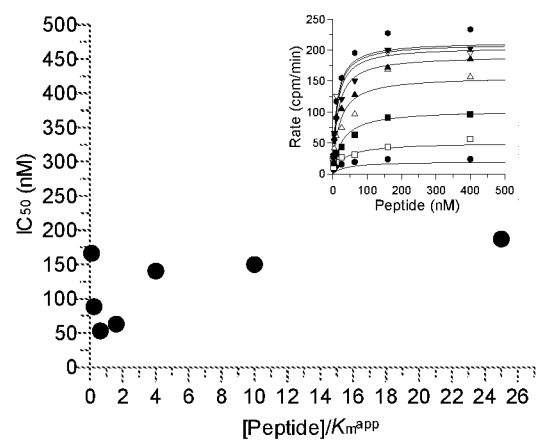

FIG. 7
A.
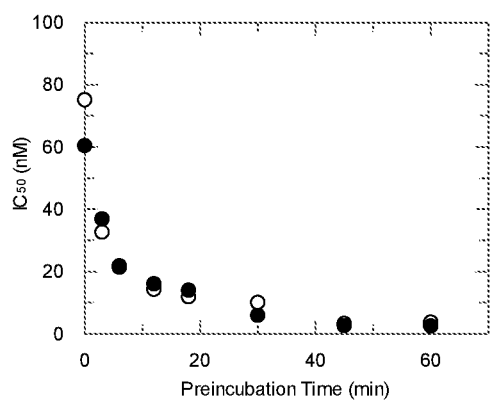
B.
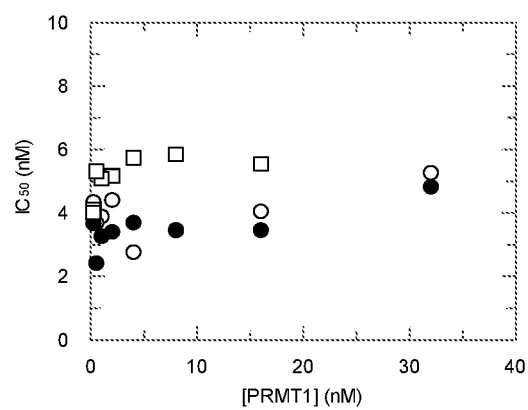
C.
| Species | IC$_{50}$ (nM) | Std Err | n | $K_i^{*app}$ (nM) |
|---|---|---|---|---|
| Human | 3.1 | 0.4 | 29 | 1.5 |
| Dog | 2.3 | 0.4 | 8 | 1.2 |
| Rat | 2.2 | 0.4 | 8 | 1.1 |

A.

| Type | Enzyme | IC$_{50}$ (nM) | Std Err | n | $K_i^{*app}$ (nM) | Fold |
|---|---|---|---|---|---|---|
| I | PRMT1 | 3.1 | 0.4 | 29 | 1.5 | 1 |
| I | PRMT3 | 162 | 18 | 8 | | 52 |
| I | PRMT4 | 38 | 5.3 | 9 | 19 | 12 |
| I | PRMT6 | 4.7 | 0.6 | 10 | 2.4 | 1.5 |
| I | PRMT8 | 3.9 | 0.4 | 10 | 2.0 | 1.3 |
| II | PRMT5/MEP50 | >20408 | | 2 | | >6500 |
| II | PRMT9 | >20408 | | 2 | | >6500 |

B.

FIG. 18
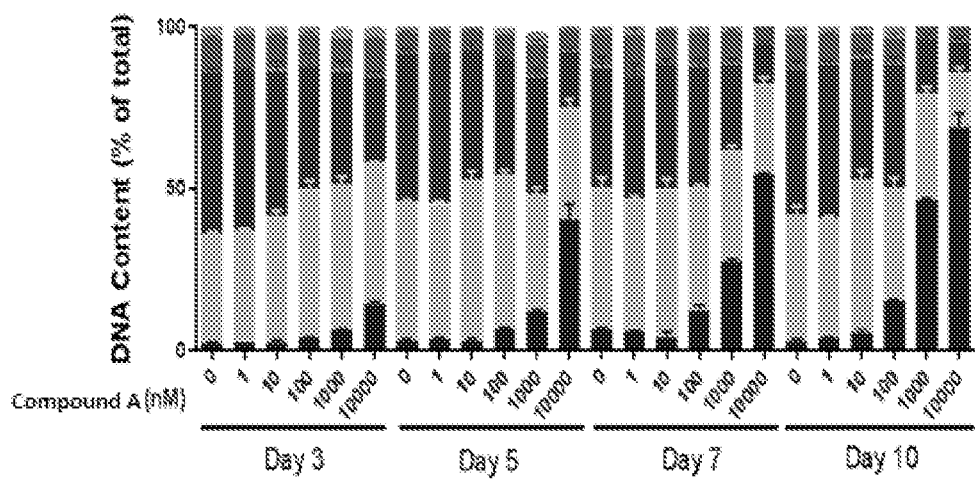
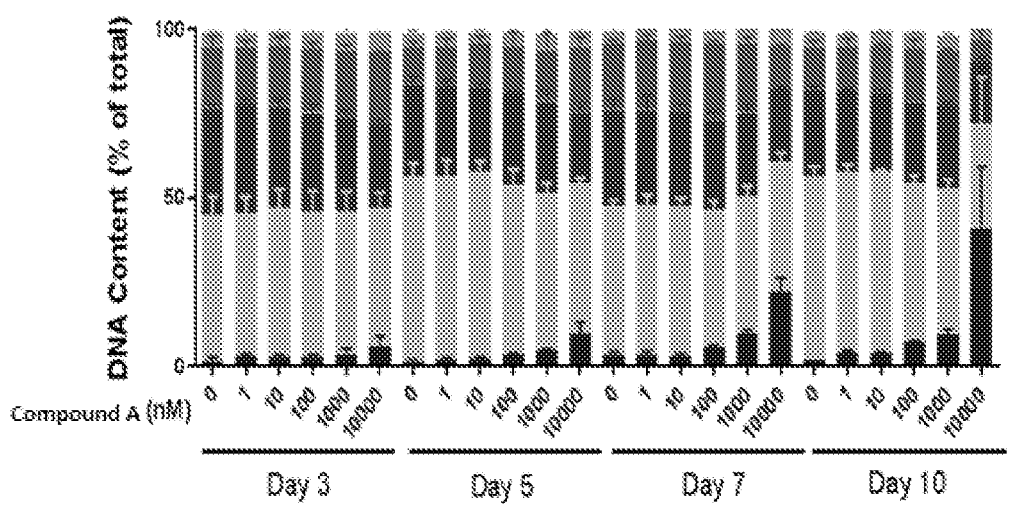

FIG. 22
A
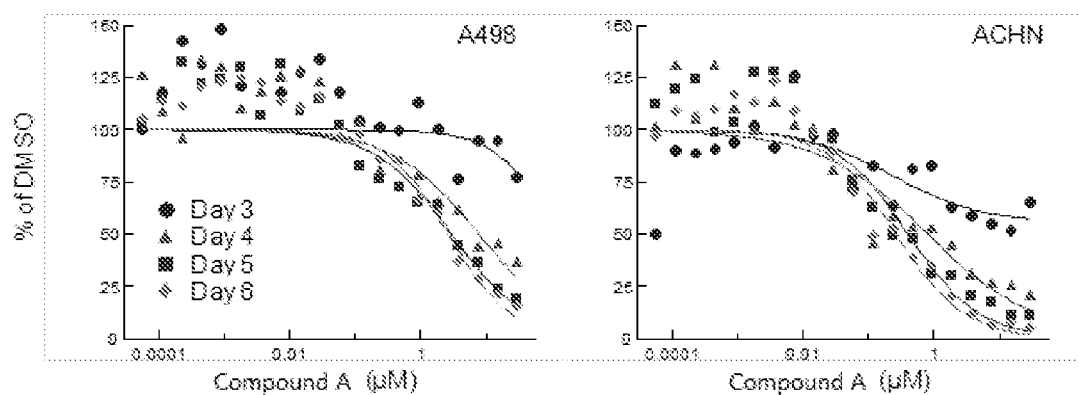
B
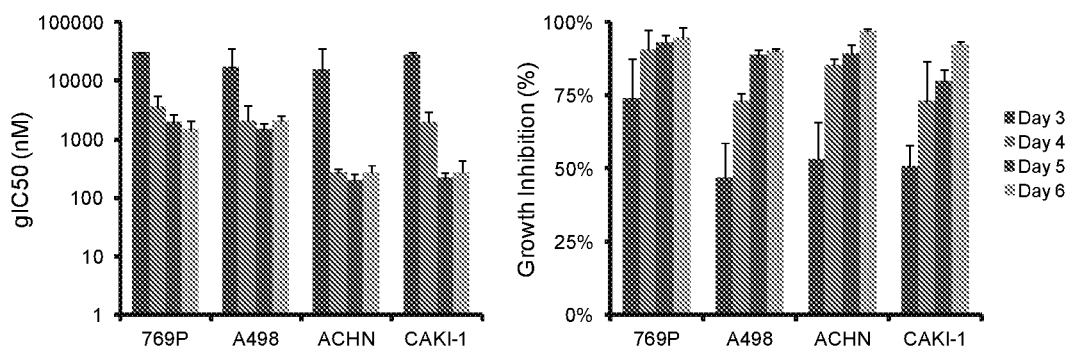

The multiple salt forms of Compound C used in the studies reported in this document (free base, HCl and succinate) had equivalent biochemical activity and are therefore not further identified.

FIG. 54

| gIC50 fold change | BT-20 | BT-549 | DU-4475 | HCC1937 | HCC70 | Hs-578T | MDA-MB-468 |
|---|---|---|---|---|---|---|---|
| CARBOPLATIN | 1.7 | 0.8 | 2.1 | 0.7 | 0.9 | 2.1 | 1.0 |
| CISPLATIN | 1.7 | 0.8 | 2.0 | 0.6 | 1.3 | 1.5 | 0.6 |
| DOXORUBICIN | 1.5 | 0.9 | 0.8 | 2.0 | 1.5 | 1.4 | 0.8 |
| BET inhibitor | 2.2 | 1.1 | 1.6 | 0.3 | 1.1 | 1.0 | 1.6 |
| MEK inhibitor | 2.5 | 0.8 | 0.5 | 1.3 | 1.3 | 1.5 | 1.6 |
| Compound D | 6.4 | 11.9 | 8.2 | 2.4 | 3.1 | 8.8 | 4.4 |

| gIC100 fold change | BT-20 | BT-549 | DU-4475 | HCC1937 | HCC70 | Hs-578T | MDA-MB-468 |
|---|---|---|---|---|---|---|---|
| CARBOPLATIN | 2.2 | 1.0 | 3.9 | 1.4 | 2.9 | 1.0 | 2.4 |
| CISPLATIN | 0.6 | 1.0 | 1.6 | 0.9 | 1.1 | 1.0 | 1.3 |
| DOXORUBICIN | 1.2 | 1.0 | 1.1 | 1.8 | 1.3 | 6.1 | 1.4 |
| BET inhibitor | 1.0 | 1.0 | 1.8 | 1.0 | 3.1 | 0.9 | 11.7 |
| MEK inhibitor | 1.0 | 1.0 | 0.6 | 1.0 | 1.6 | 1.0 | 1.1 |
| Compound D | 6.2 | 1.0 | 1.0 | 5.2 | 3.9 | 1.0 | 10.0 |

| FC ≥ 5 | 3 ≤ FC < 5 | FC < 3 |

FIG. 55

| gIC50 fold change | 5637 | 639-V | 647-V | BC-3C | BFTC-905 | CAL-29 | JMSU-1 | ScaBER | SW-780 | T24 |
|---|---|---|---|---|---|---|---|---|---|---|
| CARBOPLATIN | 1.3 | 1.5 | 1.1 | 1.0 | 0.7 | 0.8 | 0.5 | 0.8 | 1.1 | 1.0 |
| CISPLATIN | 1.0 | 1.1 | 1.2 | 1.0 | 0.7 | 0.7 | 0.6 | 0.9 | 0.8 | 0.7 |
| DOXORUBICIN | 1.0 | 1.6 | 1.7 | 1.8 | 1.5 | 1.3 | 1.9 | 1.8 | 1.7 | 1.4 |
| BET inhibitor | 0.3 | 3.0 | 2.0 | 0.7 | 1.5 | 1.9 | 0.8 | 0.8 | 0.8 | 1.0 |
| MEK inhibitor | 1.2 | 1.4 | 1.4 | 2.7 | 0.7 | 1.3 | 1.2 | 1.1 | 0.3 | 0.2 |
| Compound D | 2.0 | 4.6 | 5.5 | 4.7 | 4.0 | 6.5 | 13.3 | 3.8 | 2.0 | 3.5 |

| gIC100 fold change | 5637 | 639-V | 647-V | BC-3C | BFTC-905 | CAL-29 | JMSU-1 | ScaBER | SW-780 | T24 |
|---|---|---|---|---|---|---|---|---|---|---|
| CARBOPLATIN | 0.9 | 2.7 | 1.6 | 1.0 | 1.2 | 1.7 | 1.0 | 0.6 | 1.0 | 1.0 |
| CISPLATIN | 0.2 | 0.7 | 1.0 | 1.0 | 1.0 | 1.1 | 1.0 | 0.8 | 1.0 | 1.0 |
| DOXORUBICIN | 6.5 | 1.9 | 1.3 | 1.0 | 1.2 | 1.2 | 0.7 | 1.8 | 2.3 | 3.5 |
| BET inhibitor | 0.3 | 1.0 | 0.6 | 1.0 | 1.0 | 1.0 | 1.0 | 1.0 | 1.0 | 1.0 |
| MEK inhibitor | 2.5 | 1.0 | 1.0 | 1.0 | 0.9 | 1.0 | 1.1 | 0.4 | 1.0 | 1.0 |
| Compound D | 5.9 | 1.0 | 10.2 | 1.0 | 3.5 | 3.1 | 11.3 | 16.1 | 1.9 | 1.0 |

| FC ≥ 5 | 3 ≤ FC < 5 | FC < 3 |

|  | Ymin-T0 % | |
|---|---|---|
|  | SW-780 | T24 |
| Compound B | 151 | 666 |
| Compound D | 864 | 1586 |
| combo | -4 | 24 |

FIG. 58

| Compound B/Compound D (PRMT5/PRMT1) | | | | |
|---|---|---|---|---|
| Ymin-T0 % Change | 100% (loaded) / <100% (toxic) | 50%<...100% (static) / 50%<...100% (toxic) | 0<-50% (static) / 0<-50% (toxic) | >0 |
| Bladder % (total 10) | 30 / 50 | | 10 | 10 |
| TNBC % (total 7) | 43 / 29 | 14 | 14 | |

COMBINATION THERAPY

This application is a 371 of International Application No. PCT/162017/057546, filed 30 Nov. 2017, which claims priority to U.S. 62/428,751 filed 1 Dec. 2016.

FIELD OF THE INVENTION

The present invention relates to a method of treating cancer in a mammal and to combinations useful in such treatment. In particular, the present invention relates to combinations of Type I protein arginine methyltransferase (Type I PRMT) inhibitors and Type II protein arginine methyltransferase (Type II PRMT) inhibitors.

BACKGROUND OF THE INVENTION

Effective treatment of hyperproliferative disorders, including cancer, is a continuing goal in the oncology field. Generally, cancer results from the deregulation of the normal processes that control cell division, differentiation and apoptotic cell death and is characterized by the proliferation of malignant cells which have the potential for unlimited growth, local expansion and systemic metastasis. Deregulation of normal processes includes abnormalities in signal transduction pathways and response to factors that differ from those found in normal cells.

Arginine methylation is an important post-translational modification on proteins involved in a diverse range of cellular processes such as gene regulation, RNA processing, DNA damage response, and signal transduction. Proteins containing methylated arginines are present in both nuclear and cytosolic fractions suggesting that the enzymes that catalyze the transfer of methyl groups on to arginines are also present throughout these subcellular compartments (reviewed in Yang, Y. & Bedford, M. T. Protein arginine methyltransferases and cancer. *Nat Rev Cancer* 13, 37-50, doi:10.1038/nrc3409 (2013); Lee, Y. H. & Stallcup, M. R. Minireview: protein arginine methylation of nonhistone proteins in transcriptional regulation. *Mol Endocrinol* 23, 425-433, doi:10.1210/me.2008-0380 (2009)). In mammalian cells, methylated arginine exists in three major forms: ω—$N^G$-monomethyl-arginine (MMA), ω—$N^G,N^G$-asymmetric dimethyl arginine (ADMA), or ω—$N^G,'N^G$-symmetric dimethyl arginine (SDMA). Each methylation state can affect protein-protein interactions in different ways and therefore has the potential to confer distinct functional consequences for the biological activity of the substrate (Yang, Y. & Bedford, M. T. Protein arginine methyltransferases and cancer. *Nat Rev Cancer* 13, 37-50, doi:10.1038/nrc3409 (2013)).

Arginine methylation occurs largely in the context of glycine-, arginine-rich (GAR) motifs through the activity of a family of Protein Arginine Methyltransferases (PRMTs) that transfer the methyl group from S-adenosyl-L-methionine (SAM) to the substrate arginine side chain producing S-adenosyl-homocysteine (SAH) and methylated arginine. This family of proteins is comprised of 10 members of which 9 have been shown to have enzymatic activity (Bedford, M. T. & Clarke, S. G. Protein arginine methylation in mammals: who, what, and why. *Mol Cell* 33, 1-13, doi: 10.1016/j.molcel.2008.12.013 (2009)). The PRMT family is categorized into four sub-types (Type I-IV) depending on the product of the enzymatic reaction. Type IV enzymes methylate the internal guanidino nitrogen and have only been described in yeast (Fisk, J. C. & Read, L. K. Protein arginine methylation in parasitic protozoa. Eukaryot Cell 10, 1013-1022, doi:10.1128/EC.05103-11 (2011)); types I-III enzymes generate monomethyl-arginine (MMA, Rme1) through a single methylation event. The MMA intermediate is considered a relatively low abundance intermediate, however, select substrates of the primarily Type III activity of PRMT7 can remain monomethylated, while Types I and II enzymes catalyze progression from MMA to either asymmetric dimethyl-arginine (ADMA, Rme2a) or symmetric dimethyl arginine (SDMA, Rme2s) respectively. Type II PRMTs include PRMT5, and PRMT9, however, PRMT5 is the primary enzyme responsible for formation of symmetric dimethylation. Type I enzymes include PRMT1, PRMT3, PRMT4, PRMT6 and PRMT8. PRMT1, PRMT3, PRMT4, and PRMT6 are ubiquitously expressed while PRMT8 is largely restricted to the brain (reviewed in Bedford, M. T. & Clarke, S. G. Protein arginine methylation in mammals: who, what, and why. Mol Cell 33, 1-13, doi:10.1016/j.molcel.2008.12.013 (2009)).

Mis-regulation and overexpression of PRMT1 has been associated with a number of solid and hematopoietic cancers (Yang, Y. & Bedford, M. T. Protein arginine methyltransferases and cancer. *Nat Rev Cancer* 13, 37-50, doi:10.1038/nrc3409 (2013); Yoshimatsu, M. et al. Dysregulation of PRMT1 and PRMT6, Type I arginine methyltransferases, is involved in various types of human cancers. *Int J Cancer* 128, 562-573, doi:10.1002/ijc.25366 (2011)). The link between PRMT1 and cancer biology has largely been through regulation of methylation of arginine residues found on relevant substrates. In several tumor types, PRMT1 can drive expression of aberrant oncogenic programs through methylation of histone H4 (Takai, H. et al. 5-Hydroxymethylcytosine plays a critical role in glioblastomagenesis by recruiting the CHTOP-methylosome complex. *Cell Rep* 9, 48-60, doi:10.1016/j.celrep.2014.08.071 (2014); Shia, W. J. et al. PRMT1 interacts with AML1-ETO to promote its transcriptional activation and progenitor cell proliferative potential. *Blood* 119, 4953-4962, doi:10.1182/blood-2011-04-347476 (2012); Zhao, X. et al. Methylation of RUNX1 by PRMT1 abrogates SIN3A binding and potentiates its transcriptional activity. *Genes Dev* 22, 640-653, doi: 10.1101/gad.1632608 (2008), as well as through its activity on non-histone substrates (Wei, H., Mundade, R., Lange, K. C. & Lu, T. Protein arginine methylation of non-histone proteins and its role in diseases. *Cell Cycle* 13, 32-41, doi:10.4161/cc.27353(2014)). In many of these experimental systems, disruption of the PRMT1-dependent ADMA modification of its substrates decreases the proliferative capacity of cancer cells (Yang, Y. & Bedford, M. T. Protein arginine methyltransferases and cancer. *Nat Rev Cancer* 13, 37-50, doi:10.1038/nrc3409 (2013)).

PRMT5 functions in several types of complexes in the cytoplasm and the nucleus and binding partners of PRMT5 are required for substrate recognition and selectivity. Methylosome protein 50 (MEP50) is a known cofactor of PRMT5 that is required for PRMT5 binding and activity towards histones and other substrates (Ho M C, et al. Structure of the arginine methyltransferase PRMT5-MEP50 reveals a mechanism for substrate specificity. PLoS One. 2013; 8(2)).

PRMT5 symmetrically methylates arginines in multiple proteins, preferentially in regions rich in arginine and glycine residues (Karkhanis V, et al. Versatility of PRMT5-induced methylation in growth control and development. Trends Biochem Sci. 2011 December; 36(12):633-41). PRMT5 methylates arginines in various cellular proteins including splicing factors, histones, transcription factors, kinases and others (Karkhanis V, et al. Versatility of PRMT5-induced methylation in growth control and development. Trends Biochem Sci. 2011 December; 36(12):633-41). Methylation of multiple components of the spliceosome is a key event in spliceosome assembly and the attenuation of PRMT5 activity through knockdown or gene knockout leads to disruption of cellular splicing (Bezzi M, et al. Regulation of constitutive and alternative splicing by PRMT5 reveals a role for Mdm4 pre-mRNA in sensing defects in the spliceosomal machinery. Genes Dev. 2013 Sep. 1; 27(17):1903-16). PRMT5 also methylates histone arginine residues (H3R8, H2AR3 and H4R3) and these histone marks are associated with transcriptional silencing of tumor suppressor genes, such as RB and ST7 (Wang L, Pal S, Sif S. Protein arginine methyltransferase 5 suppresses the transcription of the RB family of tumor suppressors in leukemia and lymphoma cells. Mol Cell Biol. 2008 October; 28(20):6262-77). Additionally, symmetric dimethylation of H2AR3 has been implicated in the silencing of differentiation genes in embryonic stem cells (Tee W W, Pardo M, Theunissen T W, Yu L, Choudhary J S, Hajkova P, Surani M A. Prmt5 is essential for early mouse development and acts in the cytoplasm to maintain ES cell pluripotency. Genes Dev. 2010 Dec. 15; 24(24):2772-7). PRMT5 also plays a role in cellular signaling, through the methylation of EGFR and PI3K (Hsu J M, Chen C T, Chou C K, Kuo H P, Li L Y, Lin C Y, Lee H J, Wang Y N, Liu M, Liao H W, Shi B, Lai C C, Bedford M T, Tsai C H, Hung M C. Crosstalk between Arg 1175 methylation and Tyr 1173 phosphorylation negatively modulates EGFR-mediated ERK activation. Nat Cell Biol. 2011 February; 13(2):174-81; Wei T Y, Juan C C, Hisa J Y, Su L J, Lee Y C, Chou H Y, Chen J M, Wu Y C, Chiu S C, Hsu C P, Liu K L, Yu C T. Protein arginine methyltransferase 5 is a potential oncoprotein that upregulates G1 cyclins/cyclin-dependent kinases and the phosphoinositide 3-kinase/AKT signaling cascade. Cancer Sci. 2012 September; 103(9):1640-50).

Increasing evidence suggests that PRMT5 is involved in tumorigenesis. PRMT5 protein is overexpressed in a number of cancer types, including lymphoma, glioma, breast and lung cancer and PRMT5 overexpression alone is sufficient to transform normal fibroblasts (Pal S, Baiocchi R A, Byrd J C, Grever M R, Jacob S T, Sif S. Low levels of miR-92b/96 induce PRMT5 translation and H3R8/H4R3 methylation in mantle cell lymphoma. EMBO J. 2007 Aug. 8; 26(15):3558-69; Ibrahim R, et al. Expression of PRMT5 in lung adenocarcinoma and its significance in epithelial-mesenchymal transition. Hum Pathol. 2014 July; 45(7):1397-405; Powers M A, et al. Protein arginine methyltransferase 5 accelerates tumor growth by arginine methylation of the tumor suppressor programmed cell death 4. Cancer Res. 2011 Aug. 15; 71(16):5579-87; Yan F, et al. Genetic validation of the protein arginine methyltransferase PRMT5 as a candidate therapeutic target in glioblastoma. Cancer Res. 2014 Mar. 15; 74(6):1752-65). Knockdown of PRMT5 often leads to a decrease in cell growth and survival in cancer cell lines. In breast cancer, high PRMT5 expression, together with high PDCD4 (programmed cell death 4) levels predict overall poor survival (Powers M A, et al. Cancer Res. 2011 Aug. 15; 71(16):5579-87). PRMT5 methylates PDCD4 altering tumor-related functions. Co-expression of PRMT5 and PDCD4 in an orthotopic model of breast cancer promotes tumor growth. High expression of PRMT5 in glioma is associated with high tumor grade and overall poor survival and PRMT5 knockdown provides a survival benefit in an orthotopic glioblastoma model (Yan F, et al. Genetic validation of the protein arginine methyltransferase PRMT5 as a candidate therapeutic target in glioblastoma. Cancer Res. 2014 Mar. 15; 74(6):1752-65). Increased PRMT5 expression and activity contribute to silencing of several tumor suppressor genes in glioma cell lines.

The strongest mechanistic link currently described between PRMT5 and cancer is in mantle cell lymphoma (MCL). PRMT5 is frequently overexpressed in MCL and is highly expressed in the nuclear compartment where it increases the levels of histone methylation and silences a subset of tumor suppressor genes. Recent studies uncovered the role of miRNAs in the upregulation of PRMT5 expression in MCL. More than 50 miRNAs are predicted to anneal to the 3' untranslated region of PRMT5 mRNA. It was reported that miR-92b and miR-96 levels inversely correlate with PRMT5 levels in MCL and that the downregulation of these miRNAs in MCL cells results in the upregulation PRMT5 protein levels. Cyclin D1, the oncogene that is translocated in the vast majority of MCL patients, associates with PRMT5 and through a cdk4-dependent mechanism increases PRMT5 activity (Aggarwal P, et al. Nuclear cyclin D1/CDK4 kinase regulates CUL4 expression and triggers neoplastic growth via activation of the PRMT5 methyltransferase. Cancer Cell. 2010 Oct. 19; 18(4):329-40). PRMT5 mediates the suppression of key genes that negatively regulate DNA replication allowing for cyclin D1-dependent neoplastic growth. PRMT5 knockdown inhibits cyclin D1-dependent cell transformation causing death of tumor cells. These data highlight the important role of PRMT5 in MCL and suggest that PRMT5 inhibition could be used as a therapeutic strategy in MCL.

In other tumor types, PRMT5 has been postulated to play a role in differentiation, cell death, cell cycle progression, cell growth and proliferation. While the primary mechanism linking PRMT5 to tumorigenesis is unknown, emerging data suggest that PRMT5 contributes to regulation of gene expression (histone methylation, transcription factor binding, or promoter binding), alteration of splicing, and signal transduction. PRMT5 methylation of the transcription factor E2F1 decreases its ability to suppress cell growth and promote apoptosis (Zheng S, et al. Arginine methylation-dependent reader-writer interplay governs growth control by E2F-1. Mol Cell. 2013 Oct. 10; 52(1):37-51). PRMT5 also methylates p53 (Jansson M, et al. Arginine methylation regulates the p53 response. Nat Cell Biol. 2008 December; 10(12):1431-9) in response to DNA damage and reduces the ability of p53 to induce cell cycle arrest while increasing p53-dependent apoptosis. These data suggest that PRMT5 inhibition could sensitize cells to DNA damaging agents through the induction of p53-dependent apoptosis.

In addition to directly methylating p53, PRMT5 upregulates the p53 pathway through a splicing-related mechanism. PRMT5 knockout in mouse neural progenitor cells results in the alteration of cellular splicing including isoform switching of the MDM4 gene (Bezzi M, et al. Regulation of constitutive and alternative splicing by PRMT5 reveals a role for Mdm4 pre-mRNA in sensing defects in the spliceosomal machinery. Genes Dev. 2013 Sep. 1; 27(17):1903-16). Bezzi et al. discovered that PRMT5 knockout cells have decreased expression of a long MDM4 isoform (resulting in a functional p53 ubiquitin ligase) and increased expression of a short isoform of MDM4 (resulting in an inactive ligase). These changes in MDM4 splicing result in the inactivation of MDM4, increasing the stability of p53 protein, and subsequently, activation of the p53 pathway and cell death. MDM4 alternative splicing was also observed in PRMT5 knockdown cancer cell lines. These data suggest PRMT5 inhibition could activate multiple nodes of the p53 pathway.

In addition to the regulation of cancer cell growth and survival, PRMT5 is also implicated in the epithelial-mesenchymal transition (EMT). PRMT5 binds to the transcription factor SNAIL, and serves as a critical co-repressor of E-cadherin expression; knockdown of PRMT5 results in the upregulation of E-cadherin levels (Hou Z, et al. The LIM protein AJJBA recruits protein arginine methyltransferase 5 to mediate SNAIL-dependent transcriptional repression. Mol Cell Biol. 2008 May; 28(10):3198-207).

Though there have been many recent advances in the treatment of cancer, there remains a need for more effective and/or enhanced treatment of an individual suffering the effects of cancer.

BRIEF DESCRIPTION OF THE DRAWINGS

FIG. 4: Mode of inhibition against PRMT1 by Compound A. $IC_{50}$ values were determined following a 18 minute PRMT1 reaction and fitting the data to a 3-parameter dose-response equation. (A) Representative experiment showing Compound A $IC_{50}$ values plotted as a function of $[SAM]/K_m^{app}$ fit to an equation for uncompetitive inhibition $IC_{50}=K_i/(1+(K_m/[S]))$. (B) Representative experiment showing $IC_{50}$ values plotted as a function of $[Peptide]/K_m^{app}$. Inset shows data fit to an equation for mixed inhibition to evaluate Compound A inhibition of PRMT1 with respect to peptide H4 1-21 substrate ($v=V_{max}*[S]/(K_m*(1+[I]/K_i)+[S]*(1+[I]/K'))$). An alpha value ($\alpha=K_i'/K_i$)>0.1 but<10 is indicative of a mixed inhibitor.

FIG. 7: Inhibition of PRMT1 orthologs by Compound A. PRMT1 activity was monitored using a radioactive assay run under balanced conditions (substrate concentrations equal to $K_m^{app}$) measuring transfer of $^3H$ from SAM to a H4 1-21 peptide. $IC_{50}$ values were determined by fitting the data to a 3-parameter dose-response equation. (A) $IC_{50}$ values plotted as a function of PRMT1:SAM:Compound A preincubation time for rat (○) and dog (●) orthologs. (B) $IC_{50}$ values plotted as a function of rat (○), dog (●) or human (□) PRMT1 concentration. (C) $IC_{50}$ values were determined following a 60 minute PRMT1:SAM:Compound A preincubation and a 20 minute reaction. Data is an average from testing multiple salt forms of Compound A. $K^{*a}pp$ values were calculated based on the equation $K_i=IC_{50}/(1+(K_m/[S]))$ for an uncompetitive inhibitor and the assumption that the $IC_{50}$ determination was representative of the ESI* conformation.

FIG. 22: In vitro proliferation timecourse of ccRCC cines with Compound A. (A) Growth relative to control (DMSO) for 2 ccRCC cell lines. Representative curves from a single replicate are shown. (B) Summary of $gIC_{50}$ and % growth inhibition for ccRCC cell lines during the timecourse (Average SD; n=2 for each line).

FIG. 54: gIC50 and gIC100 fold changes relative to single agent (Compound B) treatment in various triple negative breast cancer (TNBC) cell lines treated with fixed ratio combinations of Compound B with Cisplatin, Carboplatin, Doxorubicin, BET inhibitor, MEK inhibitor, and Compound D.

FIG. 55: gIC50 and gIC100 fold changes relative to single agent (Compound B) treatment in various bladder cancer cell lines treated with fixed ratio combinations of Compound B with Cisplatin, Carboplatin, Doxorubicin, BET inhibitor, MEK inhibitor, and Compound D.

FIG. 58: Results of proliferation assays of 10 bladder cancer lines and 7 TNBC cell lines treated with a combination of Compound B and Compound D. The percentages of bladder cancer and TNBC cell lines that underwent cytotoxic (negative $Y_{min}$-T0%) and cytostatic responses are shown.

SUMMARY OF THE INVENTION

Figure 1:
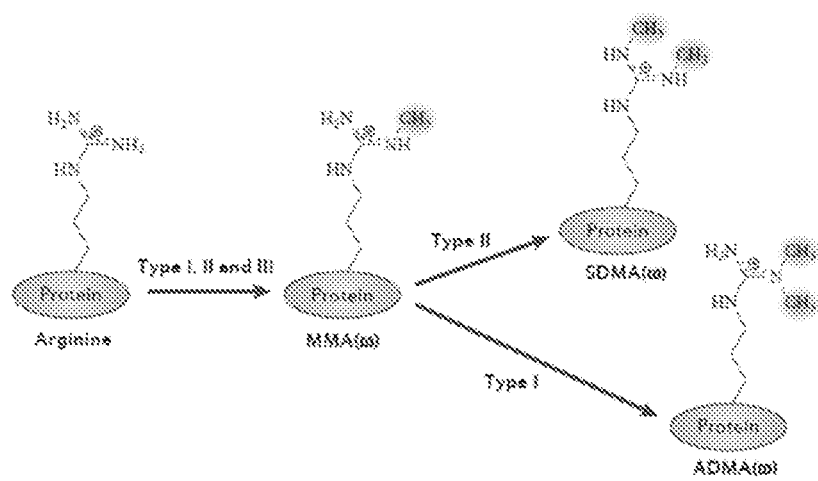
FIG. 1: Types of methylation on arginine residues. From Yang, Y. & Bedford, M. T. Protein arginine methyltransferases and cancer. Nat Rev Cancer 13, 37-50, doi:10.1038/nrc3409 (2013).

In one embodiment the present invention provides a combination of a Type I protein arginine methyltransferase (Type I PRMT) inhibitor and a Type II protein arginine methyltransferase (Type II PRMT) inhibitor.

In one embodiment, a pharmaceutical composition comprising a therapeutically effective amount of a Type I protein arginine methyltransferase (Type I PRMT) inhibitor and a second pharmaceutical composition comprising a therapeutically effective amount of a Type II protein arginine methyltransferase (Type II PRMT) inhibitor are provided.

In one embodiment, methods are provided for treating cancer in a human in need thereof, the methods comprising administering to the human a combination of a Type I protein arginine methyltransferase (Type I PRMT) inhibitor and a Type II protein arginine methyltransferase (Type II PRMT) inhibitor, together with at least one of: a pharmaceutically acceptable carrier and a pharmaceutically acceptable diluent, thereby treating the cancer in the human.

In one embodiment, methods of treating cancer in a human in need thereof are provided, the methods comprising administering to the human a therapeutically effective amount of a pharmaceutical composition comprising a Type I protein arginine methyltransferase (Type I PRMT) inhibitor and a pharmaceutical composition comprising a a Type II protein arginine methyltransferase (Type II PRMT) inhibitor, thereby treating the cancer in the human.

DETAILED DESCRIPTION OF THE INVENTION

Definitions

As used herein "Type I protein arginine methyltransferase inhibitor" or "Type I PRMT inhibitor" means an agent that inhibits any one or more of the following: protein arginine methyltransferase 1 (PRMT1), protein arginine methyltransferase 3 (PRMT3), protein arginine methyltransferase 4 (PRMT4), protein arginine methyltransferase 6 (PRMT6) inhibitor, and protein arginine methyltransferase 8 (PRMT8). In some embodiments, the Type I PRMT inhibitor is a small molecule compound. In some embodiments, the Type I PRMT inhibitor selectively inhibits any one or more of the following: protein arginine methyltransferase 1 (PRMT1), protein arginine methyltransferase 3 (PRMT3), protein arginine methyltransferase 4 (PRMT4), protein arginine methyltransferase 6 (PRMT6) inhibitor, and protein arginine methyltransferase 8 (PRMT8). In some embodiments, the Type I PRMT inhibitor is a selective inhibitor of PRMT1, PRMT3, PRMT4, PRMT6, and PRMT8.

As used herein "Type II protein arginine methyltransferase inhibitor" or "Type II PRMT 15 inhibitor" means an agent that inhibits protein arginine methyltransferase 5 (PRMT5) and/or protein arginine methyltransferase 9 (PRMT9). In some embodiments, the Type II PRMT inhibitor is a small molecule compound. In some embodiments, the Type II PRMT inhibitor selectively inhibits protein arginine methyltransferase 5 (PRMT5) and/or protein arginine methyltransferase 9 (PRMT9). In some embodiments, the Type II PRMT inhibitor is an inhibitor of PRMT5. In some embodiments, the Type II PRMT inhibitor is a selective inhibitor of PRMT5.

Arginine methyltransferases are attractive targets for modulation given their role in the regulation of diverse biological processes. It has now been found that compounds described herein, and pharmaceutically acceptable salts and compositions thereof, are effective as inhibitors of arginine methyltransferases.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5$^{th}$ Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et ah, Enantiomers, Racemates and Resolutions (Wiley Interscience, New York, 1981); Wilen et ah, Tetrahedron 33:2725 (1977); Eliel, Stereochemistry of Carbon Compounds (McGraw-Hill, N Y, 1962); and Wilen, Tables of Resolving Agents and Optical Resolutions p. 268 (E.L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

It is to be understood that the compounds of the present invention may be depicted as different tautomers. It should also be understood that when compounds have tautomeric forms, all tautomeric forms are intended to be included in the scope of the present invention, and the naming of any compound described herein does not exclude any tautomer form.

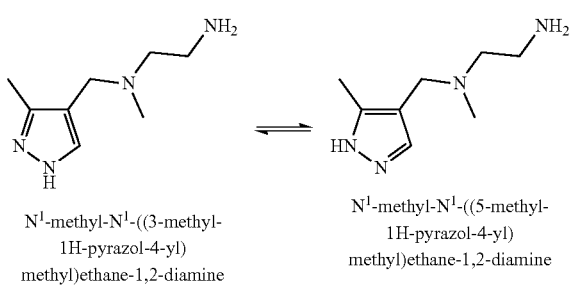

N¹-methyl-N¹-((3-methyl-1H-pyrazol-4-yl)methyl)ethane-1,2-diamine

N¹-methyl-N¹-((5-methyl-1H-pyrazol-4-yl)methyl)ethane-1,2-diamine

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

The term "aliphatic," as used herein, includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups. As will be appreciated by one of ordinary skill in the art, "aliphatic" is intended herein to include alkyl, alkenyl, alkynyl, cycloalkyl, and cycloalkenyl moieties.

When a range of values is listed, it is intended to encompass each value and subrange within the range. For example "$C_{1-6}$ alkyl" is intended to encompass, $C_1$; $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Radical" refers to a point of attachment on a particular group. Radical includes divalent radicals of a particular group.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. In certain embodiments, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms and one or more carbon-carbon double bonds (e.g., 1, 2, 3, or 4 double bonds), and optionally one or more triple bonds (e.g., 1, 2, 3, or 4 triple bonds) ("$C_{2-2}$ alkenyl"). In certain embodiments, alkenyl does not comprise triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_2$-alkenyl"). In some embodiments, an alkenyl group has 2 to 7 carbon atoms ("$C_{2-7}$ alkenyl") In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. In certain embodiments, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms and one or more carbon-carbon triple bonds (e.g., 1, 2, 3, or 4 triple bonds), and optionally one or more double bonds (e.g., 1, 2, 3, or 4 double bonds) ("$C_{2-20}$ alkynyl"). In certain embodiments, alkynyl does not comprise double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. In certain embodiments, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-1}$ alkynyl.

"Fused" or "ortho-fused" are used interchangeably herein, and refer to two rings that have two atoms and one bond in common, e.g.,

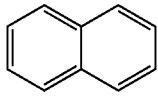

napthalene

"Bridged" refers to a ring system containing (1) a bridgehead atom or group of atoms which connect two or more non-adjacent positions of the same ring; or (2) a bridgehead atom or group of atoms which connect two or more positions of different rings of a ring system and does not thereby form an ortho-fused ring, e.g.,

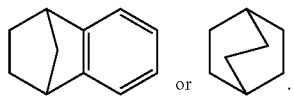

"Spiro" or "Spiro-fused" refers to a group of atoms which connect to the same atom of a carbocyclic or heterocyclic ring system (geminal attachment), thereby forming a ring, e.g.,

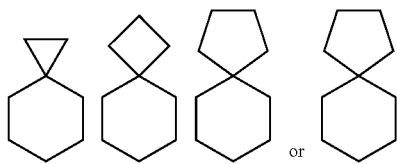

Spiro-fusion at a bridgehead atom is also contemplated.

"Carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In certain embodiments, a carbocyclyl group refers to a radical of a non-aromatic cyclic hydrocarbon group having from 3 to 10 ring carbon atoms ($C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or is a fused, bridged or spiro-fused ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. In certain embodiments, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments,"carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl (C). In certain embodiments, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In certain embodiments, heterocyclyl or heterocyclic refers to a radical of a 3-10 membered non-aromatic ring system having ring carbon atoms and 1-4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro-fused ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. In certain embodiments, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms independently selected from nitrogen, oxygen, and sulfur. In some embodiments, the 5-6 membered heterocyclyl has 1-2 ring heteroatoms independently selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. In certain embodiments, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-14 membered monocyclic or polycyclic (e.g., bicyclic or tricyclic) 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In certain embodiments, heteroaryl refers to a radical of a 5-10 membered monocyclic or bicyclic 4n+2 aromatic ring system having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings.

"Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-14 membered aromatic ring system having ring carbon atoms and 1-4 ring heteroatoms provided in the aromatic ring system, wherein each heteroatom is independently selected from nitrogen, oxygen, and sulfur ("5-14 membered heteroaryl"). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms independently selected from nitrogen, oxygen, and sulfur. In some embodiments, the 5-6 membered heteroaryl has 1-2 ring heteroatoms independently selected from nitrogen, oxygen, and sulfur. In some embodiments, the 5-6 membered heteroaryl has 1 ring heteroatom selected from nitrogen, oxygen, and sulfur. In certain embodiments, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary 5,6-bicyclic heteroaryl groups include, without limitation, any one of the following formulae:

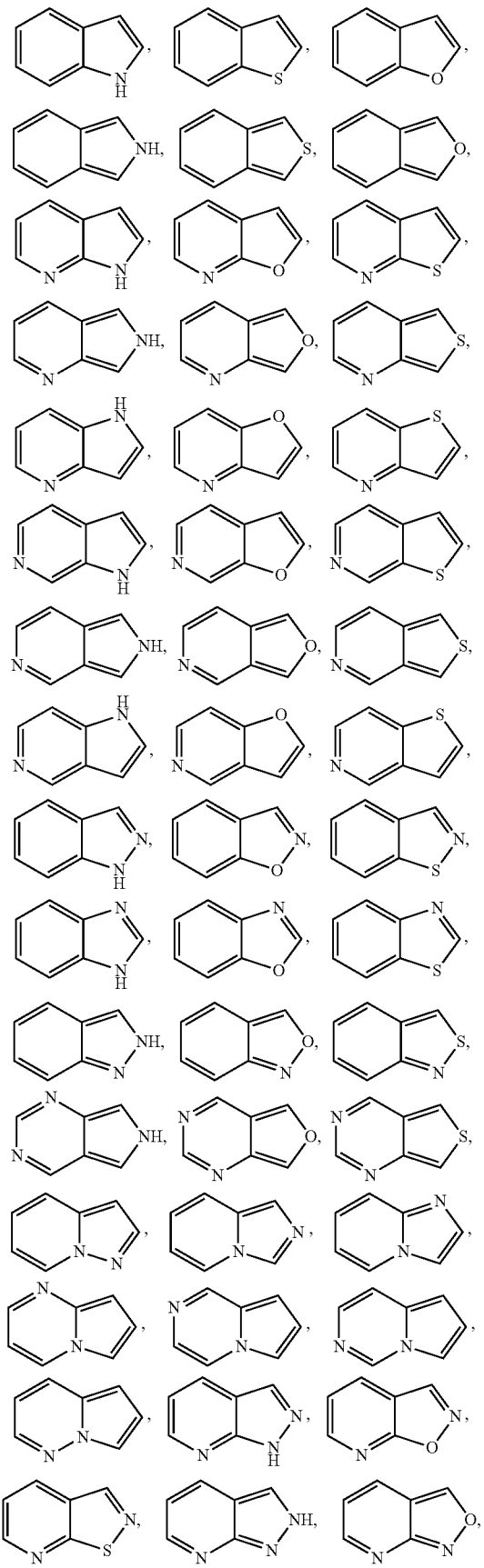

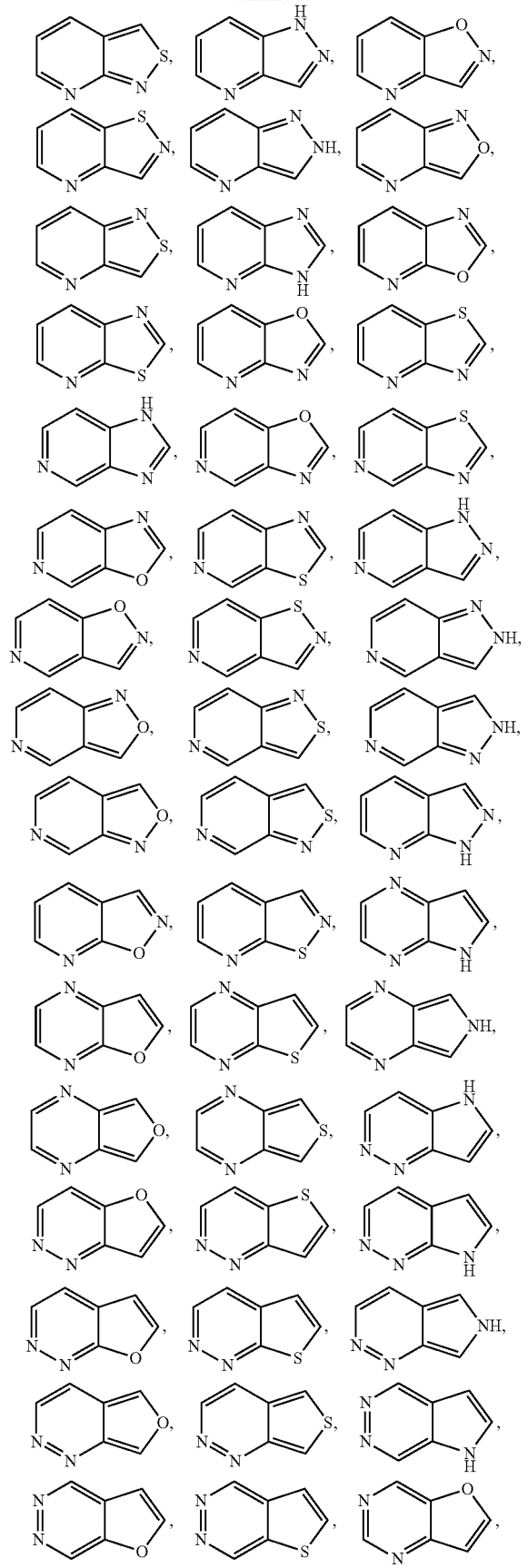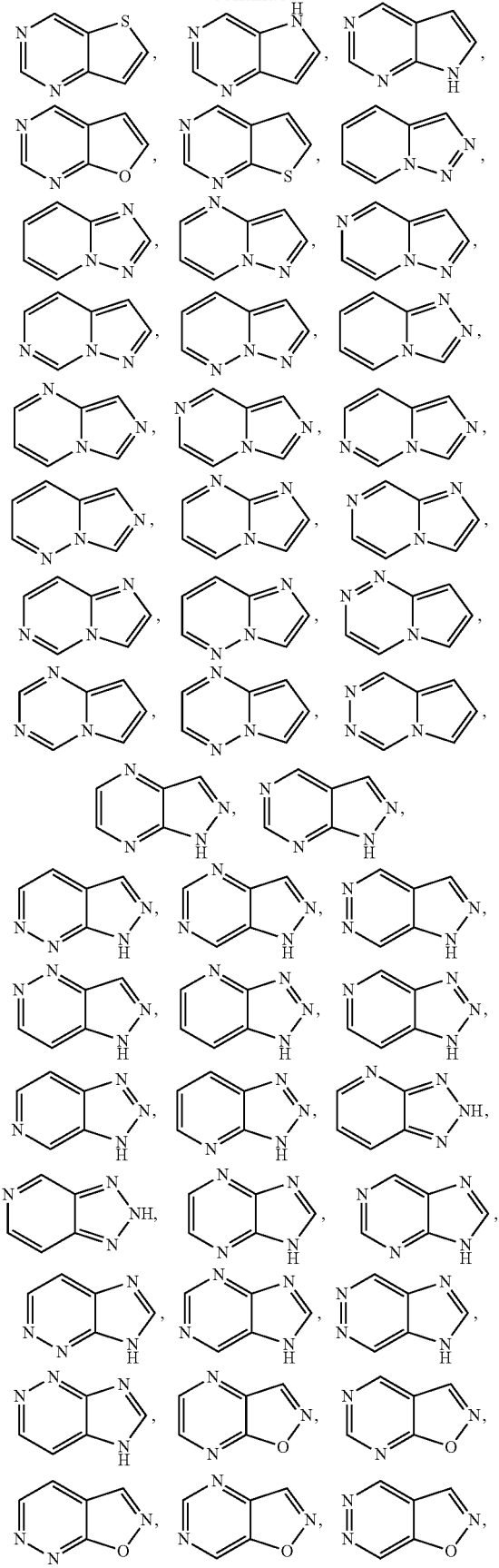

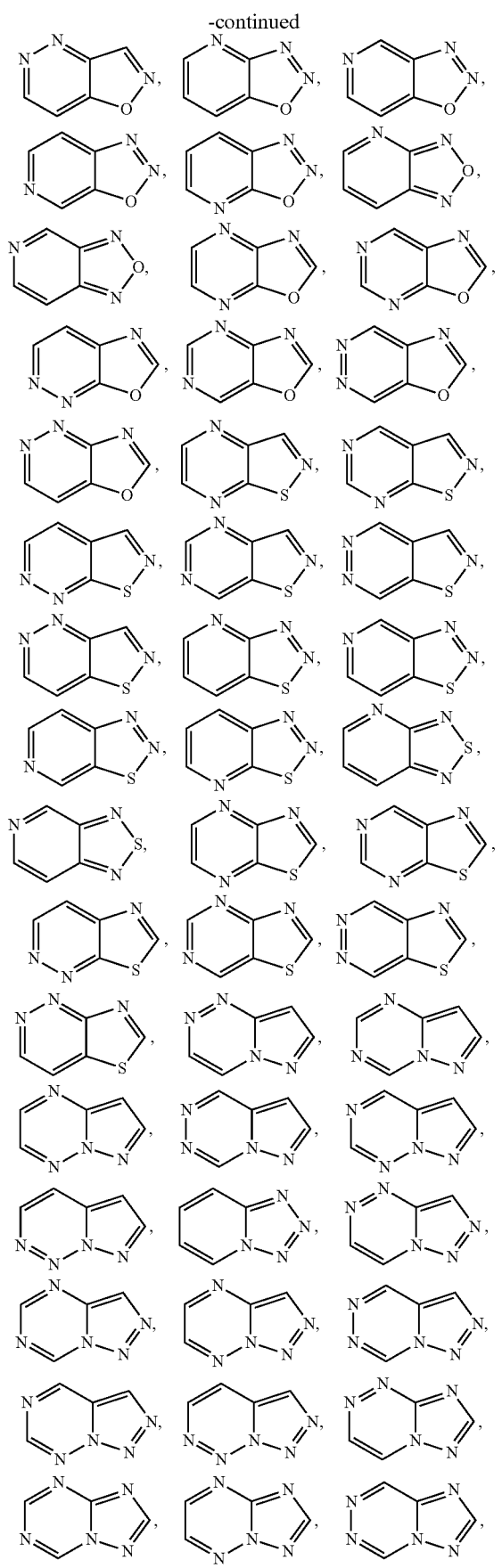
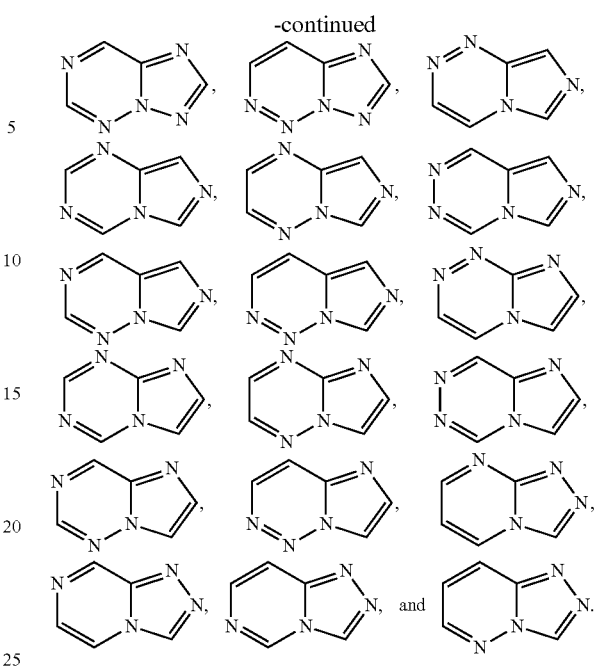

In any of the monocyclic or bicyclic heteroaryl groups, the point of attachment can be any carbon or nitrogen atom, as valency permits.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, aliphatic, alkyl, alkenyl, alkynyl, carbocyclyl, heterocyclyl, aryl, and heteroaryl groups, as defined herein, are optionally substituted (e.g., "substituted" or "unsubstituted" aliphatic, "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, including any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$—NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$ or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$—N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-101}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{cc}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{1-6}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —O$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X, —N(OC$_{1-6}$ alkyl)(C$_{1-6}$ alkyl), —N(OH)(C$_{1-6}$ alkyl), —NH(OH), —SH, —S$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_6$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{CC}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{CC}$)OR$^{aa}$, —C(=NR$^{CC}$)N(R$^{CC}$)$_2$, —SO$_2$N(R$^{cc}$)$_2$, —SO$_2$R$^{cc}$, —SO$_2$OR$^{cc}$, —SOR$^{aa}$, —C(=S)N(R$^{CC}$)$_2$, —C(=O)SR$^{cc}$, —C(=S)SR$^{CC}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{CC}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{CC}$)N(R$^{CC}$)$_2$, —SO$_2$N(R$^{cc}$)$_2$, —SO$_2$R$^{cc}$, —SO$_2$OR$^{cc}$, —SOR$^{aa}$, —C(=S)N(R$^{CC}$)$_2$—C(=O)SR$^{cc}$, —C(=S)SR$^{CC}$, C$_{1-10}$ alkyl {e.g., aralkyl, heteroalkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R groups, and wherein R$^{aa}$, R$^{bb}$, R$^{cc}$, and R$^{dd}$ are as defined herein. Nitrogen protecting groups are well known in the art and include those described in detail in Protecting Groups in Organic Synthesis, T. W. Greene and P. G. M. Wuts, 3 rd edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-{p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10-tetrahydrothioxanthyl)] methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-{N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)] methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5, 6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7, 8-pentamethylchroman-6-sulfonamide (Pmc), methanesulfonamide (Ms), 3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl] amine (MMTr), N-9-phenylfluorenylamine (PhF), N-2,7-dichloro-9-fluorenylmethyleneamine, N-ferrocenylmethylamino (Fcm), N-2-picolylamino N-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N,N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl] amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R)_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(Ra)_3$, —$P(R^{CC})_2$, —$P(R^{CC})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3 edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolylN-oxide, diphenylmethyl,p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), t-butyl carbonate (BOC), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate, alkyl allyl carbonate, alkyl p-nitrophenyl carbonate, alkyl benzyl carbonate, alkylp-methoxybenzyl carbonate, alkyl 3,4-dimethoxybenzyl carbonate, alkyl o-nitrobenzyl carbonate, alkylp-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(Rb)_2$, —$C(=O)SR^{aa}$, —$C(=O)R^{aa}$, —$CO_2R^{aa}$, —$C(=O)N(Rb)_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$—$P(R^{CC})_2$, —$P(R^{CC})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein.

Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

As used herein, a "leaving group", or "LG", is a term understood in the art to refer to a molecular fragment that departs with a pair of electrons upon heterolytic bond cleavage, wherein the molecular fragment is an anion or neutral molecule. See, for example, Smith, March Advanced Organic Chemistry 6th ed. (501-502). Examples of suitable leaving groups include, but are not limited to, halides (such as chloride, bromide, or iodide), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, haloformates, —N02, trialkylammonium, and aryliodonium salts. In some embodiments, the leaving group is a sulfonic acid ester. In some embodiments, the sulfonic acid ester comprises the formula —OSO$_2$R$^{LG1}$ wherein R$^{LG1}$ is selected from the group consisting alkyl optionally, alkenyl optionally substituted, heteroalkyl optionally substituted, aryl optionally substituted, heteroaryl optionally substituted, arylalkyl optionally substituted, and heterarylalkyl optionally substituted. In some embodiments, R$^{LG1}$ is substituted or unsubstituted C$_1$-C$_6$ alkyl. In some embodiments, R$^{LG1}$ is methyl. In some embodiments, R$^{LG1}$ is substituted or unsubstituted aryl. In some embodiments, R$^{LG1}$ is substituted or unsubstituted phenyl. In some embodiments, R$^{LG1}$ is:

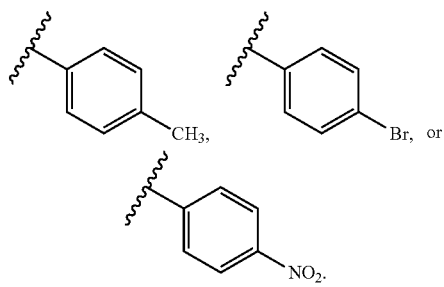

In some cases, the leaving group is toluenesulfonate (tosylate, Ts), methanesulfonate (mesylate, Ms), p-bromobenzenesulfonyl (brosylate, Bs), or trifluoromethanesulfonate (triflate, Tf). In some cases, the leaving group is a brosylate (p-bromobenzenesulfonyl). In some cases, the leaving group is a nosylate (2-nitrobenzenesulfonyl). In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate.

These and other exemplary substituents are described in more detail in the Examples and claims. The present disclosure is not intended to be limited in any manner by the above exemplary listing of substituents.

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences (1977) 66: 1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, quaternary salts.

The present invention provides Type I PRMT inhibitors. In one embodiment, the Type I PRMT inhibitor is a compound of Formula (I):

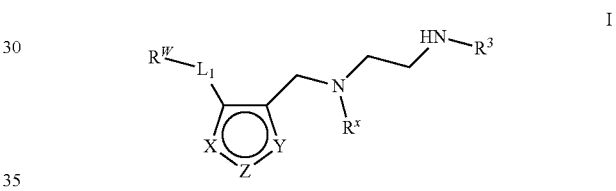

or a pharmaceutically acceptable salt thereof,
wherein
X is N, Z is NR$^4$, and Y is CR$_5$; or
X is NR$^4$, Z is N, and Y is CR$^5$; or
X is CR$^5$, Z is NR$^4$, and Y is N; or
X is CR$^5$, Z is N, and Y is NR$^4$;
R$^X$ is optionally substituted C$_{1-4}$ alkyl or optionally substituted C$_{3-4}$ cycloalkyl;
L$_1$ is a bond, —O—, —N(R$^B$)—, —S—, —C(O)—, —C(O)O—, —C(O)S—, —C(O)N(R$^B$)—, —C(O)N(R$^B$)N(R$^B$)—, —OC(O)—, —OC(O)N(R$^B$), NR$^B$C(O)—, —NR$^B$C(O)N(R$^B$)—NR$^B$C(O)N(R$^B$)N(R$^B$)— NR$^B$C(O)O—, —SC(O)—, —C(=NR$^B$)—, —C(=NNR$^B$)—, —C(=NOR$^A$)—, —C(=NR$^B$)N(R$^B$)—, —NR$^B$C(=NR$^B$)—, —C(S)—, —C(S)N(R$^B$)—, —NR$^B$C(S)—, —S(O)—, —OS(O)$_2$—, —S(O)$_2$O—, —SO$_2$—, —N(R$^B$)SO$_2$—, —SO$_2$N(R$^B$)—, or an optionally substituted C$_{1-6}$ saturated or unsaturated hydrocarbon chain, wherein one or more methylene units of the hydrocarbon chain is optionally and independently replaced with —O—, —N(R$^B$), —S—, —C(O)—, —C(O)O—, —C(O)S—, —C(O)N(R$^B$)—, —C(O)N(R$^B$)N(R$^B$)—, —OC(O)—, —OC(O)N(R$^B$)—, —NR$^B$C(O)—, —NR$^B$C(O)N(R$^B$)— NR$^B$C(O)N(R$^B$)N(R$^B$)—, —NR$^B$C(O)O—, —SC(O)—, —C(=NR$^B$)—, —C(=NNR$^B$)—, —C(=NOR$^A$)—, —C(=NR$^B$)N(R$^B$)—, —NR$^B$C(=NR$^B$)—, —C(S)—, —C(S)N(R$^B$)—, —NR$^B$C(S)—, —S(O)—, —OS(O)$_2$—, —S(O)$_2$O—, —SO$_2$—, —N(R$^B$)SO$_2$—, or —SO$_2$N(R$^B$)—;
each R$^A$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

each $R^B$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or an $R^B$ and $R^W$ on the same nitrogen atom may be taken together with the intervening nitrogen to form an optionally substituted heterocyclic ring;

$R^W$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; provided that when $L_1$ is a bond, $R^W$ is not hydrogen, optionally substituted aryl, or optionally substituted heteroaryl;

$R^3$ is hydrogen, $C_{1-4}$ alkyl, or $C_{3-4}$ cycloalkyl;

$R^4$ is hydrogen, optionally substituted $C_{1-6}$ alkyl, optionally substituted $C_{2-6}$ alkenyl, optionally substituted $C_{2-6}$ alkynyl, optionally substituted $C_{3-7}$ cycloalkyl, optionally substituted 4-to 7-membered heterocyclyl; or optionally substituted $C_{1-4}$ alkyl-Cy;

Cy is optionally substituted $C_{3-7}$ cycloalkyl, optionally substituted 4- to 7-membered heterocyclyl, optionally substituted aryl, or optionally substituted heteroaryl; and $R^5$ is hydrogen, halo, —CN, optionally substituted $C_{1-4}$ alkyl, or optionally substituted $C_{3-4}$ cycloalkyl. In one aspect, $R^3$ is a $C_{1-4}$ alkyl. In one aspect, $R^3$ is methyl. In one aspect, $R^4$ is hydrogen. In one aspect, $R^5$ is hydrogen. In one aspect, $L_1$ is a bond.

In one embodiment, the Type I PRMT inhibitor is a compound of Formula (I) wherein $-L_1-R^W$ is optionally substituted carbocyclyl. In one aspect, $R^3$ is a $C_{1-4}$ alkyl. In one aspect, $R^3$ is methyl. In another aspect, $R^4$ is hydrogen. In one aspect, $R^5$ is hydrogen. In one aspect, $L_1$ is a bond.

In one embodiment, the Type I PRMT inhibitor is a compound of Formula (V)

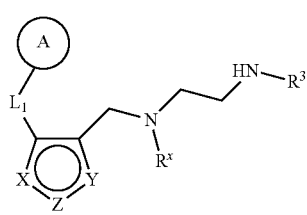

V or a pharmaceutically acceptable salt thereof, wherein Ring A is optionally substituted carbocyclyl, optionally substituted heterocyclyl, optionally substituted aryl, or optionally substituted heteroaryl. In one aspect, Ring A is optionally substituted carbocyclyl. In one aspect, $R^3$ is a $C_{1-4}$ alkyl. In one aspect, $R^3$ is methyl. In one aspect, $R^x$ is unsubstituted $C_{1-4}$ alkyl. In one aspect, $R^x$ is methyl. In one aspect, $L_1$ is a bond.

In one embodiment, the Type I PRMT inhibitor is a compound of Formula (VI)

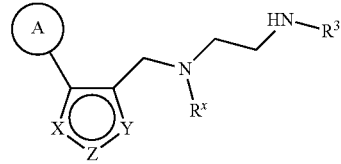

VI or a pharmaceutically acceptable salt thereof. In one aspect, Ring A is optionally substituted carbocyclyl. In one aspect, $R^3$ is a $C_{1-4}$ alkyl. In one aspect, $R^3$ is methyl. In one aspect, $R^x$ is unsubstituted $C_{1-4}$ alkyl. In one aspect, $R^x$ is methyl.

In one embodiment, the Type I PRMT inhibitor is a compound of Formula (II):

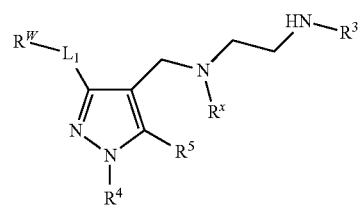

II or a pharmaceutically acceptable salt thereof. In one aspect, $-L_1-R^W$ is optionally substituted carbocyclyl. In one aspect, $R^3$ is a $C_{1-4}$ alkyl. In one aspect, $R^3$ is methyl. In one aspect, $R^x$ is unsubstituted $C_{1-4}$ alkyl. In one aspect, $R^x$ is methyl. In one aspect, $R^4$ is hydrogen.

In one embodiment, the Type I PRMT inhibitor is Compound A:

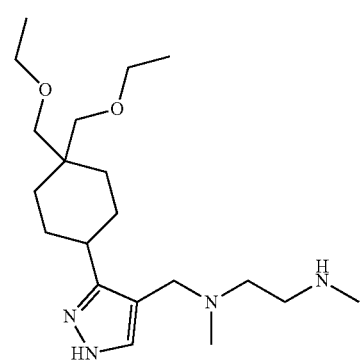

(A)

or a pharmaceutically acceptable salt thereof. Compound A and methods of making Compound A are disclosed in PCT/US2014/029710, in at least page 171 (Compound 158) and page 266, paragraph [00331].

In one embodiment, the Type I PRMT inhibitor is Compound A-tri-HCl, a tri-HCl salt form of Compound A. In another embodiment, the Type I PRMT inhibitor is Compound A-mono-HCl, a mono-HCl salt form of Compound A. In yet another embodiment, the Type I PRMT inhibitor is Compound A-free-base, a free base form of Compound A. In still another embodiment, the Type I PRMT inhibitor is Compound A-di-HCl, a di-HCl salt form of Compound A.

In one embodiment, the Type I PRMT inhibitor is Compound D:

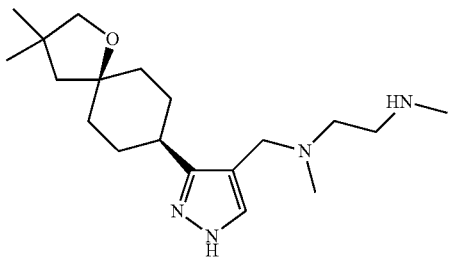

or a pharmaceutically acceptable salt thereof.

Type I PRMT inhibitors are further disclosed in PCT/US2014/029710, which is incorporated herein by reference. Exemplary Type I PRMT inhibitors are disclosed in Table 1A and Table 1B of PCT/US2014/029710, and methods of making the Type I PRMT inhibitors are described in at least page 226, paragraph [00274] to page 328, paragraph [00050] of PCT/US2014/029710.

The present invention also provides Type II PRMT inhibitors. In one embodiment, the Type II PRMT inhibitor is a compound of Formula (III):

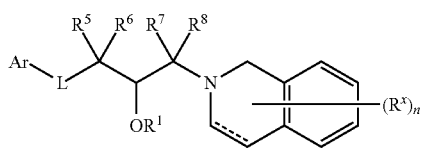

or a pharmaceutically acceptable salt thereof, wherein

===== represents a single or double bond;

$R^1$ is hydrogen, $R^z$, or —C(O)$R^z$, wherein $R^z$ is optionally substituted $C_{1-6}$ alkyl;

L is —N(R)C(O)—, —C(O)N(R)—, —N(R)C(O)N(R)—, —N(R)C(O)O—, or —OC(O)N(R)—;

each R is independently hydrogen or optionally substituted $C_{1-6}$ aliphatic;

Ar is a monocyclic or bicyclic aromatic ring having 0-4 heteroatoms independently selected from nitrogen, oxygen, and sulfur, wherein Ar is substituted with 0, 1, 2, 3, 4, or 5 $R^y$ groups, as valency permits;

each $R^y$ is independently selected from the group consisting of halo, —CN, —NO$_2$, optionally substituted aliphatic, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, RBC(O)N(R$^B$)N(R$^B$)$_2$, NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$, each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^5$, $R^6$, $R^7$, and $R^8$ are independently hydrogen, halo, or optionally substituted aliphatic;

each $R^X$ is independently selected from the group consisting of halo, —CN, optionally substituted aliphatic, —OR', and —N(R")$_2$;

R' is hydrogen or optionally substituted aliphatic;

each R" is independently hydrogen or optionally substituted aliphatic, or two R" are taken together with their intervening atoms to form a heterocyclic ring; and n is 0, 1, 2, 3, 4, 5, 6, 7, 8, 9, or 10, as valency permits.

In one aspect, L is —C(O)N(R)—. In one aspect, R is hydrogen. In one aspect, n is 0.

In one embodiment, the Type II PRMT inhibitor is a compound of Formula (IV):

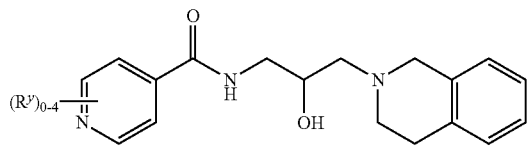

or a pharmaceutically acceptable salt thereof. In one aspect, at least one $R^y$ is —NHR$^B$. In one aspect, $R^B$ is optionally substituted cycloalkyl.

In one embodiment, the Type II PRMT inhibitor is a compound of Formula (VII):

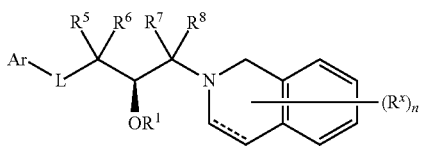

or a pharmaceutically acceptable salt thereof. In one aspect, L is —C(O)N(R)—. In one aspect, R is hydrogen. In one aspect, n is 0.

In one embodiment, the Type II PRMT inhibitor is a compound of Formula (VIII):

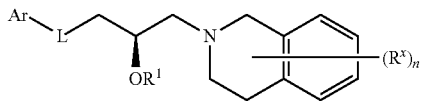

or a pharmaceutically acceptable salt thereof. In one aspect, L is —C(O)N(R)—. In one aspect, $R^1$ is hydrogen. In one aspect, n is 0.

In one embodiment, the Type II PRMT inhibitor is a compound of Formula (IX):

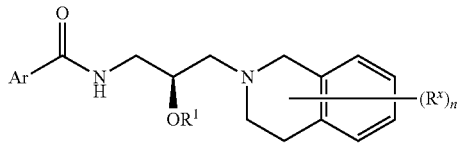
(IX)

or a pharmaceutically acceptable salt thereof.

In one embodiment, the Type II PRMT inhibitor is Compound B:

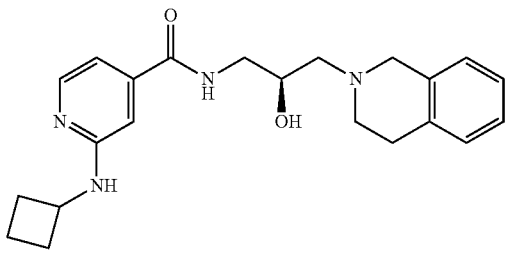
(B)

or a pharmaceutically acceptable salt thereof.

In one embodiment, the Type II PRMT inhibitor is a compound of Formula (X):

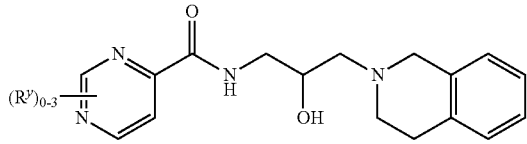
X or a pharmaceutically acceptable salt thereof. In one aspect, $R^y$ is —NHR$^B$. In one aspect, $R^B$ is optionally substituted heterocyclyl.

In certain embodiments, the Type II PRMT inhibitor is a compound of Formula (XI):

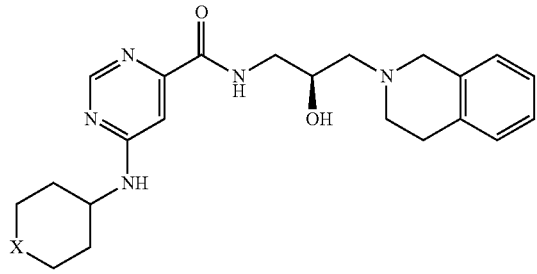
(XI)

or a pharmaceutically acceptable salt thereof, wherein X is —C(R$^{XC}$)$_2$, —O—, —S—, or —NR$^{XN}$—, wherein each instance of R$^{XC}$ is independently hydrogen, optionally substituted alkyl, optionally substituted carbocyclyl, optionally substituted heterocyclyl, optionally substituted aryl, or optionally substituted heteroaryl; R$^{XN}$ is independently hydrogen, optionally substituted alkyl, optionally substituted carbocyclyl, optionally substituted heterocyclyl, optionally substituted aryl, optionally substituted heteroaryl, —C(=O)R$^{XA}$, or a nitrogen protecting group; R$^{XA}$ is optionally substituted alkyl, optionally substituted carbocyclyl, optionally substituted heterocyclyl, optionally substituted aryl, or optionally substituted heteroaryl.

In one embodiment, the Type II PRMT inhibitor is Compound C:

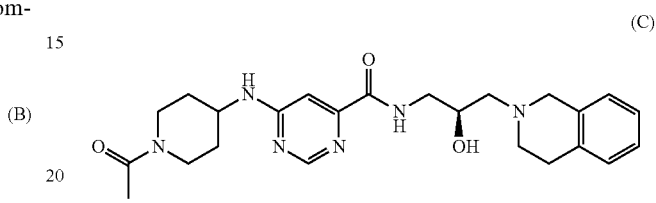
(C)

or a pharmaceutically acceptable salt thereof. Compound C and methods of making Compound C are disclosed in PCT/US2013/077235, in at least page 141 (Compound 208) and page 291, paragraph [00464] to page 294, paragraph [00469].

In another embodiment, the Type II PRMT inhibitor is Compound E:

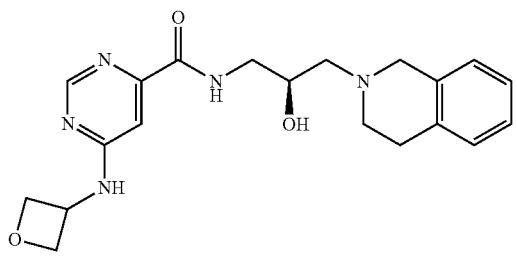
(E)

or a pharmaceutically acceptable salt thereof.

In another embodiment, the Type II PRMT inhibitor is Compound F:

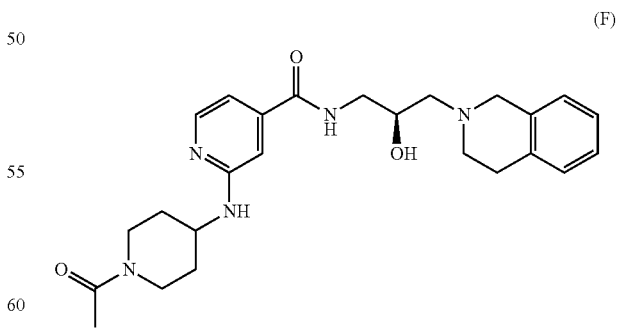
(F)

or a pharmaceutically acceptable salt thereof.

Type II PRMT inhibitors are further disclosed in PCT/US2013/077235 and PCT/US2015/043679, which are incorporated herein by reference. Exemplary Type II PRMT inhibitors are disclosed in Table 1A, Table 1B, Table 1C, Table 1D, Table 1E, Table 1F, and Table 1G of PCT/US2013/077235, and methods of making the Type II PRMT inhibitors are described in at least page 239, paragraph [00359] to page 301, paragraph [00485] of PCT/US2013/077235. Other non-limiting examples of Type II PRMT inhibitors or PRMT5 inhibitors are disclosed in the following published patent applications WO2011/079236, WO2014/100695, WO014/100716, WO2014/100730, WO2014/100764, and WO2014/100734, and U.S. Provisional Application Nos. 62/017,097 and 62/017,055. The generic and specific compounds described in these patent applications are incorporated herein by reference and can be used to treat cancer as described herein. In some embodiments, the Type II PRMT inhibitor is a nucleic acid (e.g., a siRNA). siRNAs against PRMT5 are described for instance in Mol Cancer Res. 2009 April; 7(4): 557-69, and Biochem J. 2012 Sep. 1; 446(2): 235-41.

In one embodiment, combinations of a Type I protein arginine methyltransferase (Type I PRMT) inhibitor and a Type II protein arginine methyltransferase (Type II PRMT) inhibitor are provided. In one aspect, the Type I PRMT inhibitor is a protein arginine methyltransferase 1 (PRMT1) inhibitor, a protein arginine methyltransferase 3 (PRMT3) inhibitor, a protein arginine methyltransferase 4 (PRMT4) inhibitor, a protein arginine methyltransferase 6 (PRMT6) inhibitor, or a protein arginine methyltransferase 8 (PRMT8) inhibitor. In one aspect, the Type II PRMT inhibitor is a protein arginine methyltransferase 5 (PRMT5) inhibitor or a protein arginine methyltransferase 9 (PRMT9) inhibitor. In another aspect, the Type I PRMT inhibitor is a compound of Formula I, II, V, or VI. In one aspect, the Type I PRMT inhibitor is Compound A. In another aspect, the Type I PRMT inhibitor is Compound D. In one aspect, the Type II PRMT inhibitor is a compound of Formula III, IV, VII, VIII, IX, X, or XI. In another aspect, the Type II PRMT inhibitor is Compound B. In one aspect, the Type II PRMT inhibitor is Compound C. In one embodiment, a combination of Compound A and Compound C is provided.

In another embodiment, methods are provided for treating cancer in a human in need thereof, the methods comprising administering to the human a combination of a Type I PRMT inhibitor and a Type II PRMT inhibitor, together with at least one of: a pharmaceutically acceptable carrier and a pharmaceutically acceptable diluent, thereby treating the cancer in the human. In one aspect, the Type I PRMT inhibitor is a protein arginine methyltransferase 1 (PRMT1) inhibitor, a protein arginine methyltransferase 3 (PRMT3) inhibitor, a protein arginine methyltransferase 4 (PRMT4) inhibitor, a protein arginine methyltransferase 6 (PRMT6) inhibitor, or a protein arginine methyltransferase 8 (PRMT8) inhibitor. In one aspect, the Type II PRMT inhibitor is a protein arginine methyltransferase 5 (PRMT5) inhibitor or a protein arginine methyltransferase 9 (PRMT9) inhibitor. In one aspect, the Type I PRMT inhibitor is a compound of Formula I, II, V, or VI. In one aspect, the Type I PRMT inhibitor is Compound A. In another aspect, the Type I PRMT inhibitor is Compound D. In one aspect, the Type II PRMT inhibitor is a compound of Formula III, IV, VII, VIII, IX, X, or XI. In another aspect, the Type II PRMT inhibitor is Compound B. In one aspect, the Type II PRMT inhibitor is Compound C. In one embodiment, methods are provided for treating cancer in a human in need thereof, the methods comprising administering to the human a combination of Compound A and Compound C, together with at least one of: a pharmaceutically acceptable carrier and a pharmaceutically acceptable diluent, thereby treating the cancer in the human.

In a further embodiment, a pharmaceutical composition comprising a therapeutically effective amount of a Type I protein arginine methyltransferase (Type I PRMT) inhibitor and a second pharmaceutical composition comprising a therapeutically effective amount of a Type II protein arginine methyltransferase (Type II PRMT) inhibitor are provided. In one aspect, the Type I PRMT inhibitor is a protein arginine methyltransferase 1 (PRMT1) inhibitor, a protein arginine methyltransferase 3 (PRMT3) inhibitor, a protein arginine methyltransferase 4 (PRMT4) inhibitor, a protein arginine methyltransferase 6 (PRMT6) inhibitor, or a protein arginine methyltransferase 8 (PRMT8) inhibitor. In one aspect, the Type II PRMT inhibitor is a protein arginine methyltransferase 5 (PRMT5) inhibitor or a protein arginine methyltransferase 9 (PRMT9) inhibitor. In another aspect, the Type I PRMT inhibitor is a compound of Formula I, II, V, or VI. In one aspect, the Type I PRMT inhibitor is Compound A. In another aspect, the Type I PRMT inhibitor is Compound D. In one aspect, the Type II PRMT inhibitor is a compound of Formula III, IV, VII, VIII, IX, X, or XI. In another aspect, the Type II PRMT inhibitor is Compound B. In one aspect, the Type II PRMT inhibitor is Compound C. In one embodiment, a pharmaceutical composition comprising a therapeutically effective amount of a Compound A and a second pharmaceutical composition comprising a therapeutically effective amount of Compound C are provided.

In another embodiment, use of a combination of a Type I PRMT inhibitor and a Type II PRMT inhibitor for the manufacture of a medicament is provided. In one embodiment, use of a combination of a Type I PRMT inhibitor and a Type II PRMT inhibitor for the treatment of cancer is provided. In one aspect, the Type I PRMT inhibitor is a protein arginine methyltransferase 1 (PRMT1) inhibitor, a protein arginine methyltransferase 3 (PRMT3) inhibitor, a protein arginine methyltransferase 4 (PRMT4) inhibitor, a protein arginine methyltransferase 6 (PRMT6) inhibitor, or a protein arginine methyltransferase 8 (PRMT8) inhibitor. In one aspect, the Type II PRMT inhibitor is a protein arginine methyltransferase 5 (PRMT5) inhibitor or a protein arginine methyltransferase 9 (PRMT9) inhibitor. In another aspect, the Type I PRMT inhibitor is a compound of Formula I, II, V, or VI. In one aspect, the Type I PRMT inhibitor is Compound A. In another aspect, the Type I PRMT inhibitor is Compound D. In one aspect, the Type II PRMT inhibitor is a compound of Formula III, IV, VII, VIII, IX, X, or XI. In another aspect, the Type II PRMT inhibitor is Compound B. In one aspect, the Type II PRMT inhibitor is Compound C. In one embodiment, a combination of Compound A and Compound C for the manufacture of a medicament is provided.

In one embodiment, a product containing containing a Type I PRMT inhibitor and a Type II PRMT inhibitor as a combined preparation for simultaneous, separate, or sequential use in medicine is provided. In one aspect, the Type I PRMT inhibitor is a protein arginine methyltransferase 1 (PRMT1) inhibitor, a protein arginine methyltransferase 3 (PRMT3) inhibitor, a protein arginine methyltransferase 4 (PRMT4) inhibitor, a protein arginine methyltransferase 6 (PRMT6) inhibitor, or a protein arginine methyltransferase 8 (PRMT8) inhibitor. In one aspect, the Type II PRMT inhibitor is a protein arginine methyltransferase 5 (PRMT5) inhibitor or a protein arginine methyltransferase 9 (PRMT9) inhibitor. In another aspect, the Type I PRMT inhibitor is a compound of Formula I, II, V, or VI. In one aspect, the Type I PRMT inhibitor is Compound A. In another aspect, the Type I PRMT inhibitor is Compound D. In one aspect, the Type II PRMT inhibitor is a compound of Formula III, IV, VII, VIII, IX, X, or XI. In another aspect, the Type II PRMT inhibitor is Compound B. In one aspect, the Type II PRMT inhibitor is Compound C. In one embodiment, a product containing containing Compound A and Compound C as a combined preparation for simultaneous, separate, or sequential use in medicine is provided.

In still another embodiment, a product containing a Type I PRMT inhibitor and a Type II PRMT inhibitor as a combined preparation for simultaneous, separate, or sequential use in treating cancer in a human subject is provided. In one aspect, the Type I PRMT inhibitor is a protein arginine methyltransferase 1 (PRMT1) inhibitor, a protein arginine methyltransferase 3 (PRMT3) inhibitor, a protein arginine methyltransferase 4 (PRMT4) inhibitor, a protein arginine methyltransferase 6 (PRMT6) inhibitor, or a protein arginine methyltransferase 8 (PRMT8) inhibitor. In one aspect, the Type II PRMT inhibitor is a protein arginine methyltransferase 5 (PRMT5) inhibitor or a protein arginine methyltransferase 9 (PRMT9) inhibitor. In another aspect, the Type I PRMT inhibitor is a compound of Formula I, II, V, or VI. In one aspect, the Type I PRMT inhibitor is Compound A. In another aspect, the Type I PRMT inhibitor is Compound D. In one aspect, the Type II PRMT inhibitor is a compound of Formula III, IV, VII, VIII, IX, X, or XI. In another aspect, the Type II PRMT inhibitor is Compound B. In one aspect, the Type II PRMT inhibitor is Compound C. In one embodiment, a product containing Compound A and Compound C as a combined preparation for simultaneous, separate, or sequential use in treating cancer in a human subject is provided.

In another embodiment, a product containing a Type I PRMT inhibitor and a Type II PRMT inhibitor as a combined preparation for simultaneous, separate, or sequential use in treating cancer in a human subject is provided, wherein the cancer is melanoma, breast cancer, lymphoma, triple negative breast cancer (TNBC), or bladder cancer. In one aspect, the Type I PRMT inhibitor is a protein arginine methyltransferase 1 (PRMT1) inhibitor, a protein arginine methyltransferase 3 (PRMT3) inhibitor, a protein arginine methyltransferase 4 (PRMT4) inhibitor, a protein arginine methyltransferase 6 (PRMT6) inhibitor, or a protein arginine methyltransferase 8 (PRMT8) inhibitor. In one aspect, the Type II PRMT inhibitor is a protein arginine methyltransferase 5 (PRMT5) inhibitor or a protein arginine methyltransferase 9 (PRMT9) inhibitor. In another aspect, the Type I PRMT inhibitor is a compound of Formula I, II, V, or VI. In one aspect, the Type I PRMT inhibitor is Compound A. In another aspect, the Type I PRMT inhibitor is Compound D. In one aspect, the Type II PRMT inhibitor is a compound of Formula III, IV, VII, VIII, IX, X, or XI. In another aspect, the Type II PRMT inhibitor is Compound B. In one aspect, the Type II PRMT inhibitor is Compound C. In one embodiment, a product containing Compound A and Compound C as a combined preparation for simultaneous, separate, or sequential use in treating cancer in a human subject is provided, wherein the cancer is melanoma, breast cancer, lymphoma, triple negative breast cancer (TNBC), or bladder cancer.

In one embodiment, methods are provided for treating cancer in a human in need thereof, the methods comprising administering to the human a therapeutically effective amount of a pharmaceutical composition comprising a Type I PRMT inhibitor and a pharmaceutical composition comprising a Type II PRMT inhibitor, thereby treating the cancer in the human. In one aspect, the Type I PRMT inhibitor is a protein arginine methyltransferase 1 (PRMT1) inhibitor, a protein arginine methyltransferase 3 (PRMT3) inhibitor, a protein arginine methyltransferase 4 (PRMT4) inhibitor, a protein arginine methyltransferase 6 (PRMT6) inhibitor, or a protein arginine methyltransferase 8 (PRMT8) inhibitor. In one aspect, the Type II PRMT inhibitor is a protein arginine methyltransferase 5 (PRMT5) inhibitor or a protein arginine methyltransferase 9 (PRMT9) inhibitor. In another aspect, the Type I PRMT inhibitor is a compound of Formula I, II, V, or VI. In one aspect, the Type I PRMT inhibitor is Compound A. In another aspect, the Type I PRMT inhibitor is Compound D. In one aspect, the Type II PRMT inhibitor is a compound of Formula III, IV, VII, VIII, IX, X, or XI. In another aspect, the Type II PRMT inhibitor is Compound B. In one aspect, the Type II PRMT inhibitor is Compound C.

In any one of the embodiments herein, the Type I PRMT inhibitor and the Type II PRMT inhibitor are administered to the patient in a route selected from: simultaneously, sequentially, in any order, systemically, orally, intravenously, and intratumorally. In one aspect, the Type I PRMT inhibitor and/or the Type II PRMT inhibitor is administered orally. In one aspect, the Type I PRMT inhibitor and the Type II PRMT inhibitor are administered in about a 1:1 ratio.

In any one of the embodiments herein, the cancer is a solid tumor or a haematological cancer. In one aspect, is melanoma, breast cancer, lymphoma, or bladder cancer.

In one aspect the cancer is selected from head and neck cancer, breast cancer, lung cancer, colon cancer, ovarian cancer, prostate cancer, gliomas, glioblastoma, astrocytomas, glioblastoma multiforme, Bannayan-Zonana syndrome, Cowden disease, Lhermitte-Duclos disease, inflammatory breast cancer, Wilm's tumor, Ewing's sarcoma, Rhabdomyosarcoma, ependymoma, medulloblastoma, kidney cancer, liver cancer, melanoma, pancreatic cancer, sarcoma, osteosarcoma, giant cell tumor of bone, thyroid cancer, lymphoblastic T cell leukemia, Chronic myelogenous leukemia, Chronic lymphocytic leukemia, Hairy-cell leukemia, acute lymphoblastic leukemia, acute myelogenous leukemia, AML, Chronic neutrophilic leukemia, Acute lymphoblastic T cell leukemia, plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), and testicular cancer.

In one aspect, the methods of the present invention further comprise administering at least one neo-plastic agent to said human.

In one aspect the human has a solid tumor. In one aspect the tumor is selected from head and neck cancer, gastric cancer, melanoma, renal cell carcinoma (RCC), esophageal cancer, non-small cell lung carcinoma, prostate cancer, colorectal cancer, ovarian cancer and pancreatic cancer. In another aspect the human has a liquid tumor such as diffuse large B cell lymphoma (DLBCL), multiple myeloma, chronic lyphomblastic leukemia (CLL), follicular lymphoma, acute myeloid leukemia and chronic myelogenous leukemia.

The present disclosure also relates to a method for treating or lessening the severity of a cancer selected from: brain (gliomas), glioblastomas, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma, Hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

By the term "treating" and grammatical variations thereof as used herein, is meant therapeutic therapy. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, or (4) to slow the progression of the condition or one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

As used herein, the terms "cancer," "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MIFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent Bcell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK)

cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenström's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

As used herein the term "Compound $A^2$" means a Type I PRMT inhibitor. In some embodiments, Compound $A^2$ is a compound of Formula I, II, V, or VI. Suitably Compound $A^2$ is Compound A.

As used herein the term "Compound $B^2$" means a Type II PRMT inhibitor. In some embodiments, Compound $B^2$ is a compound of Formula III, IV, VII, VIII, IX, X, or XI. Suitably Compound $B^2$ is Compound C.

Suitably, the combinations of this invention are administered within a "specified period".

The term "specified period" and grammatical variations thereof, as used herein, means the interval of time between the administration of one of Compound $A^2$ and Compound $B^2$ and the other of Compound $A^2$ and Compound $B^2$. Unless otherwise defined, the specified period can include simultaneous administration. Unless otherwise defined, the specified period refers to administration of Compound $A^2$ and Compound $B^2$ during a single day.

Suitably, if the compounds are administered within a "specified period" and not administered simultaneously, they are both administered within about 24 hours of each other—in this case, the specified period will be about 24 hours; suitably they will both be administered within about 12 hours of each other—in this case, the specified period will be about 12 hours; suitably they will both be administered within about 11 hours of each other—in this case, the specified period will be about 11 hours; suitably they will both be administered within about 10 hours of each other—in this case, the specified period will be about 10 hours; suitably they will both be administered within about 9 hours of each other—in this case, the specified period will be about 9 hours; suitably they will both be administered within about 8 hours of each other—in this case, the specified period will be about 8 hours; suitably they will both be administered within about 7 hours of each other—in this case, the specified period will be about 7 hours; suitably they will both be administered within about 6 hours of each other—in this case, the specified period will be about 6 hours; suitably they will both be administered within about 5 hours of each other—in this case, the specified period will be about 5 hours; suitably they will both be administered within about 4 hours of each other—in this case, the specified period will be about 4 hours; suitably they will both be administered within about 3 hours of each other—in this case, the specified period will be about 3 hours; suitably they will both be administered within about 2 hours of each other—in this case, the specified period will be about 2 hours; suitably they will both be administered within about 1 hour of each other—in this case, the specified period will be about 1 hour. As used herein, the administration of Compound $A^2$ and Compound $B^2$ in less than about 45 minutes apart is considered simultaneous administration.

Suitably, when the combination of the invention is administered for a "specified period", the compounds will be co-administered for a "duration of time".

The term "duration of time" and grammatical variations thereof, as used herein means that both compounds of the invention are administered for an indicated number of consecutive days. Unless otherwise defined, the number of consecutive days does not have to commence with the start of treatment or terminate with the end of treatment, it is only required that the number of consecutive days occur at some point during the course of treatment.

Regarding "specified period" administration:

Suitably, both compounds will be administered within a specified period for at least one day—in this case, the duration of time will be at least one day; suitably, during the course to treatment, both compounds will be administered within a specified period for at least 3 consecutive days—in this case, the duration of time will be at least 3 days; suitably, during the course to treatment, both compounds will be administered within a specified period for at least 5 consecutive days—in this case, the duration of time will be at least 5 days; suitably, during the course to treatment, both compounds will be administered within a specified period for at least 7 consecutive days—in this case, the duration of time will be at least 7 days; suitably, during the course to treatment, both compounds will be administered within a specified period for at least 14 consecutive days—in this case, the duration of time will be at least 14 days; suitably, during the course to treatment, both compounds will be administered within a specified period for at least 30 consecutive days—in this case, the duration of time will be at least 30 days.

Suitably, if the compounds are not administered during a "specified period", they are administered sequentially. By the term "sequential administration", and grammatical derivates thereof, as used herein is meant that one of Compound $A^2$ and Compound $B^2$ is administered once a day for two or more consecutive days and the other of Compound $A^2$ and Compound $B^2$ is subsequently administered once a day for two or more consecutive days. Also, contemplated herein is a drug holiday utilized between the sequential administration of one of Compound $A^2$ and Compound $B^2$ and the other of Compound $A^2$ and Compound $B^2$. As used herein, a drug holiday is a period of days after the sequential administration of one of Compound $A^2$ and Compound $B^2$ and before the administration of the other of Compound $A^2$ and Compound $B^2$ where neither Compound $A^2$ nor Compound $B^2$ is administered. Suitably the drug holiday will be a period of days selected from: 1 day, 2 days, 3 days, 4 days, 5 days, 6 days, 7 days, 8 days, 9 days, 10 days, 11 days, 12 days, 13 days and 14 days.

Regarding Sequential Administration:

Suitably, one of Compound $A^2$ and Compound $B^2$ is administered for from 1 to 30 consecutive days, followed by an optional drug holiday, followed by administration of the other of Compound $A^2$ and Compound $B^2$ for from 1 to 30 consecutive days. Suitably, one of Compound $A^2$ and Compound $B^2$ is administered for from 1 to 21 consecutive days, followed by an optional drug holiday, followed by administration of the other of Compound $A^2$ and Compound $B^2$ for from 1 to 21 consecutive days. Suitably, one of Compound $A^2$ and Compound $B^2$ is administered for from 1 to 14 consecutive days, followed by a drug holiday of from 1 to 14 days, followed by administration of the other of Compound $A^2$ and Compound $B^2$ for from 1 to 14 consecutive days. Suitably, one of Compound $A^2$ and Compound $B^2$ is administered for from 1 to 7 consecutive days, followed by a drug holiday of from 1 to 10 days, followed by administration of the other of Compound $A^2$ and Compound $B^2$ for from 1 to 7 consecutive days.

Suitably, Compound $B^2$ will be administered first in the sequence, followed by an optional drug holiday, followed by administration of Compound $A^2$. Suitably, Compound $B^2$ is administered for from 3 to 21 consecutive days, followed by an optional drug holiday, followed by administration of Compound $A^2$ for from 3 to 21 consecutive days. Suitably, Compound $B^2$ is administered for from 3 to 21 consecutive days, followed by a drug holiday of from 1 to 14 days, followed by administration of Compound $A^2$ for from 3 to 21 consecutive days. Suitably, Compound $B^2$ is administered for from 3 to 21 consecutive days, followed by a drug holiday of from 3 to 14 days, followed by administration of Compound $A^2$ for from 3 to 21 consecutive days. Suitably, Compound $B^2$ is administered for 21 consecutive days, followed by an optional drug holiday, followed by administration of Compound $A^2$ for 14 consecutive days. Suitably, Compound $B^2$ is administered for 14 consecutive days, followed by a drug holiday of from 1 to 14 days, followed by administration of Compound $A^2$ for 14 consecutive days. Suitably, Compound $B^2$ is administered for 7 consecutive days, followed by a drug holiday of from 3 to 10 days, followed by administration of Compound $A^2$ for 7 consecutive days. Suitably, Compound $B^2$ is administered for 3 consecutive days, followed by a drug holiday of from 3 to 14 days, followed by administration of Compound $A^2$ for 7 consecutive days. Suitably, Compound $B^2$ is administered for 3 consecutive days, followed by a drug holiday of from 3 to 10 days, followed by administration of Compound $A^2$ for 3 consecutive days.

It is understood that a "specified period" administration and a "sequential" administration can be followed by repeat dosing or can be followed by an alternate dosing protocol, and a drug holiday may precede the repeat dosing or alternate dosing protocol.

The methods of the present invention may also be employed with other therapeutic methods of cancer treatment.

Compound $A^2$ and Compound $B^2$ may be administered by any appropriate route. Suitable routes include oral, rectal, nasal, topical (including buccal and sublingual), intratumorally, vaginal, and parenteral (including subcutaneous, intramuscular, intravenous, intradermal, intrathecal, and epidural). It will be appreciated that the preferred route may vary with, for example, the condition of the recipient of the combination and the cancer to be treated. It will also be appreciated that each of the agents administered may be administered by the same or different routes and that Compound $A^2$ and Compound $B^2$ may be compounded together in a pharmaceutical composition/formulation.

In one embodiment, one or more components of a combination of the invention are administered intravenously. In one embodiment, one or more components of a combination of the invention are administered orally. In another embodiment, one or more components of a combination of the invention are administered intratumorally. In another embodiment, one or more components of a combination of the invention are administered systemically, e.g., intravenously, and one or more other components of a combination of the invention are administered intratumorally. In any of the embodiments, e.g., in this paragraph, the components of the invention are administered as one or more pharmaceutical compositions.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita, T. S. Lawrence, and S. A. Rosenberg (editors), $10^{th}$ edition (Dec. 5, 2014), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule or anti-mitotic agents such as diterpenoids and *vinca* alkaloids; platinum coordination complexes; alkylating agents such as nitrogen mustards, oxazaphosphorines, alkylsulfonates, nitrosoureas, and triazenes; antibiotic agents such as actinomycins, anthracyclins, and bleomycins; topoisomerase I inhibitors such as camptothecins; topoisomerase II inhibitors such as epipodophyllotoxins; antimetabolites such as purine and pyrimidine analogues and anti-folate compounds; hormones and hormonal analogues; signal transduction pathway inhibitors; non-receptor tyrosine kinase angiogenesis inhibitors; immunotherapeutic agents; proapoptotic agents; cell cycle signalling inhibitors; proteasome inhibitors; heat shock protein inhibitors; inhibitors of cancer metabolism; and cancer gene therapy agents such as genetically modified T cells.

Examples of a further active ingredient or ingredients for use in combination or co-administered with the present methods or combinations are anti-neoplastic agents. Examples of anti-neoplastic agents include, but are not limited to, chemotherapeutic agents; immuno-modulatory agents; immune-modulators; and immunostimulatory adjuvants.

EXAMPLES

The following examples illustrate various non-limiting aspects of this invention.

Example 1

Arginine Methylation and PRMTs

Arginine methylation is an important post-translational modification on proteins involved in a diverse range of cellular processes such as gene regulation, RNA processing, DNA damage response, and signal transduction. Proteins containing methylated arginines are present in both nuclear and cytosolic fractions suggesting that the enzymes that catalyze the transfer of methyl groups on to arginines are also present throughout these subcellular compartments (reviewed in Yang, Y. & Bedford, M. T. Protein arginine methyltransferases and cancer. *Nat Rev Cancer* 13, 37-50, doi:10.1038/nrc3409 (2013); Lee, Y. H. & Stallcup, M. R. Minireview: protein arginine methylation of nonhistone proteins in transcriptional regulation. *Mol Endocrinol* 23, 425-433, doi:10.1210/me.2008-0380 (2009)). In mammalian cells, methylated arginine exists in three major forms:

ω—N$^G$-monomethyl-arginine (MMA), ω—N$^G$,N$^G$-asymmetric dimethyl arginine (ADMA), or ω—N$^G$,N'$^G$-symmetric dimethyl arginine (SDMA). Each methylation state can affect protein-protein interactions in different ways and therefore has the potential to confer distinct functional consequences for the biological activity of the substrate (Yang, Y. & Bedford, M. T. Protein arginine methyltransferases and cancer. *Nat Rev Cancer* 13, 37-50, doi:10.1038/nrc3409 (2013)).

Arginine methylation occurs largely in the context of glycine-, arginine-rich (GAR) motifs through the activity of a family of Protein Arginine Methyltransferases (PRMTs) that transfer the methyl group from S-adenosyl-L-methionine (SAM) to the substrate arginine side chain producing S-adenosyl-homocysteine (SAH) and methylated arginine (FIG. 1). This family of proteins is comprised of 10 members of which 9 have been shown to have enzymatic activity (Bedford, M. T. & Clarke, S. G. Protein arginine methylation in mammals: who, what, and why. *Mol Cell* 33, 1-13, doi:10.1016/j.molcel.2008.12.013 (2009)). The PRMT family is categorized into four sub-types (Type I-IV) depending on the product of the enzymatic reaction (FIG. 1). Type IV enzymes methylate the internal guanidino nitrogen and have only been described in yeast (Fisk, J. C. & Read, L. K. Protein arginine methylation in parasitic protozoa. *Eukaryot Cell* 10, 1013-1022, doi:10.1128/EC.05103-11 (2011)); types I-III enzymes generate monomethyl-arginine (MMA, Rme1) through a single methylation event. The MMA intermediate is considered a relatively low abundance intermediate, however, select substrates of the primarily Type III activity of PRMT7 can remain monomethylated, while Types I and II enzymes catalyze progression from MMA to either asymmetric dimethyl-arginine (ADMA, Rme2a) or symmetric dimethyl arginine (SDMA, Rme2s) respectively. Type II PRMTs include PRMT5, and PRMT9, however, PRMT5 is the primary enzyme responsible for formation of symmetric dimethylation. Type I enzymes include PRMT1, PRMT3, PRMT4, PRMT6 and PRMT8. PRMT1, PRMT3, PRMT4, and PRMT6 are ubiquitously expressed while PRMT8 is largely restricted to the brain (reviewed in Bedford, M. T. & Clarke, S. G. Protein arginine methylation in mammals: who, what, and why. Mol Cell 33, 1-13, doi: 10.1016/j.molcel.2008.12.013 (2009)).

PRMT1 is the primary Type 1 enzyme capable of catalyzing the formation of MMA and ADMA on numerous cellular substrates (Bedford, M. T. & Clarke, S. G. Protein arginine methylation in mammals: who, what, and why. *Mol Cell* 33, 1-13, doi:10.1016/j.molcel.2008.12.013 (2009)). In many instances, the PRMT1-dependent ADMA modification is required for the biological activity and trafficking of its substrates (Nicholson, T. B., Chen, T. & Richard, S. The physiological and pathophysiological role of PRMT1-mediated protein arginine methylation. *Pharmacol Res* 60, 466-474, doi:10.1016/j.phrs.2009.07.006 (2009)), and the activity of PRMT1 accounts for ~85% of cellular ADMA levels (Dhar, S. et al. Loss of the major Type I arginine methyltransferase PRMT1 causes substrate scavenging by other PRMTs. *Sci Rep* 3, 1311, doi:10.1038/srep01311 (2013); Pawlak, M. R., Scherer, C. A., Chen, J., Roshon, M. J. & Ruley, H. E. Arginine N-methyltransferase 1 is required for early postimplantation mouse development, but cells deficient in the enzyme are viable. *Mol Cell Biol* 20, 4859-4869 (2000)). Complete knockout of PRMT1 results in a profound increase in MMA across numerous substrates suggesting that the major biological function for PRMT1 is to convert MMA to ADMA while other PRMTs can establish and maintain MMA (Dhar, S. et al. Loss of the major Type I arginine methyltransferase PRMT1 causes substrate scavenging by other PRMTs. *Sci Rep* 3, 1311, doi:10.1038/srep01311 (2013)). In addition, SDMA levels are increased upon loss of PRMT1, likely a consequence of the loss of ADMA and the corresponding increase of MMA that can serve as the substrate for SDMA-generating Type II PRMTs. Inhibition of Type I PRMTs may lead to altered substrate function through loss of ADMA, increase in MMA, or, alternatively, a switch to the distinct methylation pattern associated with SDMA (Dhar, S. et al. Loss of the major Type I arginine methyltransferase PRMT1 causes substrate scavenging by other PRMTs. *Sci Rep* 3, 1311, doi:10.1038/srep01311 (2013)).

Disruption of the Prmt1 locus in mice results in early embryonic lethality and homozygous embryos fail to develop beyond E6.5 indicating a requirement for PRMT1 in normal development (Pawlak, M. R., Scherer, C. A., Chen, J., Roshon, M. J. & Ruley, H. E. Arginine N-methyltransferase 1 is required for early postimplantation mouse development, but cells deficient in the enzyme are viable. *Mol Cell Biol* 20, 4859-4869 (2000); Yu, Z., Chen, T., Hebert, J., Li, E. & Richard, S. A mouse PRMT1 null allele defines an essential role for arginine methylation in genome maintenance and cell proliferation. *Mol Cell Biol* 29, 2982-2996, doi:10.1128/MCB.00042-09 (2009)). Conditional or tissue specific knockout will be required to better understand the role for PRMT1 in the adult. Mouse embryonic fibroblasts derived from Prmt1 null mice undergo growth arrest, polyploidy, chromosomal instability, and spontaneous DNA damage in association with hypomethylation of the DNA damage response protein MRE11, suggesting a role for PRMT1 in genome maintenance and cell proliferation (Yu, Z., Chen, T., Hebert, J., Li, E. & Richard, S. A mouse PRMT1 null allele defines an essential role for arginine methylation in genome maintenance and cell proliferation. *Mol Cell Biol* 29, 2982-2996, doi:10.1128/MCB.00042-09 (2009)). PRMT1 protein and mRNA can be detected in a wide range of embryonic and adult tissues, consistent with its function as the enzyme responsible for the majority of cellular arginine methylation. Although PRMTs can undergo post-translational modifications themselves and are associated with interacting regulatory proteins, PRMT1 retains basal activity without a requirement for additional modification (reviewed in Yang, Y. & Bedford, M. T. Protein arginine methyltransferases and cancer. *Nat Rev Cancer* 13, 37-50, doi:10.1038/nrc3409 (2013)).

PRMT1 and Cancer

Figure 2:
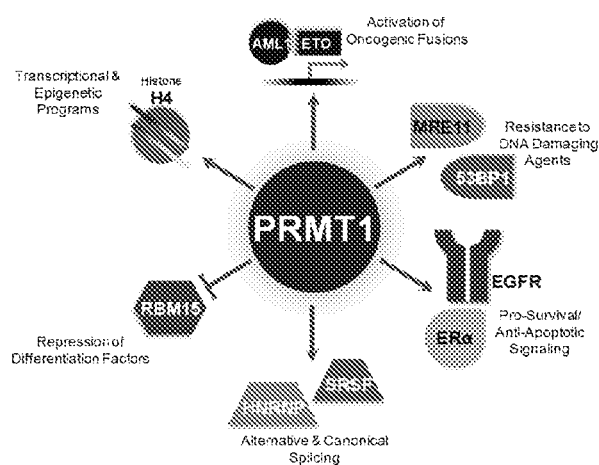
FIG. 2: Functional classes of cancer relevant PRMT1 substrates. Known substrates of PRMT1 and their association to cancer related biology (Yang, Y. & Bedford, M. T. Protein arginine methyltransferases and cancer. Nat Rev Cancer 13, 37-50, doi:10.1038/nrc3409 (2013); Shia, W. J. et al. PRMT1 interacts with AML1-ETO to promote its transcriptional activation and progenitor cell proliferative potential. Blood 119, 4953-4962, doi:10.1182/blood-2011-04-347476 (2012); Wei, H., Mundade, R., Lange, K. C. & Lu, T. Protein arginine methylation of non-histone proteins and its role in diseases. Cell Cycle 13, 32-41, doi:10.4161/cc.27353 (2014); Boisvert, F. M., Rhie, A., Richard, S. & Doherty, A. J. The GAR motif of 53BP1 is arginine methylated by PRMT1 and is necessary for 53BP1 DNA binding activity. Cell Cycle 4, 1834-1841, doi:10.4161/cc.4.12.2250 (2005); Boisvert, F. M., Dery, U., Masson, J. Y. & Richard, S. Arginine methylation of MRE11 by PRMT1 is required for DNA damage checkpoint control. Genes Dev 19, 671-676, doi:10.1101/gad.1279805 (2005); Zhang, L. et al. Cross-talk between PRMT1-mediated methylation and ubiquitylation on RBM15 controls RNA splicing. Elife 4, doi: 10.7554/eLife.07938 (2015); Snijders, A. P. et al. Arginine methylation and citrullination of splicing factor proline- and glutamine-rich (SFPQ/PSF) regulates its association with mRNA. RNA 21, 347-359, doi:10.1261/rna.045138.114 (2015); Liao, H. W. et al. PRMT1-mediated methylation of the EGF receptor regulates signaling and cetuximab response. J Clin Invest 125, 4529-4543, doi:10.1172/JC182826 (2015); Ng, R. K. et al. Epigenetic dysregulation of leukaemic HOX code in MLL-rearranged leukaemia mouse model. J Pathol 232, 65-74, doi:10.1002/path.4279 (2014); Bressan, G. C. et al. Arginine methylation analysis of the splicing-associated SR protein SFRS9/SRP30C. Cell Mol Biol Lett 14, 657-669, doi:10.2478/s1658-009-0024-2 (2009)).

Mis-regulation and overexpression of PRMT1 has been associated with a number of solid and hematopoietic cancers (Yang, Y. & Bedford, M. T. Protein arginine methyltransferases and cancer. *Nat Rev Cancer* 13, 37-50, doi:10.1038/nrc3409 (2013); Yoshimatsu, M. et al. Dysregulation of PRMT1 and PRMT6, Type I arginine methyltransferases, is involved in various types of human cancers. *Int J Cancer* 128, 562-573, doi:10.1002/ijc.25366 (2011)). The link between PRMT1 and cancer biology has largely been through regulation of methylation of arginine residues found on relevant substrates (FIG. 2). In several tumor types, PRMT1 can drive expression of aberrant oncogenic programs through methylation of histone H4 (Takai, H. et al. 5-Hydroxymethylcytosine plays a critical role in glioblastomagenesis by recruiting the CHTOP-methylosome complex. *Cell Rep* 9, 48-60, doi:10.1016/j.celrep.2014.08.071 (2014); Shia, W. J. et al. PRMT1 interacts with AML1-ETO to promote its transcriptional activation and progenitor cell proliferative potential. *Blood* 119, 4953-4962, doi:10.1182/blood-2011-04-347476 (2012); Zhao, X. et al. Methylation of RUNX1 by PRMT1 abrogates SIN3A binding and potentiates its transcriptional activity. *Genes Dev* 22, 640-653, doi:10.1101/gad.1632608 (2008)), as well as through its activity on non-histone substrates (Wei, H., Mundade, R., Lange, K. C. & Lu, T. Protein arginine methylation of non-histone proteins and its role in diseases. *Cell Cycle* 13, 32-41, doi:10.4161/cc.27353 (2014)). In many of these experimental systems, disruption of the PRMT1-dependent ADMA modification of its substrates decreases the proliferative capacity of cancer cells (Yang, Y. & Bedford, M. T. Protein arginine methyltransferases and cancer. *Nat Rev Cancer* 13, 37-50, doi:10.1038/nrc3409 (2013)).

Several studies have linked PRMT1 to the development of hematological and solid tumors. PRMT1 is associated with leukemia development through methylation of key drivers such as MLL and AML1-ETO fusions, leading to activation of oncogenic pathways (Shia, W. J. et al.). PRMT1 interacts with AML1-ETO to promote its transcriptional activation and progenitor cell proliferative potential. *Blood* 119, 4953-4962, doi:10.1182/blood-2011-04-347476 (2012); Cheung, N. et al. Targeting Aberrant Epigenetic Networks Mediated by PRMT1 and KDM4C in Acute Myeloid Leukemia. *Cancer Cell* 29, 32-48, doi:10.1016/j.ccell.2015.12.007 (2016)). Knockdown of PRMT1 in bone marrow cells derived from AML1-ETO expressing mice suppressed clonogenicity, demonstrating a critical requirement for PRMT1 in maintaining the leukemic phenotype of this model (Shia, W. J. et al. PRMT interacts with AML1-ETO to promote its transcriptional activation and progenitor cell proliferative potential. *Blood* 119, 4953-4962, doi:10.1182/blood-2011-04-347476 (2012)). PRMT1 is also a component of MLL fusion complexes, promotes aberrant transcriptional activation in association with H4R3 methylation, and knockdown of PRMT1 can suppress MLL-EEN mediated transformation of hematopoietic stem cells (Cheung, N., Chan, L. C., Thompson, A., Cleary, M. L. & So, C. W. Protein argininemethyltransferase-dependent oncogenesis. *Nat Cell Biol* 9, 1208-1215, doi:10.1038/ncb1642 (2007)). In breast cancer patients, high expression of PRMT1 was found to correlate with shorter disease free survival and with tumors of advanced histological grade (Mathioudaki, K. et al. Clinical evaluation of PRMT1 gene expression in breast cancer. *Tumour Biol* 32, 575-582, doi:10.1007/s13277-010-0153-2 (2011)). To this end, PRMT1 has been implicated in the promotion of metastasis and cancer cell invasion (Gao, Y. et al. The dual function of PRMT1 in modulating epithelial-mesenchymal transition and cellular senescence in breast cancer cells through regulation of ZEB1. *Sci Rep* 6, 19874, doi:10.1038/srep19874 (2016); Avasarala, S. et al. PRMT1 Is a Novel Regulator of Epithelial-Mesenchymal-Transition in Non-small Cell Lung Cancer. *J Biol Chem* 290, 13479-13489, doi:10.1074/jbc.M114.636050 (2015)) and PRMT1 mediated methylation of Estrogen Receptor a (ERa) can potentiate growth-promoting signal transduction pathways. This methylation driven mechanism may provide a growth advantage to breast cancer cells even in the presence of anti-estrogens (Le Romancer, M. et al. Regulation of estrogen rapid signaling through arginine methylationby PRMT1. *Mol Cell* 31, 212-221, doi:10.1016/j.molcel.2008.05.025 (2008)). In addition, PRMT1 promotes genome stability and resistance to DNA damaging agents through regulating both homologous recombination and non-homologous end-joining DNA repair pathways (Boisvert, F. M., Rhie, A., Richard, S. & Doherty, A. J. The GAR motif of 53BP1 is arginine methylated by PRMT1 and is necessary for 53BP1 DNA binding activity. *Cell Cycle* 4, 1834-1841, doi:10.4161/cc.4.12.2250 (2005); Boisvert, F. M., Dery, U., Masson, J. Y. & Richard, S. Arginine methylation of MRE11 by PRMT1 is required for DNA damage checkpoint control. *Genes Dev* 19, 671-676, doi:10.1101/gad.1279805 (2005)). Therefore, inhibition of PRMT1 may sensitize cancers to DNA damaging agents, particularly in tumors where DNA repair machinery may be compromised by mutations (such as BRCA1 in breast cancers) (O'Donovan, P. J. & Livingston, D. M. BRCA1 and BRCA2: breast/ovarian cancer susceptibility gene products and participants in DNA double-strand break repair. *Carcinogenesis* 31, 961-967, doi:10.1093/carcin/bgq069 (2010)). Together, these observations demonstrate key roles for PRMT1 in clinically-relevant aspects of tumor biology, and suggest a rationale for exploring combinations with therapies such as those that promote DNA damage.

Figure 3:
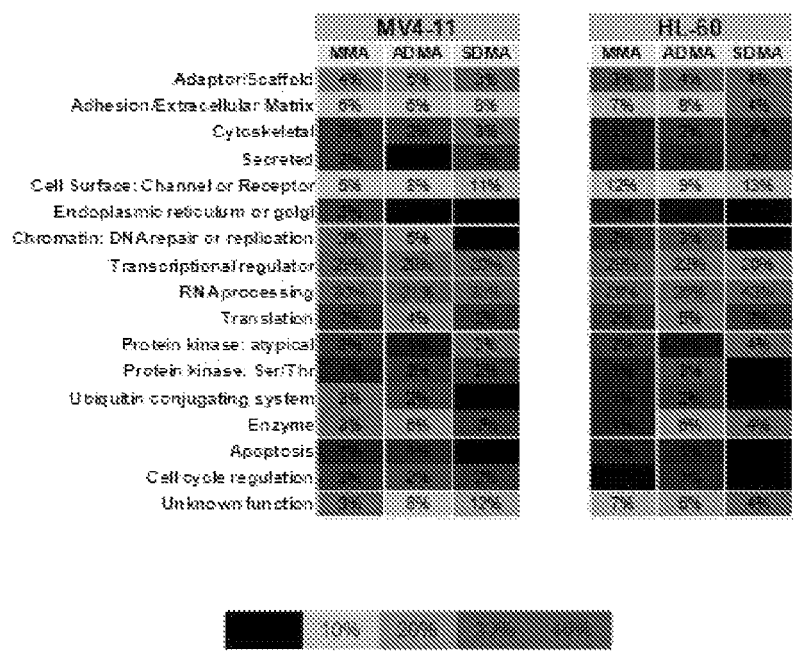
FIG. 3: Methylscan evaluation of cell lines treated with Compound D. Percent of proteins with methylation changes (independent of directionality of change) are categorized by functional group as indicated.

RNA binding proteins and splicing machinery are a major class of PRMT1 substrates and have been implicated in cancer biology through their biological function as well as recurrent mutations in leukemias (Bressan, G. C. et al. Arginine methylation analysis of the splicing-associated SR protein SFRS9/SRP30C. *Cell Mol Biol Lett* 14, 657-669, doi:10.2478/s1658-009-0024-2 (2009); Sveen, A., Kilpinen, S., Ruusulehto, A., Lothe, R. A. & Skotheim, R. I. Aberrant RNA splicing in cancer; expression changes and driver mutations of splicing factor genes. *Oncogene* 35, 2413-2427, doi:10.1038/onc.2015.318 (2016); Hsu, T. Y. et al. The spliceosome is a therapeutic vulnerability in MYC-driven cancer. *Nature* 525, 384-388, doi:10.1038/nature14985 (2015)). Ina recent study, PRMT1 was shown to methylate the RNA binding protein, RBM15, in acute megakaryocytic leukemia (Zhang, L. et al. Cross-talk between PRMT1-mediated methylation and ubiquitylation on RBM15 controls RNA splicing. *Elife* 4, doi:10.7554/eLife.07938 (2015)). PRMT1 mediated methylation of RBM15 regulates its expression; consequently, overexpression of PRMT1 in AML cell lines was shown to block differentiation by downregulation of RBM15, thereby preventing its ability to bind pre-mRNA intronic regions of genes important for differentiation. To identify putative PRMT1 substrates, a proteomic approach (Methylscan, Cell Signaling Technology) was utilized to identify proteins with changes in arginine methylation states in response to a tool PRMT1 inhibitor, Compound D. Protein fragments from Compound D- and DSMO-treated cell extracts were immunoprecipitated using methyl arginine specific antibodies (ADMA, MMA, SDMA), and peptides were identified by mass spectrometry. While many proteins undergo changes in arginine methylation, the majority of substrates identified were transcriptional regulators and RNA processing proteins in AML cell lines treated with the tool compound (FIG. 3).

In summary, the impact of PRMT1 on cancer relevant pathways suggests inhibition may lead to anti-tumor activity, providing a novel therapeutic mechanism for the treatment of AML, lymphoma, and solid tumor indications. As described in the emerging literature, several mechanisms support a rationale for the use of a PRMT1 inhibitor in hematological and solid tumors including: inhibition of AML-ETO driven oncogenesis in leukemia, inhibition of growth promoting signal transduction in breast cancer, and modulation of splicing through methylation of RNA binding proteins and spliceosome machinery. Inhibition of Type I PRMTs including PRMT1 represents a tractable strategy to suppress aberrant cancer cell proliferation and survival.

Biochemistry

Detailed in vitro biochemical studies were conducted with Compound A to characterize the potency and mechanism of inhibition against Type I PRMTs.

Mechanism of Inhibition

The inhibitory mechanism of Compound A for PRMT1 was explored through substrate competition experiments. Inhibitor modality was examined by plotting Compound A $IC_{50}$ values as a function of substrate concentration divided by its $K_m^{app}$ and comparing the resulting plots to the Cheng-Prusoff relationship for competitive, non-competitive, and uncompetitive inhibition (Copeland, R. A. Evaluation of enzyme inhibitors in drug discovery. A guide for medicinal chemists and pharmacologists. *Methods Biochem Anal* 46, 1-265 (2005)). Compound A $IC_{50}$ values decreased with increasing SAM concentration indicating that inhibition of PRMT1 by Compound A was uncompetitive with respect to SAM with a $K_i^{app}$ value of 15 nM when fit to an equation for uncompetitive inhibition (FIG. 4A). No clear modality trend was observed when Compound A $IC_{50}$ values were plotted as a function of H4 1-21 peptide (FIG. 4B) suggesting mixed type inhibition. Further analysis was performed using a global analysis resulting in an a value of 3.7 confirming the peptide mechanism as mixed and yielding a $K_i^{app}$ value of 19 nM (FIG. 4B, inset).

Time Dependence and Reversibility

Figure 5:
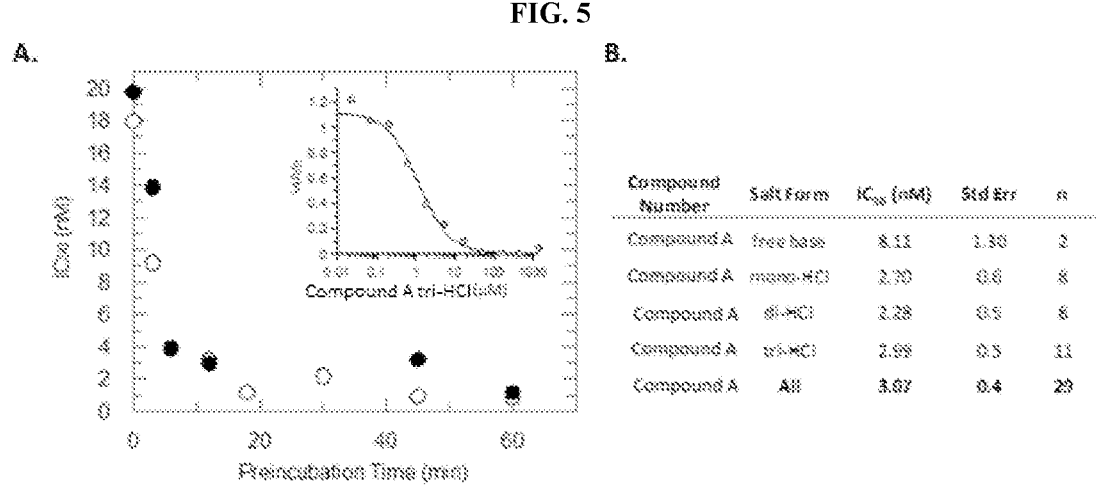
FIG. 5: Potency of Compound A against PRMT1. PRMT1 activity was monitored using a radioactive assay run under balanced conditions (substrate concentrations equal to $K_{ma}pp$) measuring transfer of $^3H$ from SAM to a H4 1-21 peptide. $IC_{50}$ values were determined by fitting the data to a 3-parameter dose-response equation. (A) $IC_{50}$ values plotted as a function of PRMT1:SAM:Compound A-tri-HCl preincubation time. Open and filled circles represent two independent experiments (0.5 nM PRMT1). Inset shows a representative $IC_{50}$ curve for Compound A-tri-HCl inhibition of PRMT1 activity following a 60 minute PRMT1:SAM:Compound A-tri-HCl preincubation. (B) Compound A inhibition of PRMT1 categorized by salt form. $IC_{50}$ values were determined following a 60 minute PRMT1:SAM:Compound A preincubation and a 20 minute reaction.

Compound A was evaluated for time dependent inhibition by measuring $IC_{50}$ values following varying SAM:PRMT1:Compound A preincubation time and a 20 minute reaction. An inhibitory mechanism that is uncompetitive with SAM implies that generation of the SAM:PRMT1 complex is required to support binding of Compound A, therefore SAM (held at $K_m^{app}$) was included during the preincubation. Compound A demonstrated time dependent inhibition of PRMT1 methylation evident by an increase in potency with longer preincubation time (FIG. 5A). Since time dependent inhibition was observed, further $IC_{50}$ determinations included a 60 minute SAM:PRMT1:Compound A preincubation and a 40 minute reaction time to provide a better representation of compound potency. These conditions yield an $IC_{50}$ of 3.1±0.4 nM (n=29) that is >10-fold above the theoretical tight-binding limit (0.25 nM) of the assay. Examining $IC_{50}$ values at varying PRMT1 concentrations revealed that the actual tight binding limit would be significantly lower than 0.25 nM potentially due to a low active fraction (FIG. 5B). The salt form of Compound A did not significantly affect the $IC_{50}$ value determined against PRMT1 (FIG. 5B).

Two explanations for time dependent inhibition are slow-binding reversible inhibition and irreversible inhibition. To distinguish between these two mechanisms, affinity selection mass spectrometry (ASMS) was used to examine the binding of Compound A to PRMT1. ASMS first separates bound from unbound ligand, and then detects reversibly bound ligand by MS. A 2 hr preincubation of PRMT1:SAM with Compound A was used to ensure that the time dependent complex (ESI*) was fully formed based on the profile shown in FIG. 5A) in which maximal potency was observed after 20 minutes of preincubation. Under these conditions, Compound A was detectable using ASMS. This suggests that the primary mechanism is reversible in nature, since ASMS would be unable to detect irreversibly bound Compound A. Definitive reversibility studies including off-rate analysis have not yet been performed and would further validate the mechanism.

Crystallography

Figure 6:
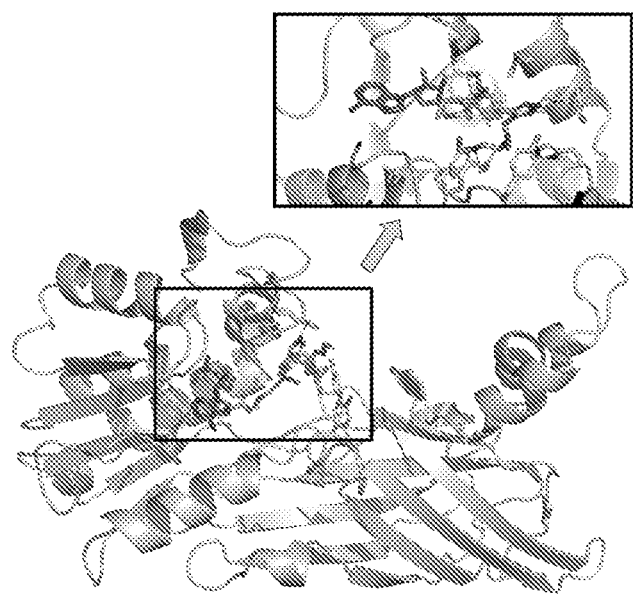
FIG. 6: The crystal structure resolved at 2.48 for PRMT1 in complex with Compound A (orange) and SAH (purple). The inset reveals that the compound is bound in the peptide binding pocket and makes key interactions with PRMT1 sidechains.

To determine inhibitor binding mode, the co-crystal structure of Compound A bound to PRMT1 and SAH was determined (2.48 Å resolution) (FIG. 6). SAH is the product formed upon removal of the methyl group from SAM by PRMT1; therefore, SAH and SAM should similarly occupy the same pocket of PRMT1. The inhibitor binds in the cleft normally occupied by the substrate peptide directly adjacent to the SAH pocket and its diamine sidechain occupies the putative arginine substrate site. The terminal methylamine forms a hydrogen bond with the Glu62 sidechain residue that is 3.6 Å from the thioether of SAH and the SAH binding pocket is bridged to Compound A by Tyr57 and Met66. Compound A binds PRMT1 through the formation of a hydrogen bond between the proton of the pyrazole nitrogen of Compound A and the acidic sidechain of Glu65; the diethoxy branched cyclohexyl moiety lies along the solvent exposed surface in a hydrophobic groove formed by Tyr57, Ile62, Tyr166 and Tyr170. The spatial separation between SAH and inhibitor binding, as well as interactions with residues such as Tyr57 could support the SAM uncompetitive mechanism revealed in the enzymatic studies. The finding that Compound A is bound in the substrate peptide pocket and that the diamine sidechain may mimic the amines of the substrate arginine residue implies that inhibitor modality may be competitive with peptide. Biochemical mode of inhibition studies support that Compound A is a mixed inhibitor with respect to peptide (FIG. 4B). The time-dependent behavior of Compound A as well as the potential for exosite binding of the substrate peptide outside of the peptide cleft could both result in a mode of inhibition that is not competitive with peptide, explaining the difference in modality suggested by the structural and biochemical studies.

Orthologs

To facilitate interpretation of toxicology studies, the potency of Compound A was evaluated against the rat and dog orthologs of PRMT1. As with human PRMT1, Compound A revealed time dependent inhibition against rat and dog PRMT1 with $IC_{50}$ values decreasing with increasing preincubation (FIG. 7A). Additionally, no shift in Compound A potency was observed across a range of enzyme concentrations (0.25-32 nM) suggesting the $IC_{50}$ values measured did not approach the tight-binding limit of the assay for human, rat or dog (FIG. 7B). $IC_{50}$ values were determined using conditions equivalent to those used to assess human PRMT1 and revealed that Compound A potency varied<2-fold across all species (FIG. 7C).

Selectivity

Figure 8:
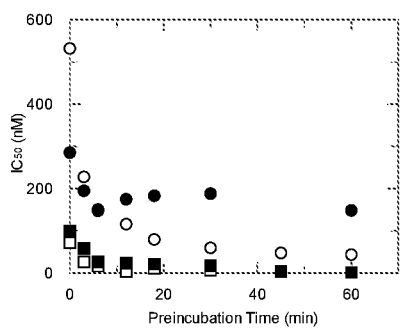
FIG. 8: Potency of Compound A against PRMT family members. PRMT activity was monitored using a radioactive assay run under balanced conditions (substrate concentrations at $K_m^{app}$) following a 60 minute PRMT:SAM:Compound A preincubation. $IC_{50}$ values for Compound A were determined by fitting data to a 3-parameter dose-response equation. (A) Data is an average from testing multiple salt forms of Compound A. $K_i^{*app}$ value were calculated based on the equation $K_i=IC_{50}/(1+(K_m/[S]))$ for an uncompetitive inhibitor and the assumption that the $IC_{50}$ determination was representative of the ESI* conformation. (B) $IC_{50}$ values plotted as a function of PRMT3 (●), PRMT4 (○), PRMT6 (■) or PRMT8 (□):SAM:Compound A preincubation time.

The selectivity of Compound A was assessed across a panel of PRMT family members. $IC_{50}$ values were determined against representative Types I (PRMT3, PRMT4, PRMT6 and PRMT8) and II (PRMT5/MEP50 and PRMT9) family members following a 60 minute SAM:Enzyme:Compound A preincubation. Compound A inhibited the activity of all Type I PRMTs tested with varying potencies, but failed to inhibit Type II family members (FIG. 8A). Additional characterization of the Type I PRMTs revealed that Compound A was a time dependent inhibitor of PRMT4, PRMT6 and PRMT8 due to the increase in potency observed following increasing Enzyme:SAM:Compound A preincubation times; whereas, PRMT3 displayed no time dependent behavior (FIG. 8B).

To further characterize selectivity of Compound A, the inhibition of twenty-one methyltransferases was evaluated at a single concentration of Compound A (10 μM, Reaction Biology). The highest degree of inhibition, 18%, was observed against PRDM9. Overall, Compound A showed minimal inhibition of the methyltransferases tested suggesting it is a selective inhibitor of Type I PRMTs (Table 1). Additional selectivity assays are described in the Safety sections.

TABLE 1

Methyltransferases tested for inhibition by Compound A. Enzymes were assayed at a fixed concentration of SAM (1 µM) independent of the SAM Km value.

| Methyltransferase | Substrate | Average % Inhibition |
| --- | --- | --- |
| PRDM9 | Histone H3 | 17.99 |
| NSD2 | Nucleosomes | 14.97 |
| MLL3 Complex | Core Histone | 13.67 |
| EZH1 Complex | Core Histone | 11.97 |
| SMYD2 | Histone H4 | 9.26 |
| PRMT3 | Histone H4 | 9.01 |
| EZH2 Complex | Core Histone | 8.17 |
| MLL2 Complex | Core Histone | 6.21 |
| SET1B Complex | Core Histone | 5.96 |
| NSD1 | Nucleosomes | 3.81 |
| G9a | Histone H3 (1-21) | 3.72 |
| SET7 | Core Histone | 3.47 |
| SETD2 | Nucleosomes | 3.15 |
| Dot1L | Nucleosomes | 2.75 |
| GLP | Histone H3 (1-21) | 1.86 |
| MLL4 Complex | Core Histone | 0.27 |
| MLL1 Complex | Nucleosomes | 0.27 |
| SUV420H1-tv2 | Nucleosomes | 0.00 |
| SUV39H1 | Histone H3 | 0.00 |
| SET8 | Nucleosomes | 0.00 |
| SUV39H2 | Histone H3 | 0.00 |

In summary, Compound A is a potent, reversible, selective inhibitor of Type I PRMT family members showing equivalent biochemical potency against PRMT1, PRMT6 and PRMT8 with $IC_{50}$ values ranging between 3-5 nM. The crystal structure of PRMT1 in complex with Compound A reveals that Compound A binds in the peptide pocket and both the crystal structure, as well as enzymatic studies are consistent with a SAM uncompetitive mechanism.

Biology

Cellular Mechanistic Effects

Figure 9:
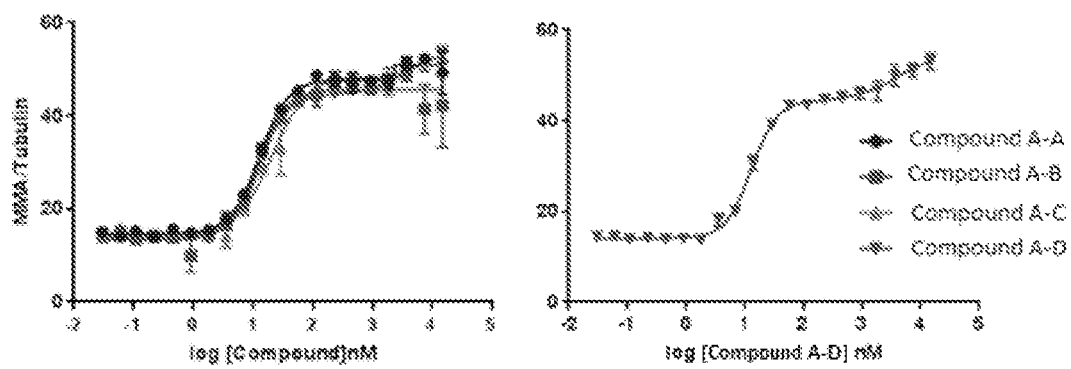
FIG. 9: MMA in-cell-western. RKO cells were treated with Compound A-tri-HCl ("Compound A-A"), Compound A-mono-HCl ("Compound A-B"), Compound A-free-base ("Compound A-C"), and Compound A-di-HCl ("Compound A-D") for 72 hours. Cells were fixed, stained with anti-Rme1GG to detect MMA and anti-tubulin to normalize signal, and imaged using the Odyssey imaging system. MMA relative to tubulin was plotted against compound concentration to generate a curve fit (A) in GraphPad using a biphasic curve fit equation. Summary of $EC_{50}$ (first inflection), standard deviation, and N are shown in (B).

Inhibition of PRMT1 is predicted to result in a decrease of ADMA on cellular PRMT1 substrates, including arginine 3 of histone H4 (H4R3me2a), with concomitant increases in MMA and SDMA (Dhar, S. et al. Loss of the major Type I arginine methyltransferase PRMT1 causes substrate scavenging by other PRMTs. Sci Rep 3, 1311, doi:10.1038/srep01311 (2013)). To evaluate the effect of Compound A on arginine methylation the dose response associated with increased MMA was evaluated in an in-cell-western assay using an antibody to detect MMA and the cellular mechanistic $EC_{50}$ of 10.1±4.4 nM was determined (FIG. 9). The dose response appeared biphasic, possibly due to differential activity between the Type I PRMTs or differential potency towards a particular subset of substrates. An equation describing a biphasic curve was used to fit the data and since there was no obvious plateau associated with the second inflection over the range of concentrations tested, the first inflection was reported. Various salt forms were tested in this assay format and all demonstrated similar $EC_{50}$ values and are, therefore, considered interchangeable for all biology studies (FIG. 9). Additional studies were performed to examine the timing, durability, and impact on other methylation states in select tumor types as indicated below. The potency of Compound A on induction of MMA indicates that Compound A can be used to investigate the biological mechanism associated with inhibition of Type 1 PRMTs in cells.

Type I PRMT Expression in Cancer

Figure 10:
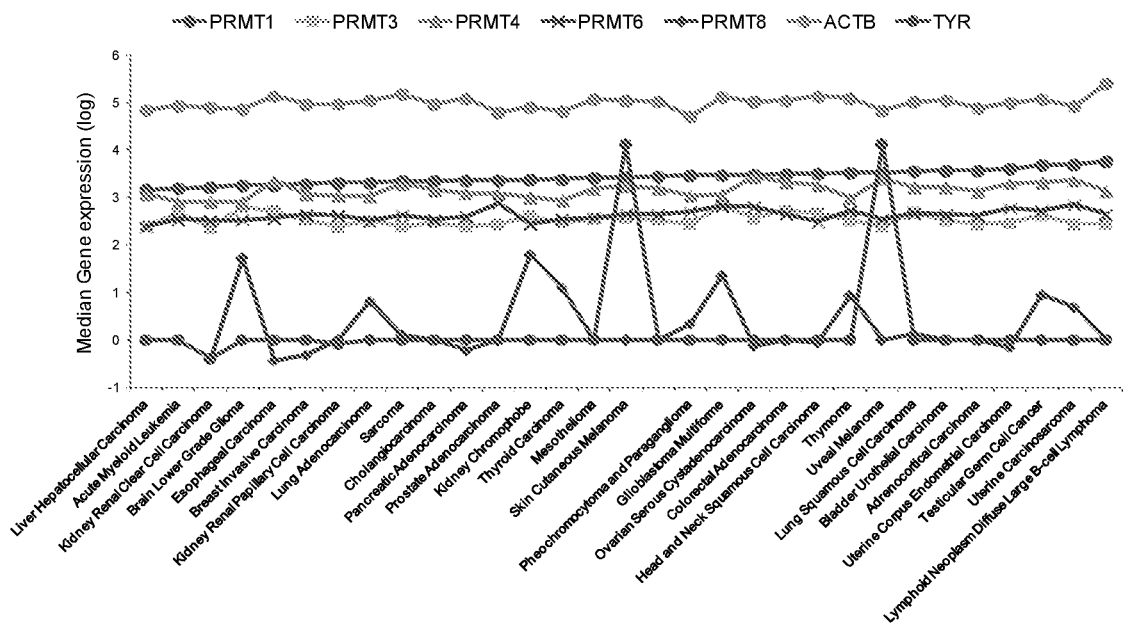
FIG. 10: PRMT1 expression in tumors. mRNA expression levels were obtained from cBioPortal for Cancer Genomics. ACTB levels and TYR are shown to indicate expression of level corresponding to a gene that is ubitiquitously expressed versus one that has restricted expression, respectively.

Analysis of gene expression data from multiple tumor types collected from >100 cancer studies through The Cancer Genome Atlas (TCGA) and other primary tumor databases represented in cBioPortal indicates that PRMT1 is highly expressed g in cancer, with highest levels in lymphoma (diffuse large B-cell lymphoma, DLBCL) relative to other solid and hematological malignancies (FIG. 10). Expression of ACTB, a common housekeeping gene and TYR, a gene selectively expressed in skin, were also surveyed to characterize the range associated with high ubiquitous expression or tissue restricted expression, respectively. High expression in lymphoma among other cancers provides additional confidence that the target of Compound A inhibition is present in primary tumors that correspond to cell lines evaluated in preclinical studies. PRMTs 3, 4, and 6 are also expressed across a range of tumor types while PRMT8 expression appears more restricted as predicted given its tissue specific expression (Lee, J., Sayegh, J., Daniel, J., Clarke, S. & Bedford, M. T. PRMT8, a new membrane-bound tissue-specific member of the protein arginine methyltransferase family. J Biol Chem 280, 32890-32896, doi:10.1074/jbc.M506944200 (2005)).

Cellular Phenotypic Effects

Compound A was analyzed for its ability to inhibit cultured tumor cell line growth in a 6-day growth-death assay using Cell Titer Glo (Promega) that quantifies ATP as a surrogate of cell number. The growth of all cell lines was evaluated over time across a wide range of seeding densities to identify conditions that permitted proliferation throughout the entire 6-day assay. Cells were plated at the optimal seeding density and after overnight incubation, a 20-point 2-fold titration of compound was added and plates were incubated for 6 days. A replicate plate of cells was harvested at the time of compound addition to quantify the starting number of cells ($T_0$). Values obtained after the 6 day treatment were expressed as a function of the $T_0$ value and plotted against compound concentration. The $T_0$ value was normalized to 100% and represents the number of cells at the time of compound addition. The data were fit with a 4 parameter equation to generate a concentration response curve and the growth $IC_{50}$ ($gIC_{50}$) was determined. The $gIC_{50}$ is the midpoint of the 'growth window', the difference between the number of cells at the time of compound addition (To) and the number of cells after 6 days (DMSO control). The growth-death assay can be used to quantify the net population change, clearly defining cell death (cytotoxicity) as fewer cells compared to the number at the time of compound addition (To). A negative $Y_{min}$-$T_0$ value is indicative of cell death while a $gIC_{100}$ value represents the concentration of compound required for 100% inhibition of growth. The growth inhibitory effect of Compound A was evaluated using this assay in 196 human cancer cell lines representing solid and hematological malignancies (FIG. 11).

Figure 11:
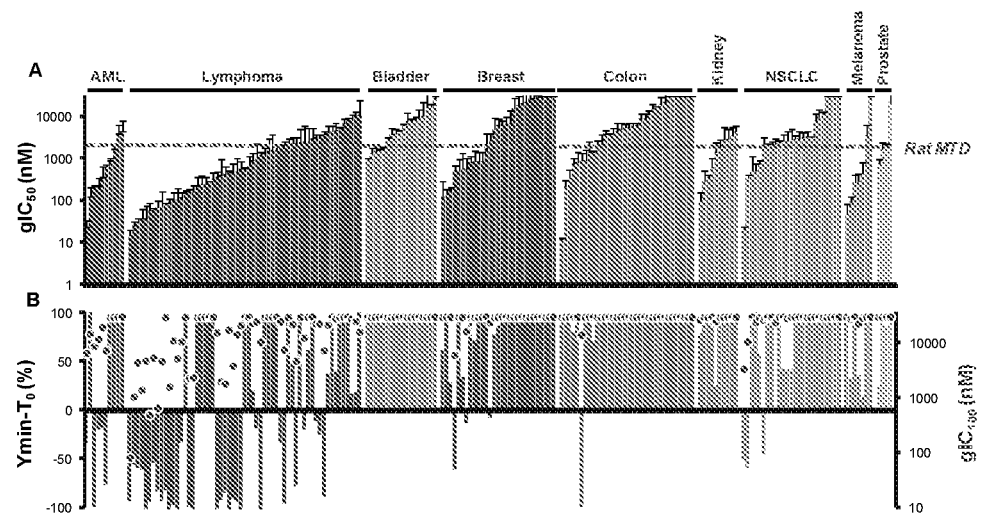
FIG. 11: Antiproliferative activity of Compound A in cell culture. 196 human cancer cell lines were evaluated for sensitivity to Compound A in a 6-day growth assay. $gIC_{50}$ values for each cell line are shown as bar graphs with predicted human exposure as indicated in (A). $Y_{min}$-$T_0$, a measure of cytotoxicity, is plotted as a bar-graph in (B), in which $gIC_{100}$ values for each cell line are shown as red dots. The $C_{ave}$ calculated from the rat 14-day MTD (150 mg/kg, $C_{ave}$=2.1 μM) is indicated as a red dashed line.

Compound A induced near or complete growth inhibition in most cell lines, with a subset showing cytotoxic responses, as indicated by a negative $Y_{min}$-$T_0$ value (FIG. 11B). This effect was most pronounced in AML and lymphoma cancer cell lines, where 50 and 54% of cell lines showed cytotoxic responses, respectively. The total AUC or exposure ($C_{ave}$) calculated from the rat 14-day MTD (150 mg/kg, $C_{ave}$=2.1 µM) was used as an estimate of a clinically relevant concentration of Compound A for evaluation of sensitivity. While lymphoma cell lines showed cytotoxicity with $gIC_{100}$ values below 2.1 µM, many cell lines across all tumor types evaluated showed $gIC_{50}$ values≤2.1 M suggesting that concentrations associated with anti-tumor activity may be achievable in patients. The dog 21-day MTD was slightly higher (25 mg/kg; total AUC or $C_{ave}$=3.2 M), therefore the lower concentration from the rat provides a more conservative target for appreciating cell line sensitivity. Lymphoma cell lines were highly sensitive to Type I PRMT inhibition, with a median $gIC_{50}$ of 0.57 µM and cytotoxicity observed in 54%. Among solid tumor types, potent anti-proliferative activity of Compound A was observed in melanoma and kidney cancer cell lines (primarily representing clear cell renal carcinoma), however, the responses were predominantly cytostatic in this assay format (FIG. 11, Table 2).

TABLE 2

Compound A 6-day proliferation summary. $gIC_{50} \leq 2.1$ µM was used as target based on concentration achieved in the rat 14-day MTD (150 mg/kg, $C_{ave} = 2.1$ µM).

|  | Total | AML | Lymphoma | Bladder | Breast | Colon | Kidney | NSCLC | Melanoma | Prostate |
|---|---|---|---|---|---|---|---|---|---|---|
| Median $gIC_{50}$ (µM) | 2.12 | 0.54 | 0.57 | 5.32 | 5.95 | 5.51 | 1.66 | 2.81 | 0.28 | 1.86 |
| Median $gIC_{100}$ (µM) | 29.33 | 16.72 | 21.62 | 29.33 | 29.36 | 29.33 | 29.35 | 29.33 | 29.33 | 29.34 |
| % Cytotoxic | 23% | 50% | 54% | 0% | 10% | 3% | 0% | 16% | 0% | 0% |
| % $gIC_{50} < 2$ µM | 49% | 80% | 69% | 28% | 41% | 29% | 60% | 28% | 71% | 75% |
| % $gIC_{100} < 2$ µM | 4% | 0% | 14% | 0% | 0% | 0% | 0% | 0% | 0% | 0% |
| Total Cell Lines | 196 | 10 | 59 | 18 | 29 | 34 | 10 | 25 | 7 | 4 |

Figure 12:
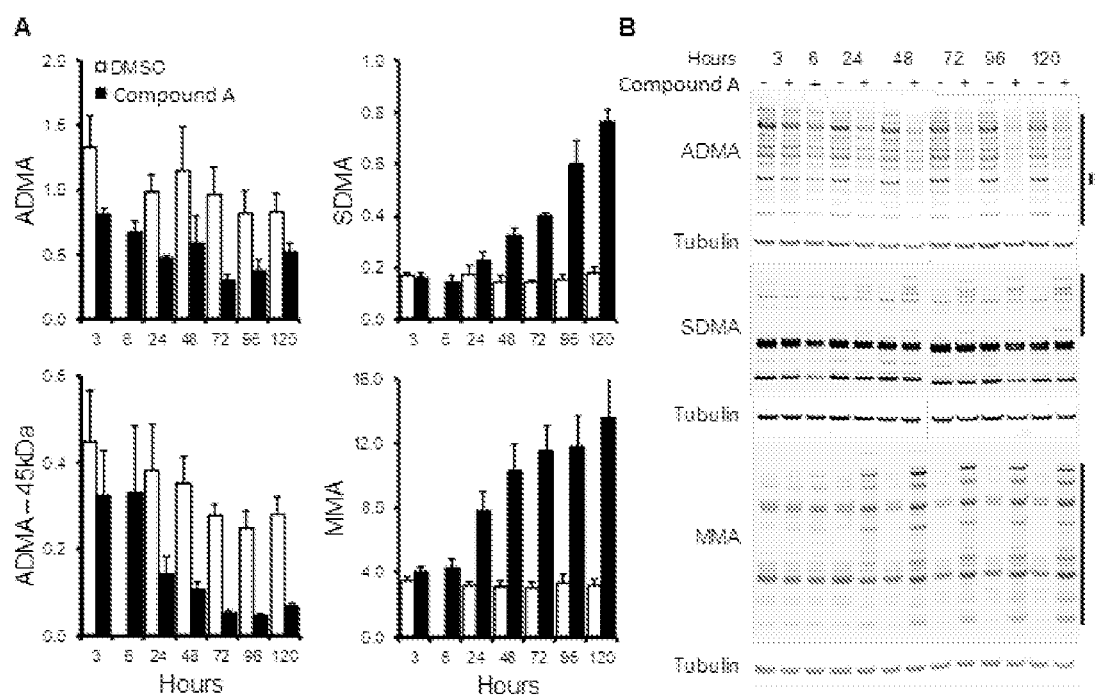
FIG. 12: Timecourse of Compound A effects on arginine methylation marks in cultured cells. (A) Changes in ADMA, SDMA, and MMA in Toledo DLBCL cells treated with Compound A. Changes in methylation are shown normalized relative to tubulin±SEM (n=3). (B) Representative western blots of arginine methylation marks. Regions quantified are denoted by black bars on the right of the gel.

Evaluation of the anti-proliferative effects of Compound A indicates that inhibition of PRMT1 results in potent anti-tumor activity across cell lines representing a range of solid and hematological malignancies. Together, these data suggest that clinical development in solid and hematological malignancies is warranted. Prioritized indications include:
Lymphoma: cytotoxicity in 54% of cell lines
AML: cytotoxicity in 50% of cell lines
Renal cell carcinoma: $gIC_{50} \leq 2.1$ µM in 60% of cell lines
Melanoma: $gIC_{50} \leq 2.1$ µM in 71% of cell lines
Breast cancer including TNBC: $gIC_{50} \leq 2.1$ M in 41% of cell lines Lymphoma Biology
Cell Mechanistic Effects To evaluate the effect of Compound A on arginine methylation in lymphoma, a human DLBCL cell line (Toledo) was treated with 0.4 µM Compound A or vehicle for up to 120 hours after which protein lysates were evaluated by western analysis using antibodies for various arginine methylation states. As predicted, ADMA methylation decreased while MMA increased upon compound exposure (FIG. 12). An increase in levels of SDMA was also observed, suggesting that the increase in MMA may have resulted in accumulation in the pool of potential substrates for PRMT5, the major catalyst of SDMA formation. Given the detection of numerous substrates with varying kinetics, and variability of ADMA levels among DMSO-treated samples, both the full lane and a prominent 45 kDa band were characterized to assess ADMA. Increases in MMA were apparent by 24 hours and near maximal by 48 hours while decreases in the 45 kDa ADMA band required 72-96 hours to achieve maximal effect. Increases in SDMA were apparent after 48 hours of compound exposure and continued to increase through 120 hours, consistent with the potential switch from conversion of MMA to ADMA by Type I PRMTs to SDMA by Type II PRMTs (FIG. 12).

Figure 13:
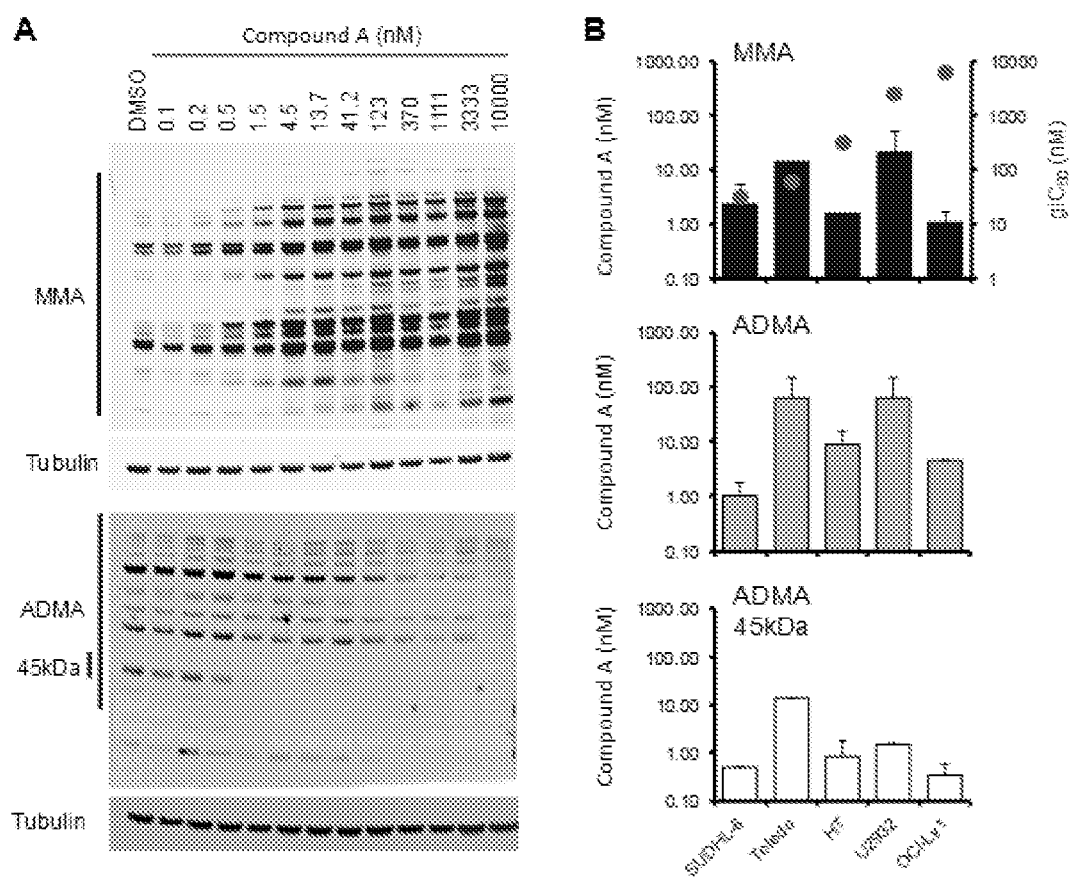
FIG. 13: Dose response of Compound A on arginine methylation. (A) Representative western blot images of MMA and ADMA from the Compound A dose response in the U2932 cell line. Regions quantified for (B) are denoted by black bars to the left of gels. (B) Minimal effective Compound A concentration required for 50% of maximal induction of MMA or 50% maximal reduction ADMA in 5 lymphoma cell lines after 72 hours of exposure±standard deviation (n=2). Corresponding $gIC_{50}$ values in 6-day growth death assay are as indicated in red.

The dose response associated with Compound A effects on arginine methylation (MMA, ADMA, SDMA) was determined in a panel of lymphoma cell lines (FIG. 13). ADMA decreases were measured across the full lane and the single 45 kDa band that decreased to undetectable levels across all cell lines evaluated. Overall, concentrations required to achieve 50% of the maximal effect were similar across cell lines and did not correspond to the $gIC_{50}$ in the 6-day growth death assay, suggesting that the lack of sensitivity is not explained by poor target engagement.

Figure 14:
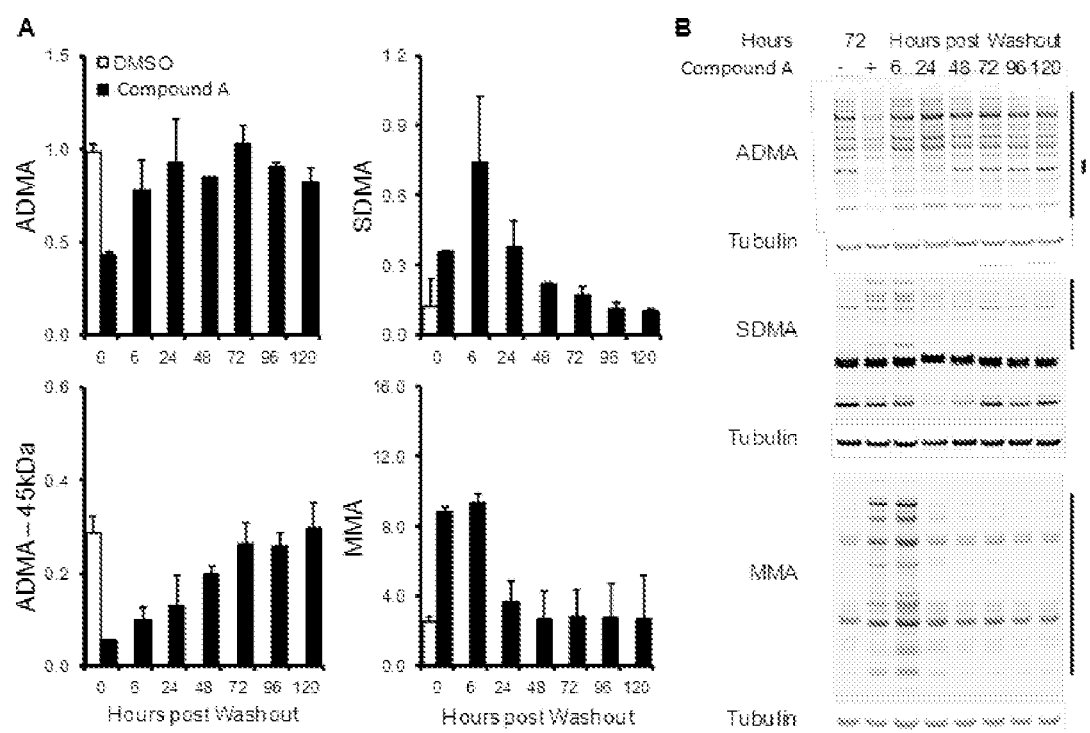
FIG. 14: Durability of arginine methylation marks in response to Compound A in lymphoma cells. (A) Stability of changes to ADMA, SDMA, and MMA in the Toledo DLBCL cell line cultured with Compound A. Changes in methylation are shown normalized relative to tubulin±SEM (n=3). (B) Representative western blots of arginine methylation marks. Regions quantified for (A) are denoted by black bars on the side of the gel.

To determine the durability of global changes in arginine methylation in response to Compound A, ADMA, SDMA, and MMA levels were assessed in cells treated with Compound A after compound washout (FIG. 14). Toledo cells were cultured with 0.4 M Compound A for 72 hours to establish robust effects on arginine methylation marks. Cells were then washed, cultured in Compound A-free media, samples were collected daily through 120 hours, and arginine methylation levels were examined by western analysis. MMA levels rapidly decreased, returning to baseline by 24 hours after Compound A washout, while ADMA and SDMA returned to baseline by 24 and 96 hours, respectively. Notably, recovery of the 45 kDa ADMA band appeared delayed relative to most other species in the ADMA western blots, suggesting the durability of arginine methylation changes by Compound A may vary by substrate. SDMA appeared to continue to increase even after 6 hours of washout. This is consistent with the continued increase observed through 120 hours without any obvious plateau (FIG. 12) coupled with the durable increase in MMA that has not yet returned to baseline after washout. Durability of each modification generally reflected the kinetics of arginine methylation changes brought about by Compound A, with MMA being the most rapid.

Cell Phenotypic Effects

Figure 15:
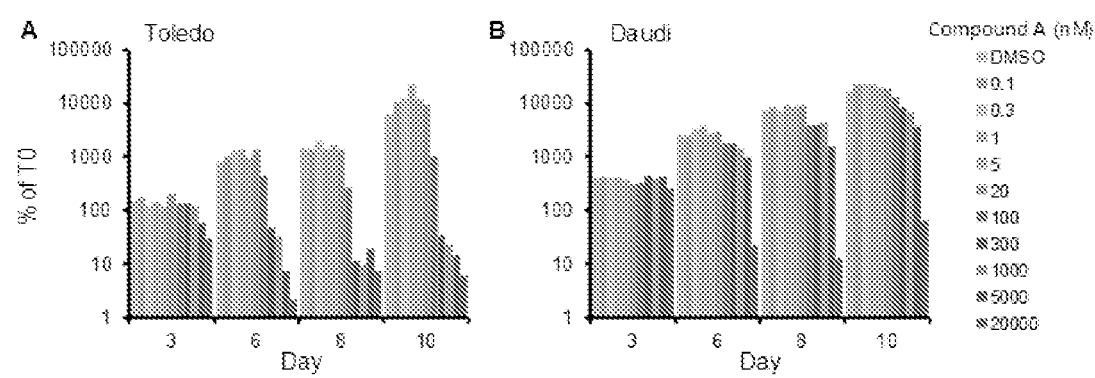
FIG. 15: Proliferation timecourse of lymphoma cell lines. Cell growth was assessed over a 10-day timecourse in the Toledo (A) and Daudi (B) cell lines (n=2 per cell line). Representative data for a single biological replicate are shown.

To assess the time course associated with inhibition of growth by Compound A, an extended duration growth-death assay was performed in a subset of lymphoma cell lines. Similar to the 6-day proliferation assay described previously, the seeding density was optimized to ensure growth throughout the duration of the assay, and cell number was assessed by CTG at selected timepoints beginning from days 3-10. Growth inhibition was observed as early as 6 days and was maximal by 8 days in Toledo and Daudi lymphoma cell lines (FIG. 15).

Figure 16:
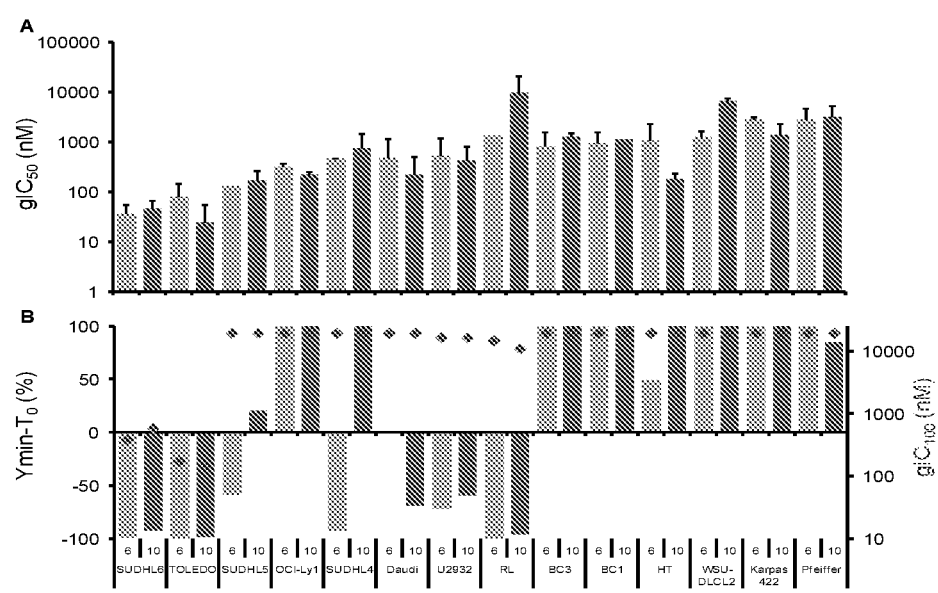
FIG. 16: Anti-proliferative effects of Compound A in lymphoma cell lines at 6 and 10 days. (A) Average $gIC_{50}$ values from 6 day (light blue) and 10 day (dark blue) proliferation assays in lymphoma cell lines. (B) $Y_{min}$-$T_0$ at 6 day (light blue) and 10 day (dark blue) with corresponding $gIC_{100}$ (red points).

A larger set of cell lines was evaluated on days 6 and 10 to measure the effects of prolonged exposure to Compound A and determine whether cell lines that displayed a cytostatic response in the 6-day assay might undergo cytotoxicity at later timepoints. The extended time of exposure to Compound A had minimal effects on potency ($gIC_{50}$) or cytotoxicity ($Y_{min}-T_0$) across lymphoma cell lines evaluated (FIG. 16) indicating that 6-day proliferation evaluation could be utilized for assessment of sensitivity.

Figure 17:
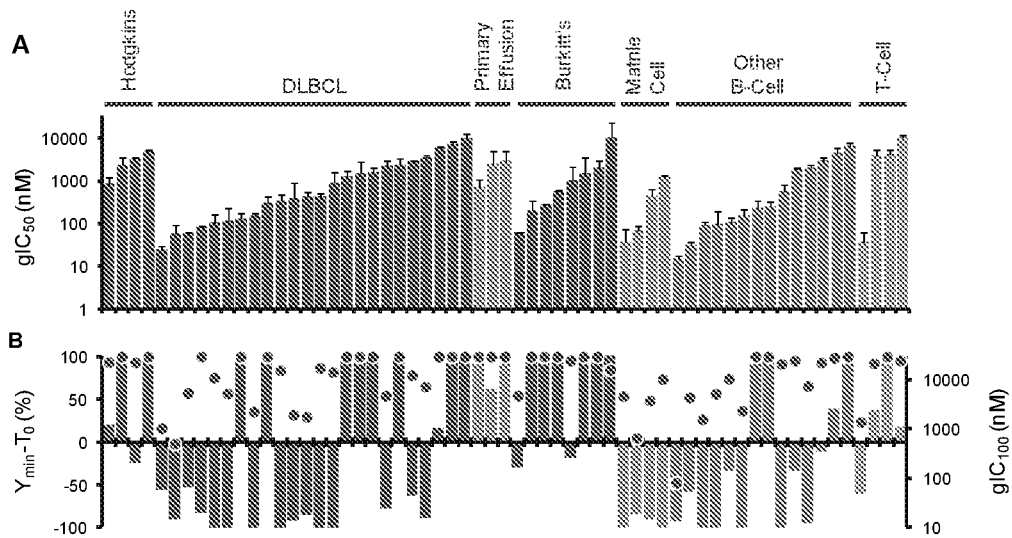
FIG. 17: Anti-proliferative effects of Compound A in lymphoma cell lines as classified by subtype. (A) $gIC_{50}$ values for each cell line are shown as bar graphs. $Y_{min}$-$T_0$, a measure of cytotoxicity, is plotted as a bar-graph in (B), in which $gIC_{100}$ values for each cell line are shown as red dots. Subtype information was collected from the ATCC or DSMZ cell line repositories.

Given that growth inhibition was apparent at day 6 and prolonged exposure had minimal impact on potency or percent inhibition, a broad panel of lymphoma cell lines representing Hodgkin's and non-Hodgkin's subtypes was evaluated in the 6-day growth-death assay format (FIG. 17). All subtypes appeared equally sensitive in this format and many cell lines underwent cytotoxicity (as indicated by negative $Y_{min}-T_0$) independent of classification, suggesting that Compound A has anti-tumor effects in all subtypes of lymphoma evaluated.

Figure 18:
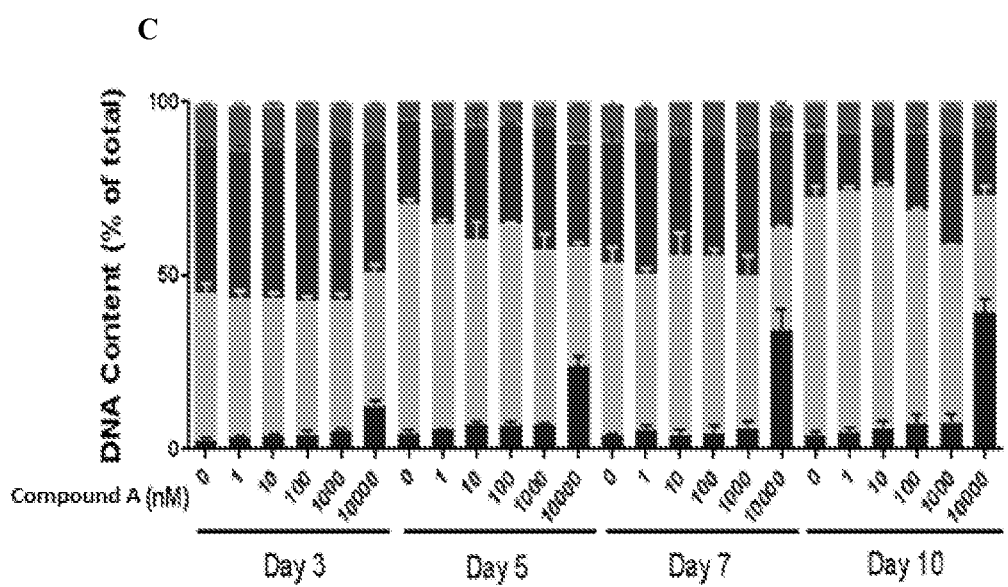
FIG. 18: Propidium iodide FACS analysis of cell cycle in human lymphoma cell lines. Three lymphoma cell lines, Toledo (A), U2932 (B), and OCI-Ly1 (C) were treated with 0, 1, 10, 100, 1000, and 10,000 nM Compound A for 10 days with samples taken on days 3, 5, 7, 10 post treatment. Data represents the average±SEM of biological replicates, n=2.

The proliferation assay results suggest that the inhibition of PRMT1 induces apparent cytotoxicity in a subset of lymphoma cell lines. To further elucidate this effect, the cell cycle distribution in lymphoma cell lines treated with Compound A was evaluated using propidium iodide staining followed by flow cytometry. Cell lines that showed a range of $Y_{min}-T_0$ and $gIC_{50}$ values in the 6-day proliferation assay were seeded at low density to allow logarithmic growth over the duration of the assay, and treated with varying concentrations of Compound A. Consistent with the growth-death assay results, an accumulation of cells in sub-G1 (<G1), indicative of cell death, was observed in Toledo cells in a time and dose dependent manner beginning after 3 days of treatment with Compound A concentrations 1000 nM (FIG. 18). By day 7, an increase in the sub-G1 population was apparent at concentrations 100 nM. In U2932 and OCI-Ly1, cell lines that underwent apparent cytostatic growth inhibition in the 6-day proliferation assay, this effect was only evident at 10 M Compound A. No profound effect in any other cell cycle phase was revealed in this assay format.

Figure 19:
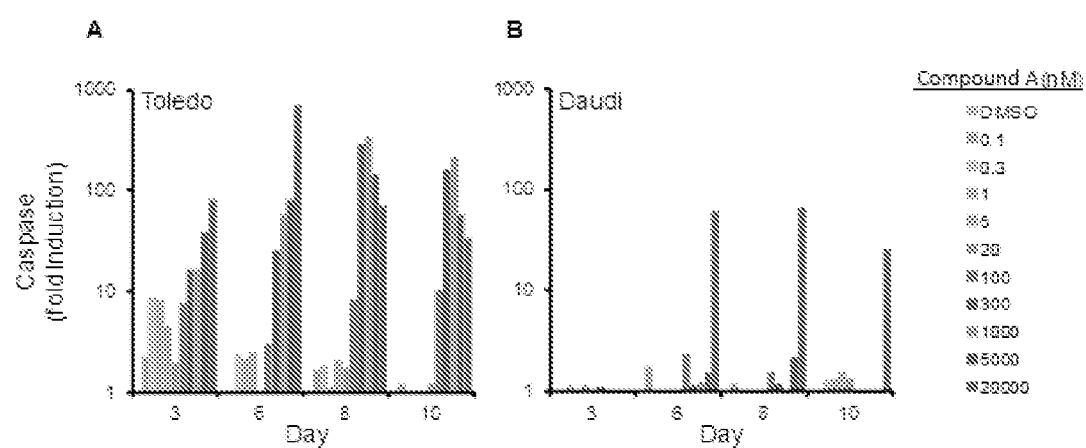
FIG. 19: Caspase-3/7 activation in lymphoma cell lines treated with Compound A. Apoptosis was assessed over a 10-day timecourse in the Toledo (A) and Daudi (B) cell lines. Caspase 3/7 activation is shown as fold-induction relative to DMSO-treated cells. Two independent replicates were performed for each cell line. Representative data are shown for each.

To confirm the FACS analysis of cell cycle, evaluation of caspase cleavage was performed as an additional measure of apoptosis during a 10-day timecourse. Seeding density was optimized to ensure consistent growth throughout the duration of the assay, and caspase activation was assessed using a luminescent Caspase-Glo 3/7 assay (Promega). Caspase-Glo 3/7 signal was normalized to cell number (assessed by CTG) and shown as fold-induction relative to control (DMSO treated) cells. Caspase 3/7 activity was monitored over a 10-day timecourse in DLBCL cell lines showing cytotoxic (Toledo) and cytostatic (Daudi) responses to Compound A (FIG. 19). Consistent with the profile observed in the growth-death assay, the Toledo cell line showed robust caspase activation concurrent with decreases in cell number at all timepoints, while induction of caspase activity in the Daudi cell line was less pronounced and limited to the highest concentrations of Compound A.

Together with the cell cycle profiles, these data indicate that Compound A induces caspase-mediated apoptosis in the Toledo DLBCL cell line, suggesting the cytotoxicity observed in other lymphoma cell lines may reflect activation of apoptotic pathways by Compound A.

Anti-Tumor Effects in Mouse Xenografts

Figure 20:
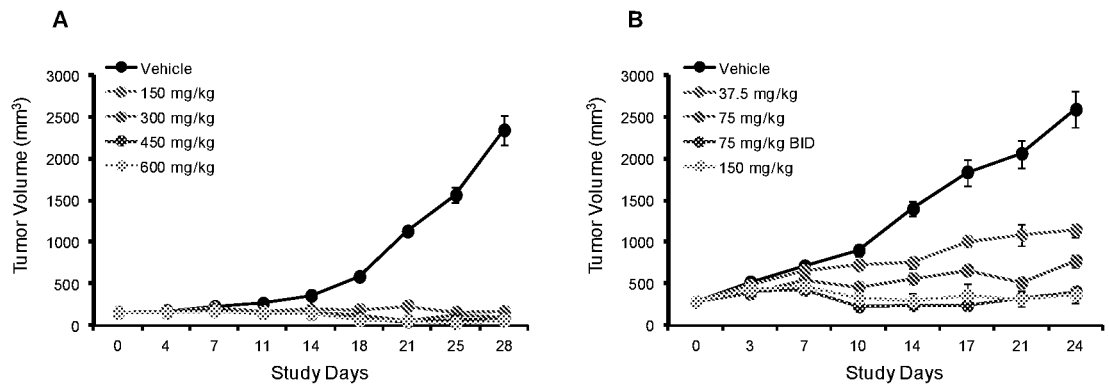
FIG. 20: Efficacy of Compound A in mice bearing Toledo xenografts. Mice were treated QD (37.5, 75, 150, 300, 450, or 600 mg/kg) with Compound A orally or BID with 75 mg/kg (B) over a period of 28 (A) or 24 (B) days and tumor volume was measured twice weekly.

The effect of Compound A on tumor growth was assessed in a Toledo (human DLBCL) xenograft model. Female SCID mice bearing subcutaneous Toledo tumors were weighed, tumors were measured with callipers, and mice were block randomized according to tumor size into treatment groups of 10 mice each. Mice were dosed orally with either vehicle or Compound A (150 mg/kg-600 mg/kg) for 28 days daily. Throughout the study, mice were weighed and tumor measurements were taken twice weekly. Significant tumor growth inhibition (TGI) was observed at all doses and regressions were observed at doses≥300 mg/kg (FIG. 20, Table 5). There was no significant body weight loss in any dose group.

Given that complete TGI was observed at all doses evaluated, a second study was performed to test the anti-tumor effect of Compound A at lower doses as well as to compare twice daily (BID) dosing relative to daily (QD). In this second study, mice were dosed orally with either vehicle or Compound A (37.5 mg/kg-150 mg/kg) for 24 days QD or 75 mg/kg BID. In this study, BID administration of 75 mg/kg resulted in the same TGI as 150 mg/kg (95% and 96%, respectively) while ≤75 mg/kg QD resulted in partial TGI (≤79%) (FIG. 20, Table 5). No significant body weight loss was observed in any dose group. These data suggest that either BID or QD dosing with the same total daily dose should result in similar efficacy.

Additional Tumor Types

AML

In addition to lymphoma cell lines, Compound A had potent, cytotoxic activity in a subset of AML cell lines examined in the 6-day proliferation assay (Table 3). Eight of 10 cell lines had $gIC_{50}$ values<2M, and Compound A induced cytotoxicity in 5 cell lines. Although PRMT1 interacts with the AML-ETO fusion characteristic of the M2 AML subtype (Shia, W. J. et al. PRMT1 interacts with AML1-ETO to promote its transcriptional activation and progenitor cell proliferative potential. Blood 119, 4953-4962, doi:10.1182/blood-2011-04-347476 (2012)), cell lines carrying this fusion protein (Kasumi-1 and SKNO-1) were not the only lines showing sensitivity to Compound A as measured by $gIC_{50}$ or that underwent cytotoxicity (Table 3, FIG. 21), therefore, the presence of this oncogenic fusion protein does not exclusively predict sensitivity of AML cell lines to Compound A.

TABLE 3

Summary of Compound A activity in AML cell lines

| Cell Line | $gIC_{50}$ (µM) | $gIC_{100}$ (µM) | Ymin-$T_0$ | Subtype |
|---|---|---|---|---|
| HL-60 | 0.02 ± 0.01 | 6.38 ± 12.83 | −33.4 | M3 |
| MV-4-11 | 0.12 ± 0.08 | 14.55 ± 4.27 | 565.6 | M5 |
| MOLM-13 | 0.21 ± 0.01 | 8.64 ± 0.39 | −100.0 | M5 |
| SKM-1 | 0.22 ± 0.11 | 11.61 ± 5.52 | −19.1 | M5 |
| KASUMI-1 | 0.36 ± 0.25 | 18.88 ± 10.55 | −17.7 | M2 |
| MOLM-16 | 0.65 ± 0.01 | 9.69 ± 10.58 | −68.6 | M0 |
| OCI-AML3 | 0.87 ± 0.14 | 29.33 ± 0.00 | 523.2 | M4 |
| TF-1 | 1.67 ± 0.36 | 29.33 ± 0.00 | 788.1 | M6 |
| NOMO-1 | 3.85 ± 2.10 | 29.33 ± 0.00 | 259.1 | M5 |
| SHI-1 | 4.29 ± 3.52 | 29.33 ± 0.02 | 292.0 | M5 |

Figure 21:
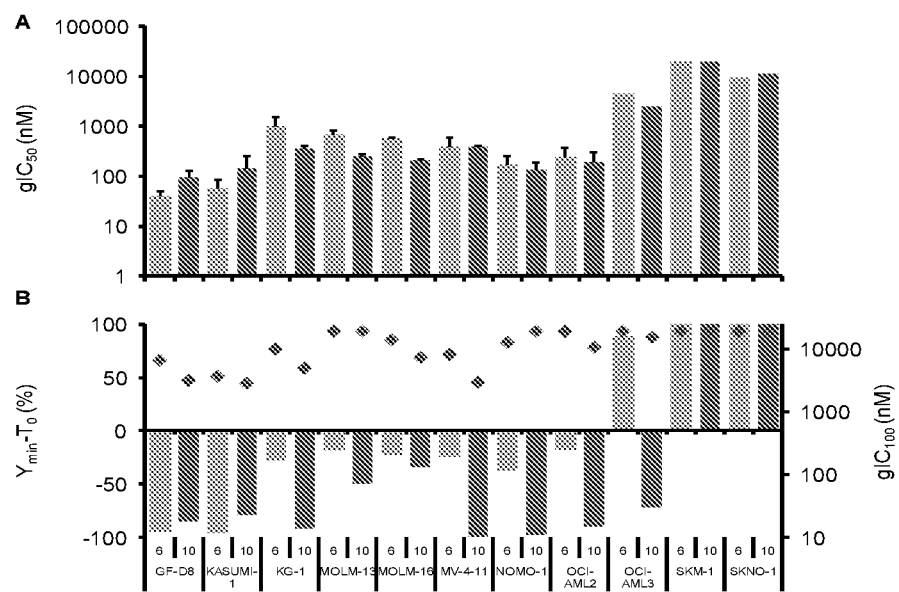
FIG. 21: Effect of Compound A in AML cell lines at 6 and 10 Days. (A) Average $gIC_{50}$ values from 6 day (light blue) and 10 day (dark blue) proliferation assays in AML cell lines. (B) $Y_{min}$-$T_0$ at 6 day (light blue) and 10 day (dark blue) with corresponding $gIC_{100}$ (red points).

Similar to studies in lymphoma, a set of cell lines was evaluated on days 6 and 10 to measure the effects of prolonged exposure to Compound A and determine whether AML cell lines that displayed a cytostatic response in the 6-day assay might undergo cytotoxicity at later timepoints. Consistent with the lymphoma result, extending time of exposure to Compound A had minimal effects on potency ($gIC_{50}$) or cytotoxicity ($Y_{min}-T_0$) across AML cell lines evaluated (FIG. 21).

Renal Cell Carcinoma

Renal cell carcinoma cell lines had among the lowest median $gIC_{50}$ compared with other solid tumor types. Although none of the lines tested showed a cytotoxic response upon treatment with Compound A, all showed complete growth inhibition and 6 of 10 had $gIC_{50}$ values≤2 µM (Table 4). 7 of the 10 lines profiled represent clear cell renal carcinoma (ccRCC), the major clinical subtype of renal cancer.

TABLE 4

Summary of Compound A anti-proliferative effects in renal cell carcinoma cells

| Cell Line | $gIC_{50}$ (µM) | Ymin-$T_0$ | Subtype |
|---|---|---|---|
| ACHN | 0.10 ± 0.05 | 96.5 | ccRCC |
| CAKI-1 | 0.28 ± 0.23 | 178.7 | ccRCC |
| G-401 | 0.35 ± 0.04 | 353.7 | Wilm's |

TABLE 4-continued

Summary of Compound A anti-proliferative effects in renal cell carcinoma cells

| Cell Line | gIC$_{50}$ (µM) | Ymin-T$_0$ | Subtype |
|---|---|---|---|
| 786-O | 0.59 ± 0.41 | 643.7 | ccRCC |
| SK-NEP-1 | 1.43 ± 0.86 | 25.3 | Wilm's |
| 769-P | 1.89 ± 0.82 | 119.0 | ccRCC |
| A498 | 2.73 ± 2.81 | 313.4 | ccRCC |
| G-402 | 2.89 ± 2.05 | 92.6 | Leiomyoblastoma |
| SW156 | 3.51 ± 2.01 | 346.7 | ccRCC |
| CAKI-2 | 4.23 ± 1.51 | 169.6 | ccRCC |

To assess the time course of growth inhibition in renal carcinoma cell lines by Compound A, cell growth was assessed by CTG in a panel of 4 ccRCC cell lines at days 3,4,5, and 6 (FIG. 22). The largest shift in activity occurred between days 3 and 4, where all cell lines showed decreases gIC$_{50}$ values and increases growth inhibition. Potency of Compound A (assessed by gIC$_{50}$) was maximal by 4 days in 3 of 4 lines and did further not change through the 6 day assay duration. Additionally, percent growth inhibition reached 100% in all cell lines evaluated. Therefore, maximal growth inhibition in ccRCC cell lines was apparent within the 6-day growth window utilized in the cell line screening strategy.

Caspase activation was evaluated during the proliferation timecourse and, consistent with the lack of overt cytotoxicity as indicated by the Y$_{min}$-T$_0$ values, caspase cleavage only occurred at the highest concentration (30 µM) indicating that apoptosis may have a minimal contribution to the overall growth inhibitory effect induced by Compound A in ccRCC cell lines.

Figure 23:
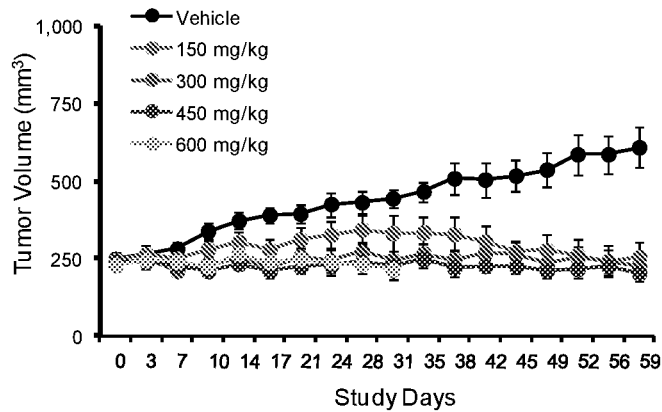
FIG. 23: Efficacy of Compound A in ACHN xenografts. Mice were treated daily with Compound A orally over a period of 28 days and tumor volume was measured twice weekly.

The effect of Compound A on tumor growth was assessed in mice bearing human renal cell carcinoma xenografts (ACHN). Female SCID mice bearing subcutaneous ACHN cell line tumors were weighed and tumors were measured by callipers and block randomized according to tumor size into treatment groups of 10 mice each. Mice were dosed orally with either vehicle or Compound A (150 mg/kg-600 mg/kg) for up to 59 days daily. Throughout the study, mice were weighed and tumor measurements were taken twice weekly. Significant tumor growth inhibition was observed at all doses and regressions were observed at doses≥300 mg/kg. Significant body weight loss was observed in animals treated with 600 mg/kg daily and, therefore, that dosing group was terminated on day 31 (FIG. 23, Table 5).

TABLE 5

Efficacy of Compound A in vivo

| Cell Line (Tumor Type) | Dose (mg/kg) | TGI (Regression) | Day | Body weight Difference (vs. vehicle) |
|---|---|---|---|---|
| Toledo (DLBCL) | 150 QD | 99%* | 28 | -4% |
| | 300 QD | 100%* (37%) | | -3% |
| | 450 QD | 100%* (58%) | | -8% |
| | 600 QD | 100%* (62%) | | -7% |
| Toledo (DLBCL) | 37.5 QD | 63%* | 25 | -5% |
| | 75 QD | 79%* | | -5% |
| | 75 BID | 95%* | | -4% |
| | 150 QD | 96%* | | -7% |
| ACHN (ccRCC) | 150 QD | 98%* | 59 | -3% |
| | 300 QD | 100%* (2%) | | -4% |
| | 450 QD | 100%* (15%) | | -7% |
| | 600 QD** | 100%* (6%) | | -17% |

*p < 0.05, two-tailed t-test
**600 QD arm of ACHN efficacy study was terminated at day 31

Together, these data suggest that 100% TGI can be achieved at similar doses in subcutaneous xenografts of human solid and hematologic tumors.

Breast Cancer

Figure 24:
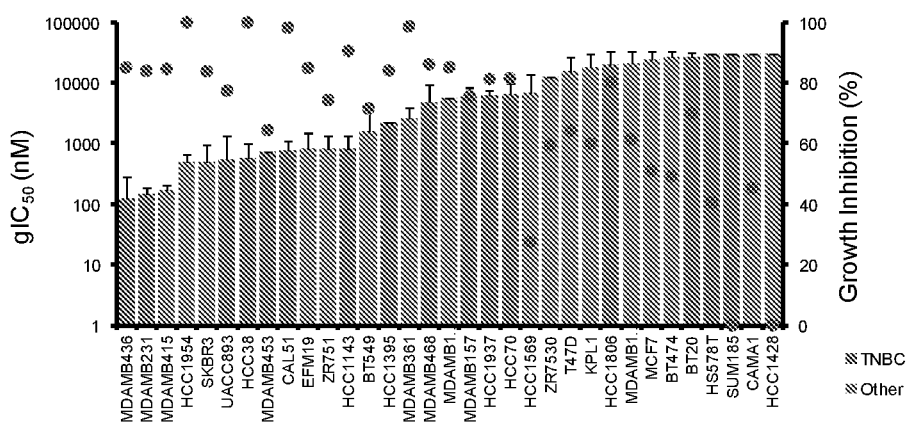
FIG. 24: Anti-proliferative effects of Compound A in breast cancer cell lines. Bar graphs of $gIC_{50}$ and growth inhibition (%) (red circles) for breast cancer cell lines profiled with Compound A in the 6-day proliferation assay. Cell lines representing triple negative breast cancer (TNBC) are shown in orange; other subtypes are in blue.
Figure 25:
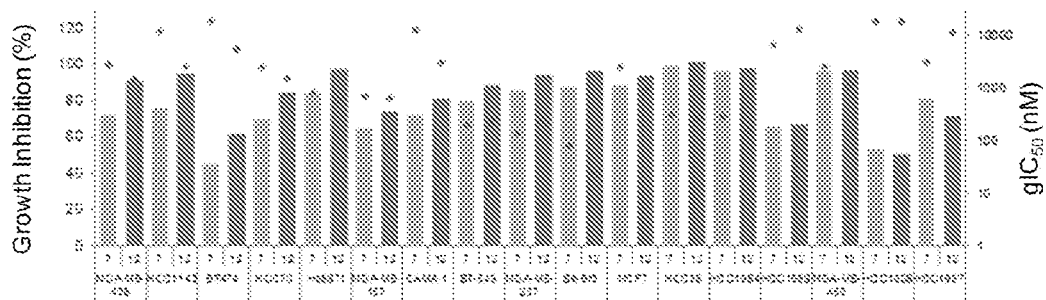
FIG. 25: Effect of Compound A in Breast Cancer Cell Lines at 7 and 12 Days. Average growth inhibition (%) values from 7 day (light blue) and 10 day (dark blue) proliferation assays in breast cancer cell lines with corresponding $gIC_{50}$ (red points) The increase in potency and percent inhibition observed in long-term proliferation assays with breast cancer, but not lymphoma or AML cell lines, suggest that certain tumor types require a longer exposure to Compound A to fully reveal anti-proliferative activity.

Breast cancer cell lines displayed a range of sensitivities to Compound A and in many cases, showed partial growth inhibition in the 6-day proliferation assay (FIG. 24). Cell lines representing triple negative breast cancer (TNBC) had slightly lower median gIC$_{50}$ values compared with non-TNBC cell lines (3.6 µM and 6.8 µM for TNBC and non-TNBC, respectively). Since the effect on proliferation by Compound A was cytostatic and did not result in complete growth inhibition in the majority of breast cancer cell lines, an extended duration growth-death assay was performed to determine whether the sensitivity to Compound A would increase with prolonged exposure. In 7/17 cell lines tested there was an increase in percent maximal inhibition by ≥10% and a ≥2-fold decrease in gIC$_{50}$ (FIG. 25). In the prolonged exposure assay, 11/17 cell lines had gIC$_{50}$≤2 µM (65%) while 7/17 (41%) met this criteria in the 7 day assay format.

Melanoma

Among solid tumor types, Compound A had the most potent anti-proliferative effect in melanoma cell lines (FIG. 11). Six of 7 lines assessed had gIC$_{50}$ values less than 2 µM (Table 6). The effect of Compound A was cytostatic in all melanoma lines, regardless of gIC$_{50}$ value.

TABLE 6

Summary of Compound A Activity in Melanoma Cell Lines

| Cell Line | gIC$_{50}$ (µM) | gIC$_{100}$ (µM) | Y$_{min}$-T$_0$ |
|---|---|---|---|
| A375 | 0.05 ± 0.03 | 29.33 ± 0.00 | 91.9 |
| SK-MEL-5 | 0.09 ± 0.03 | 27.09 ± 3.92 | 31.8 |
| IGR-1 | 0.27 ± 0.14 | 29.33 ± 0.00 | 507.0 |
| SK-MEL-2 | 0.28 ± 0.14 | 22.37 ± 12.11 | 35.9 |
| COLO741 | 0.43 ± 0.37 | 28.55 ± 1.40 | 12.5 |
| HT144 | 3.46 ± 2.68 | 29.33 ± 0.00 | 124.9 |
| MDA-MB-435S | 29.36 ± 0.00 | 29.33 ± 0.00 | 19.1 |

Example 2

Background

PRMT5 is a Symmetric Protein Arginine Methyltransferase

Figure 26:
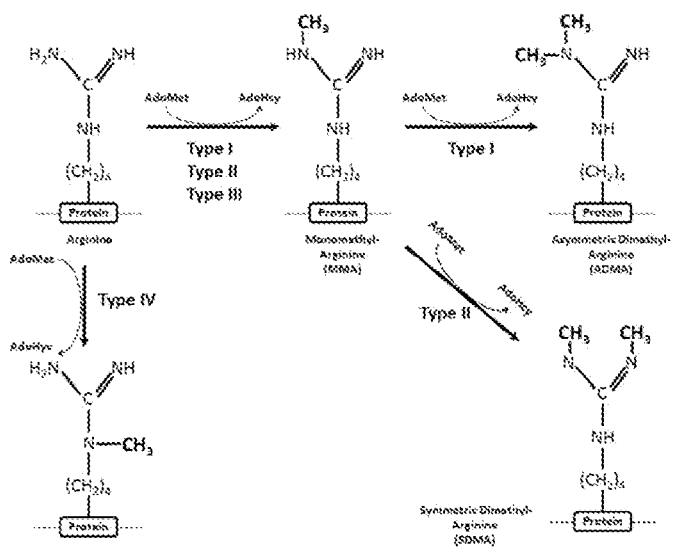
FIG. 26: Four types of protein arginine methylation catalyzed by PRMTs.

Protein arginine methyltransferases (PRMTs) are a subset of enzymes that methylate arginines in proteins that contain regions rich in glycine and arginine residues (GAR motifs). The PRMTs are categorized into four sub-types (Type I-IV) based on the product of the enzymatic reaction (FIG. 26, Fisk J C, et al. A type III protein arginine methyltransferase from the protozoan parasite Trypanosoma brucei. J Biol Chem. 2009 Apr. 24; 284(17):11590-600). Type I-III enzymes generate ω-N-monomethyl-arginine (MMA). The largest subtype, Type I (PRMT1, 3, 4, 6 and 8), progresses MMA to asymmetric dimethyl arginine (ADMA), while Type II generates symmetric dimethyl arginine (SDMA). While PRMT9/FBXO11 can also generate SDMA, PRMT5 is the primary enzyme responsible for symmetric dimethylation. PRMT5 functions in several types of complexes in the cytoplasm and the nucleus and binding partners of PRMT5 are required for substrate recognition and selectivity. Methylosome protein 50 (MEP50) is a known cofactor of PRMT5 that is required for PRMT5 binding and activity towards histones and other substrates (Ho M C, et al. Structure of the arginine methyltransferase PRMT5-MEP50 reveals a mechanism for substrate specificity. PLoS One. 2013; 8(2)).

PRMT5 Substrates

Figure 27:
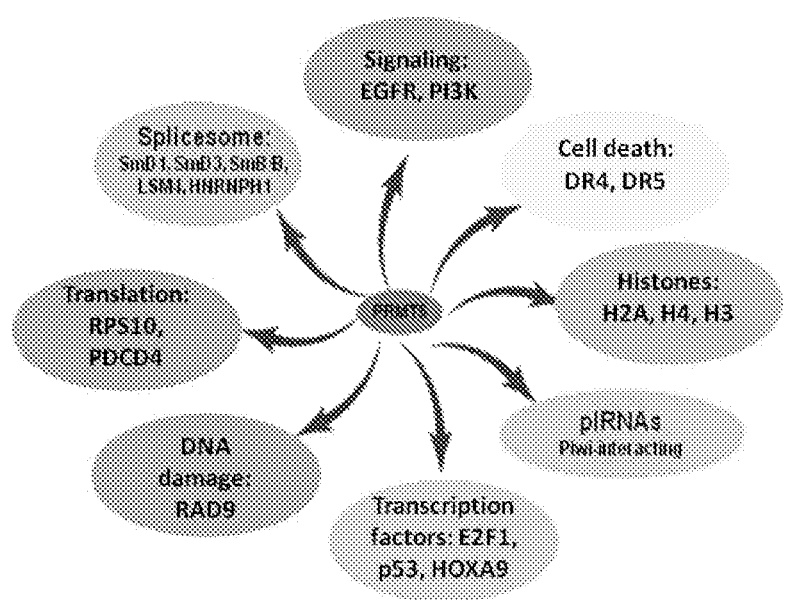
FIG. 27: Known PRMT5 substrates. PRMT5 symmetrically methylates arginines in multiple proteins, preferentially in regions rich in arginine and glycine residues (Karkhanis V, et al. Versatility of PRMT5-induced methylation in growth control and development. Trends Biochem Sci. 2011 December; 36(12):633-41). The vast majority of these substrates were identified through their ability to interact with PRMT5.

PRMT5 methylates arginines in various cellular proteins including splicing factors, histones, transcription factors, kinases and others (FIG. 27) (Karkhanis V, et al. Trends Biochem Sci. 2011 December; 36(12):633-41). Methylation of multiple components of the spliceosome is a key event in spliceosome assembly and the attenuation of PRMT5 activity through knockdown or gene knockout leads to disruption of cellular splicing (Bezzi M, et al. Regulation of constitutive and alternative splicing by PRMT5 reveals a role for Mdm4 pre-mRNA in sensing defects in the spliceosomal machinery. Genes Dev. 2013 Sep. 1; 27(17):1903-16). PRMT5 also methylates histone arginine residues (H3R8, H2AR3 and H4R3) and these histone marks are associated with transcriptional silencing of tumor suppressor genes, such as RB and ST7 (Wang L, et al. Protein arginine methyltransferase 5 suppresses the transcription of the RB family of tumor suppressors in leukemia and lymphoma cells. Mol Cell Biol. 2008 October; 28(20):6262-77; Pal S, et al. Low levels of miR-92b/96 induce PRMT5 translation and H3R8/H4R3 methylation in mantle cell lymphoma. EMBO J. 2007 Aug. 8; 26(15):3558-69). Additionally, symmetric dimethylation of H2AR3 has been implicated in the silencing of differentiation genes in embryonic stem cells (Tee W W, et al. Prmt5 is essential for early mouse development and acts in the cytoplasm to maintain ES cell pluripotency. Genes Dev. 2010 Dec. 15; 24(24):2772-7). PRMT5 also plays a role in cellular signaling, through the methylation of EGFR and PI3K (Hsu J M, et al. Crosstalk between Arg 1175 methylation and Tyr 1173 phosphorylation negatively modulates EGFR-mediated ERK activation. Nat Cell Biol. 2011 February; 13(2):174-81; Wei T Y, Juan C C, Hisa J Y, Su L J, Lee Y C, Chou H Y, Chen J M, Wu Y C, Chiu S C, Hsu C P, Liu K L, Yu C T. Protein arginine methyltransferase 5 is a potential oncoprotein that upregulates G1 cyclins/cyclin-dependent kinases and the phosphoinositide 3-kinase/AKT signaling cascade. Cancer Sci. 2012 September; 103(9):1640-50.). The role of PRMT5 in the methylation of proteins involved in cancer-relevant pathways is described below.

PRMT5 Knockout Models

Complete loss of PRMT5 is embryonic lethal. PRMT5 plays a critical role in embryonic development which is demonstrated by the fact that PRMT5-null mice die between embryonic days 3.5 and 6.5 (Tee W W, et al. Prmt5 is essential for early mouse development and acts in the cytoplasm to maintain ES cell pluripotency. Genes Dev. 2010 Dec. 15; 24(24):2772-7). Early studies suggest that PRMT5 plays an important role in HSC (hematopoietic stem cells) and NPC (neural progenitor cells) development. Knockdown of PRMT5 in human cord blood CD34$^+$ cells leads to increased erythroid differentiation (Liu F, et al. JAK2V617F-mediatedphosphorylation of PRMT5 down-regulates its methyltransferase activity and promotes myeloproliferation. Cancer Cell. 2011 Feb. 15; 19(2):283-94). In NPCs, PRMT5 regulates neural differentiation, cell growth and survival (Bezzi M, et al. Regulation of constitutive and alternative splicing by PRMT5 reveals a role for Mdm4 pre-mRNA in sensing defects in the spliceosomal machinery. Genes Dev. 2013 Sep. 1; 27(17):1903-16).

PRMT5 in Cancer

Increasing evidence suggests that PRMT5 is involved in tumorigenesis. PRMT5 protein is overexpressed in a number of cancer types, including lymphoma, glioma, breast and lung cancer and PRMT5 overexpression alone is sufficient to transform normal fibroblasts (Pal S, et al. Low levels of miR-92b/96 induce PRMT5 translation and H3R8/H4R3 methylation in mantle cell lymphoma. EMBO J. 2007 Aug. 8; 26(15):3558-69; Ibrahim R, et al. Expression of PRMT5 in lung adenocarcinoma and its significance in epithelial-mesenchymal transition. Hum Pathol. 2014 July; 45(7): 1397-405; Powers M A, et al. Protein arginine methyltransferase 5 accelerates tumor growth by arginine methylation of the tumor suppressor programmed cell death 4. Cancer Res. 2011 Aug. 15; 71(16):5579-87; Yan F, et al. Genetic validation of the protein arginine methyltransferase PRMT5 as a candidate therapeutic target in glioblastoma. Cancer Res. 2014 Mar. 15; 74(6):1752-65). Knockdown of PRMT5 often leads to a decrease in cell growth and survival in cancer cell lines. In breast cancer, high PRMT5 expression, together with high PDCD4 (programmed cell death 4) levels predict overall poor survival (Powers M A, et al. Protein arginine methyltransferase 5 accelerates tumor growth by arginine methylation of the tumor suppressor programmed cell death 4. Cancer Res. 2011 Aug. 15; 71(16):5579-87). PRMT5 methylates PDCD4 altering tumor-related functions. Co-expression of PRMT5 and PDCD4 in an orthotopic model of breast cancer promotes tumor growth. High expression of PRMT5 in glioma is associated with high tumor grade and overall poor survival and PRMT5 knockdown provides a survival benefit in an orthotopic glioblastoma model (Yan F, et al. Genetic validation of the protein arginine methyltransferase PRMT5 as a candidate therapeutic target in glioblastoma. Cancer Res. 2014 Mar. 15; 74(6):1752-65). Increased PRMT5 expression and activity contribute to silencing of several tumor suppressor genes in glioma cell lines.

Figure 28:
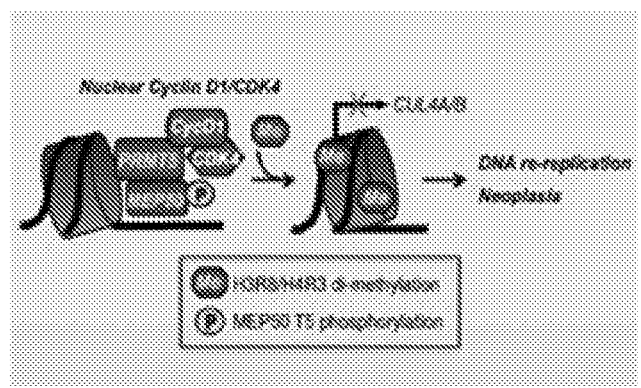
FIG. 28: Molecular relationship between PRMT5/MEP50 complex activity and cyclin D1 oncogene driven pathways. MEP50, a PRMT5 coregulatory factor is a cdk4 substrate, MEP50 phosphorylation increases PRMT5/MEP50 activity. Increased PRMT5 activity mediates key events associated with cyclin D1-dependent neoplastic growth, including CUL4 (Cullin 4) repression, CDT1 overexpression, and DNA re-replication (adapted from Aggarwal P, et al. Nuclear cyclin D1/CDK4 kinase regulates CUL4 expression and triggers neoplastic growth via activation of the PRMT5 methyltransferase. Cancer Cell. 2010 Oct. 19; 18(4):329-40).

The strongest mechanistic link currently described between PRMT5 and cancer is in mantle cell lymphoma (MCL). PRMT5 is frequently overexpressed in MCL and is highly expressed in the nuclear compartment where it increases the levels of histone methylation and silences a subset of tumor suppressor genes. Recent studies uncovered the role of miRNAs in the upregulation of PRMT5 expression in MCL. More than 50 miRNAs are predicted to anneal to the 3' untranslated region of PRMT5 mRNA. It was reported that miR-92b and miR-96 levels inversely correlate with PRMT5 levels in MCL and that the downregulation of these miRNAs in MCL cells results in the upregulation PRMT5 protein levels. Cyclin D1, the oncogene that is translocated in the vast majority of MCL patients, associates with PRMT5 and through a cdk4-dependent mechanism increases PRMT5 activity (FIG. 28, Aggarwal P, et al. Cancer Cell. 2010 Oct. 19; 18(4):329-40). PRMT5 mediates the suppression of key genes that negatively regulate DNA replication allowing for cyclin D1-dependent neoplastic growth. PRMT5 knockdown inhibits cyclin D1-dependent cell transformation causing death of tumor cells. These data highlight the important role of PRMT5 in MCL and suggest that PRMT5 inhibition could be used as a therapeutic strategy in MCL.

In other tumor types, PRMT5 has been postulated to play a role in differentiation, cell death, cell cycle progression, cell growth and proliferation. While the primary mechanism linking PRMT5 to tumorigenesis is unknown, emerging data suggest that PRMT5 contributes to regulation of gene expression (histone methylation, transcription factor binding, or promoter binding), alteration of splicing, and signal transduction. PRMT5 methylation of the transcription factor E2F1 decreases its ability to suppress cell growth and promote apoptosis (Zheng S, et al. Arginine methylation-dependent reader-writer interplay governs growth control by E2F-1. Mol Cell. 2013 Oct. 10; 52(1):37-51). PRMT5 also methylates p53 (Jansson M, et al. Arginine methylation regulates the p53 response. Nat Cell Biol. 2008 December; 10(12):1431-9) in response to DNA damage and reduces the ability of p53 to induce cell cycle arrest while increasing p53-dependent apoptosis. These data suggest that PRMT5 inhibition could sensitize cells to DNA damaging agents through the induction of p53-dependent apoptosis.

In addition to directly methylating p53, PRMT5 upregulates the p53 pathway through a splicing-related mechanism. PRMT5 knockout in mouse neural progenitor cells results in the alteration of cellular splicing including isoform switching of the MDM4 gene (Bezzi M, et al. Regulation of constitutive and alternative splicing by PRMT5 reveals a role for Mdm4 pre-mRNA in sensing defects in the spliceosomal machinery. Genes Dev. 2013 Sep. 1; 27(17):1903-16). Bezzi et al. discovered that PRMT5 knockout cells have decreased expression of a long MDM4 isoform (resulting in a functional p53 ubiquitin ligase) and increased expression of a short isoform of MDM4 (resulting in an inactive ligase). These changes in MDM4 splicing result in the inactivation of MDM4, increasing the stability of p53 protein, and subsequently, activation of the p53 pathway and cell death. MDM4 alternative splicing was also observed in PRMT5 knockdown cancer cell lines. These data suggest PRMT5 inhibition could activate multiple nodes of the p53 pathway.

In addition to the regulation of cancer cell growth and survival, PRMT5 is also implicated in the epithelial-mesenchymal transition (EMT). PRMT5 binds to the transcription factor SNAIL, and serves as a critical co-repressor of E-cadherin expression; knockdown of PRMT5 results in the upregulation of E-cadherin levels (Hou Z, et al. The LIM protein AJUBA recruits protein arginine methyltransferase 5 to mediate SNAIL-dependent transcriptional repression. Mol Cell Biol. 2008 May; 28(10):3198-207).

These data highlight the role of PRMT5 as a critical regulator of multiple cancer-related pathways and suggest that PRMT5 inhibitors could have broad activity in heme and solid cancers. There is a strong rationale for PRMT5 inhibitors as a therapeutic strategy in MCL, as well as breast and brain cancers. These data also underline the mechanistic rationale for the use of PRMT5 inhibitors in an appropriate cellular context to:

inhibit cyclin D1-dependent functions in MCL;
  activate and modulate p53 pathway activity;
  modulate E2F1-dependent cell growth and apoptotic functions;
  de-repress E-cadherin expression;

Compound C is a medium molecular weight (MW=452.55) potent, selective, peptide competitive, reversible inhibitor of the PRMT5/MEP50 complex with good overall physical properties and oral bioavailability. Compound C impacts several cancer related pathways ultimately leading to potent anti-cancer activity in both in vitro and in vivo models, providing a novel therapeutic mechanism for the treatment of MCL, breast and brain cancers.

Biochemistry

Compound C was profiled in a number of in vitro biochemical assays to characterize the potency, reversibility, selectivity, and mechanism of inhibition of PRMT5.

Figure 29:
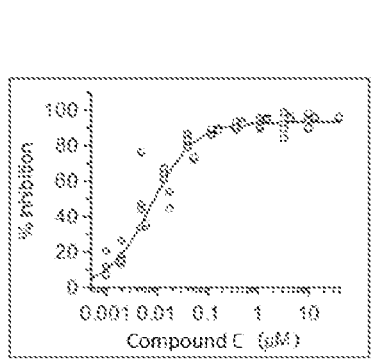
FIG. 29: Compound $IC_{50}$ values against PRMT5/MEP50. PRMT5/MEP50 (4 nM) activity was monitored using a radioactive assay under balanced conditions (substrate concentrations at $K_{m\ apparent}$) measuring the transfer of $^3H$ from SAM to an H4 peptide following treatment with Compound C, Compound F, Compound B, or Compound E. $IC_{50}$ values were determined by fitting the data to a 3-parameter dose-response equation.

The inhibitory potency of Compound C was assessed using a radioactive assay measuring $^3$H transfer from SAM to a peptide derived from histone H4 identified from a histone peptide library screen. A long reaction time, 120 minutes, was used to capture any time-dependent increase in potency. Compound C was found to be a potent inhibitor of PRMT5/MEP50 with an $IC_{50}$ of 8.7±5 nM (n=3). This potency approaches the tight-binding limit of the assay (2 nM) and therefore represents an upper limit to the true potency of the molecule (FIG. 29). The inhibitory potency was similar for close analogs of Compound C including Compound F, Compound B and Compound E (key differences on the left hand side of the molecule) which were used as tool compounds in some biology studies.

To assess the ability of Compound C to inhibit the PRMT5 dependent methylation of cellular substrates other than histone H4, a panel of PRMT5 substrates was assembled for evaluation including SmD3, Lsm4, hnRNPH1 and FUBP1 (the majority of these substrates involved in splicing and transcriptional silencing were discovered through a cellular Methylscan™ study described below in the Biology section). Compound C effectively inhibited PRMT5/MEP50 catalyzed methylation of all of these substrates although the extremely low $K_{m\ apparent}$ precluded an accurate determination of potency.

To enable interpretation of safety studies, the potency of Compound C was also evaluated against the rat and dog orthologs of the PRMT5/MEP50 complex under similar conditions as the human PRMT5 assay. Compound C potency varied<3-fold against all species (Table 7).

TABLE 7

PRMT5/MEP50 activity was monitored using a radioactive assay under balanced conditions (substrate concentrations at $K_{m\ apparent}$) measuring the transfer of $^3$H from SAM to protein substrate following treatment with Compound C. $IC_{50}$ values were determined by fitting the data to a 3-parameter dose-response equation.

| Species of PRMT5/MEP50 | Compound C $IC_{50}$ (nM) |
|---|---|
| Human | 9.8 ± 6 |
| Rat | 16.2 ± 5 |
| Dog | 21.2 ± 5 |

Figure 30:
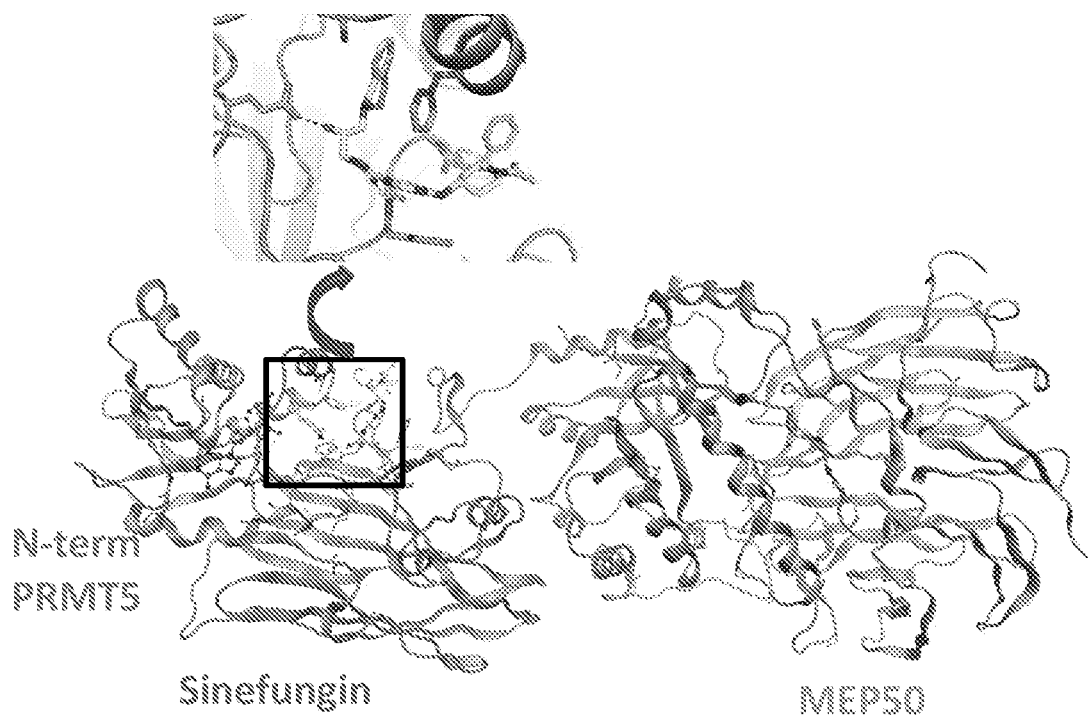
FIG. 30: The crystal structure resolved at 2.8 for PRMT5/MEP50 in complex with Compound C and sinefungin. The inset reveals that the compound is bound in the peptide binding pocket and makes key interactions with the PRMT5 backbone.

To determine the mechanism of inhibition and inhibitor binding mode, Compound C was co-crystalized with the PRMT5/MEP50 complex and sinefungin, a natural product SAM analugue (2.8 Å resolution) (FIG. 30). The inhibitor binds in the cleft normally occupied by the substrate peptide and in close proximity to sinefungin which occupies the SAM pocket. The aryl ring of the tetrahydroisoquinoline appears to make a 7-aryl stacking interaction with the amino group of sinefungin. A hydrogen bond is formed between the hydroxyl group of Compound C and the Leu437 backbone and Glu244. A hydrogen bond interaction is also formed between the amide of the pyrimidine ring and the backbone NH group of Phe580. The terminal piperidine acetamide lies on the solvent exposed surface with no obvious critical contacts. Overall, the structure supports an inhibitory mechanism that is uncompetitive with SAM and competitive with substrate.

To determine whether Compound C is a reversible inhibitor of PRMT5/MEP50 and to further explore the inhibitory mechanism, affinity selection mass spectrometry (ASMS) was used to measure the binding of Compound C to various PRMT5/MEP50 complexes. Positive binding could be detected in the binary complexes containing PRMT5/MEP50 with SAM, sinefungin or SAH and to the dead-end tertiary complexes of PRMT5/MEP50:H4 peptide: SAH or sinefungin. As ASMS would be unable to detect irreversibly bound Compound C, these results are consistent with a reversible binding mechanism. Upon competition with 10-fold excess H4 peptide the binding of Compound C was reduced within the PRMT5/MEP50:H4 peptide: sinefungin complex. No binding of Compound C was detected with the PRMT5/MEP50: H4 peptide complex or with PRMT5/MEP50 alone suggesting the SAM binding pocket needs to be occupied for Compound C binding. These results best fit an inhibitory mechanism that is uncompetitive with SAM and competitive with H4 peptide.

Figure 31:
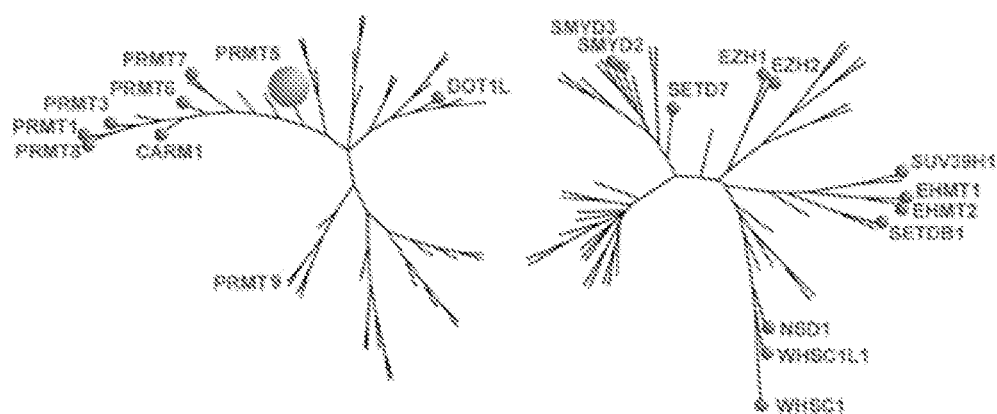
FIG. 31: Phylogenetic tree highlighting the methyltransferases tested in the selectivity panel. Compound C showed much greater potency for PRMT5 (▒, $10^{-8}$ M) than for any other tested enzyme (* $>10^{-5}$ M). PRMT9 is shown for relationship purposes only within the family tree and was not evaluated in the panel. Figure adapted from Richon V M. et al.

The selectivity of Compound C was assessed in a panel of enzymes that included Type I and Type II PRMTs and lysine methyltransferases (KMTs). PRMT9/FBXO11, which is the other Type II PRMT and the only PRMT to lack the THW loop, was not included due to the lack of a functional enzyme assay. Compound C did not inhibit any of the 19 enzymes on the methyltransferase selectivity panel with $IC_{50}$ values>40 µM resulting in >4000-fold selectivity for PRMT5/MEP50 (FIG. 31). Selectivity for PRMT5/MEP50 over the other methyltransferases was also observed for PRMT5 tool compounds that were used in the Biology section of this document (Compound B, Compound F and Compound E).

In summary, Compound C is a potent, selective, reversible inhibitor of the PRMT5/MEP50 complex with an $IC_{50}$ of 8.7 5 nM. The crystal structure of PRMT5/MEP50 in complex with Compound C and the ASMS binding data are consistent with a SAM uncompetitive, protein substrate competitive mechanism.

Biology
Summary

PRMT5 is overexpressed in a number of human cancers and is implicated in multiple cancer-related pathways. There is a strong rationale for use of PRMT5 inhibitors as a therapeutic strategy in MCL, as well as breast and brain cancers. To understand the scope of PRMT5 inhibitor anti-proliferative activity, Compound C was profiled in various in vitro and in vivo tumor models using 2D and 3D growth assays.

The identity of the genes and pathways impacted by PRMT5 inhibition are critical to understanding the mechanism of PRMT5 inhibitors required for indication prioritization, discovery of predictive biomarkers and the design of rational combination studies. Several in vitro mechanistic studies were performed to assess the biology of the response to PRMT5 inhibition. Arginine methylation levels of a number of PRMT5 substrates were assessed to monitor Compound C activity against PRMT5 in cells and xenograft tumors. RNA-sequencing of a number of cell lines was performed to evaluate the effects of Compound C on gene expression, splicing, and other molecular mechanisms and pathways that are regulated by PRMT5 activity. p53 pathway activity was monitored in cell lines treated with PRMT5 inhibitors.

Finally, Compound C activity was tested in several xenograft models of MCL and breast cancer to assess the efficacy of PRMT5 inhibition in pre-clinical cancer models and evaluate molecular mechanisms and potential biomarkers of response.

Cell Line Sensitivity

Figure 32:
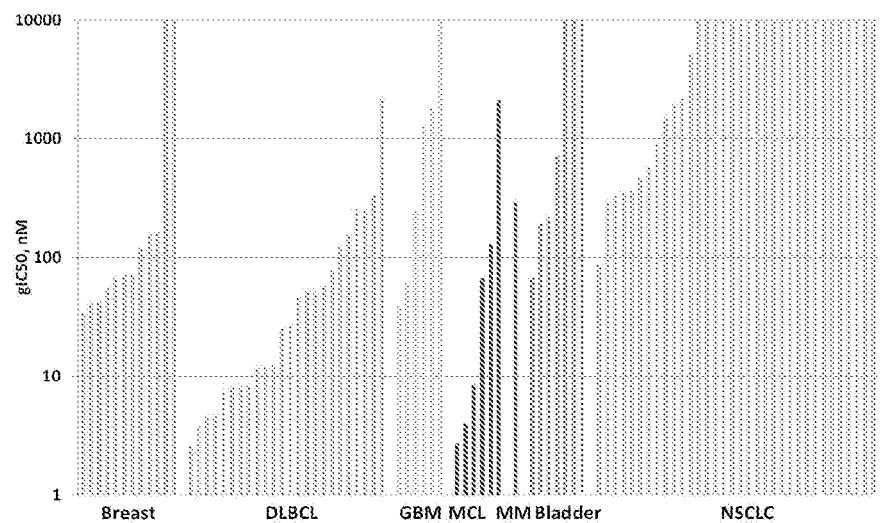
FIG. 32: Compound C $gIC_{50}$ values from a 6-day growth/death assay in a panel of cancer cell lines. DLBCL-diffuse large B-cell lymphoma, GBM-glioblastoma, MCL-mantle cell lymphoma, MM-multiple myeloma

To assess the anti-proliferative activity of PRMT5 inhibition in various tumor types, Compound C was profiled in 2D and 3D in vitro assays using broad panels of cancer lines and patient-derived tumor models. First, Compound C was evaluated in a panel of cancer cell lines in a 2D 6 day growth/death assay (FIG. 32). The cell lines were selected to represent tumor types where PRMT5 activity has been reported to regulate key pathways and/or cell growth and survival (such as lymphoma and MCL, glioma, breast and lung cancer lines). Overall, the majority of cell lines tested exhibited $gIC_{50}$ values below 1 µM, while the most sensitive lymphoma lines (mantle cell lymphoma and diffuse large B-cell lymphoma cell lines) had $gIC_{50}$ values in the single digit nM range.

Figure 33:
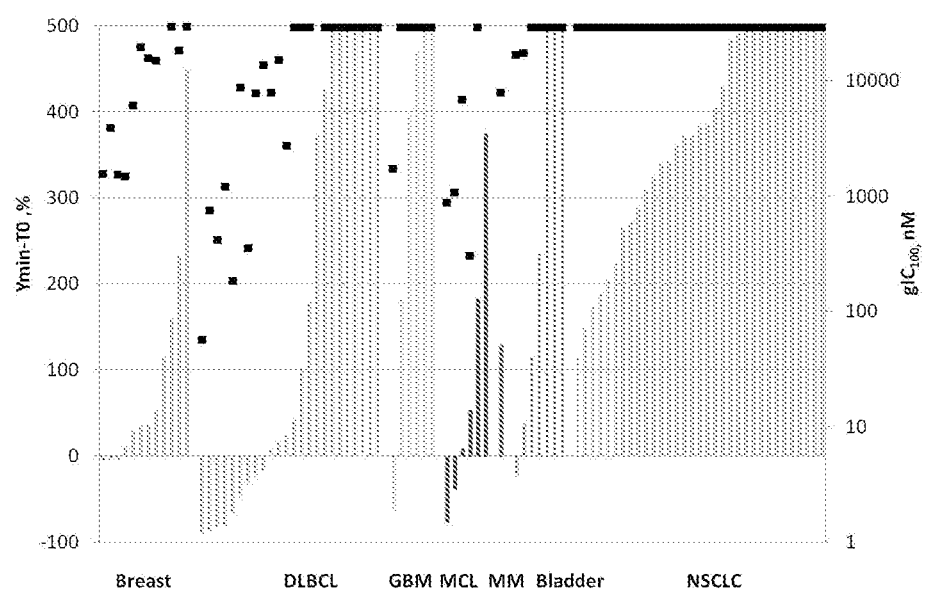
FIG. 33: Compound C $gIC_{100}$ (black squares) and $Y_{min}$-T0 (bars) values from a 6-day growth/death assay in a panel of cancer cell lines (top concentration used in this assay was 30 µM). DLBCL-diffuse large B-cell lymphoma, GBM-glioblastoma, MCL-mantle cell lymphoma, MM-multiple myeloma

Compound C induced a cytotoxic response in a subset of diffuse large B-cell lymphoma (DLBCL), mantle cell lymphoma (MCL), glioblastoma, breast and bladder cancer cell lines at concentrations above 100 nM in a 6-day growth/death assay (FIG. 33, negative $Y_{min}$-T0 values). Overall, MCL and DLBLC lines exhibited the strongest cytotoxic response. The majority of breast cancer lines had low $Y_{min}$-T0 values, suggesting that PRMT5 inhibition results in a complete growth inhibition in breast cancer models, while the rest of the cell lines exhibited a partial cytostatic response (positive $Y_{min}$-T0 values).

Figure 34:
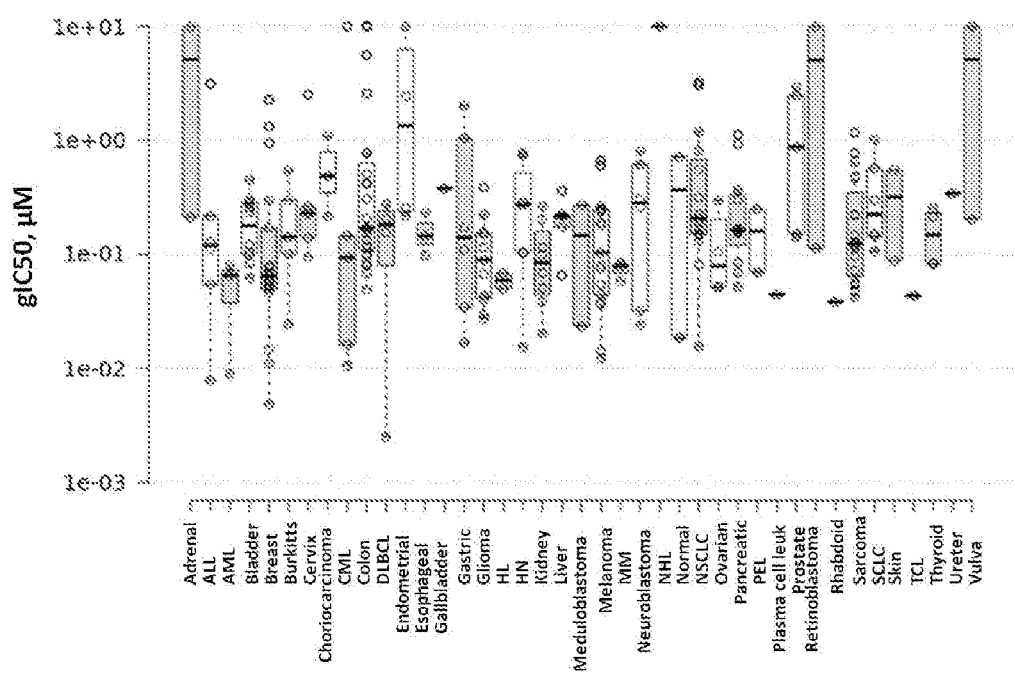
FIG. 34: Compound B $gIC_{50}$ values in cancer cell lines (n=240) from 10 day 2D growth assay. ALL-acute lymphoblastic leukemia, AML-acute myeloid leukemia, CML-chronic myeloid leukemia, DLBCL-diffuse large B-cell lymphoma, HL-Hodgkin lymphoma, HN-head and neck cancer, MM-multiple myeloma, NHL-non-Hodgkin lymphoma, NSCLC-non-small cell lung cancer, PEL-primary effusion lymphoma, SCLC-small cell lung cancer, TCL-T-cell lymphoma.

The anti-proliferative activity of PRMT5 inhibition was further tested in a large cancer cell line screen (240 cell lines, 10-day 2D growth assay) performed with a PRMT5 tool molecule (FIG. 34, biochemical/cellular activity comparison of Compound C and Compound B in FIG. 29). Overall, the majority of cell lines exhibited $gIC_{50}$ values lower than 1 µM. The tumor types with median $gIC_{50}$<100 nM were acute myeloid leukemia (AML), chronic myelogenous leukemia (CML), Hodgkin's Lymphoma (HL), multiple myeloma (MM), breast, glioma, kidney, melanoma, and ovarian cancer. These data suggest that PRMT5 inhibitors exhibit a broad range of anti-proliferative activity against various heme and solid tumor types.

Figure 35:
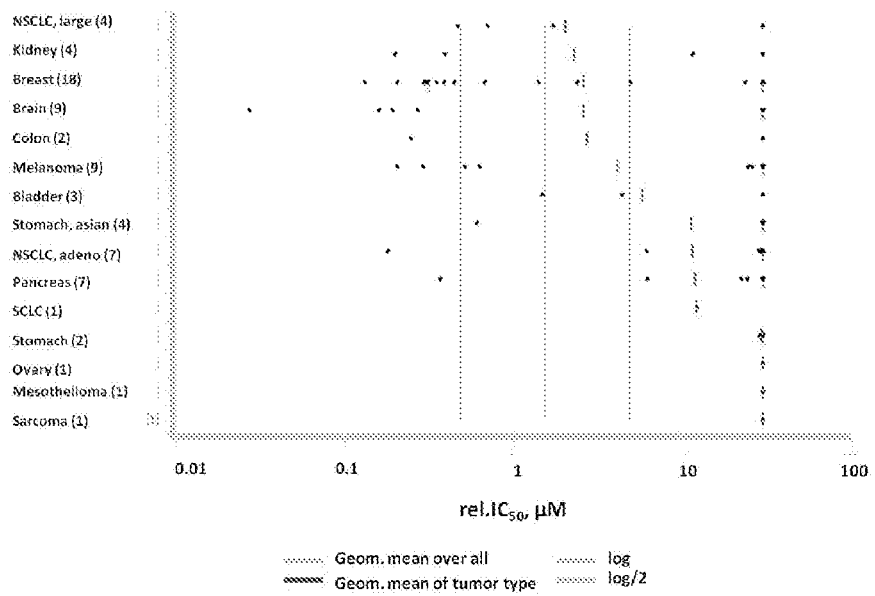
FIG. 35: Compound E relative $IC_{50}$ values from 8-13 day colony formation assay performed in patient-derived and cell line tumor models.

A similar broad range of anti-growth effects was observed with a PRMT5 tool compound in a panel of patient-derived tumor models and cell lines (n=73) in a soft agar 3D colony formation assay (FIG. 35). Relative growth $IC_{50}$ values below 1 µM were observed in 37% of the models, including tumors of non-small cell lung cancer (NSCLC), breast, melanoma, colon and glioma. Tumor types with the lowest median $IC_{50}$ values were large cell lung cancer, breast, kidney and glioma.

Overall, these data demonstrate that PRMT5 inhibitors have potent anti-proliferative activity in a variety of solid and hematological cancer models. The following indications were selected for additional investigation based on the activity observed in the above studies, literature hypotheses and potential for clinical development:

MCL and DLBCL (potent anti-proliferative and cytotoxic responses to PRMT5 inhibition)

Breast cancer (low $gIC_{50}$ values and complete growth inhibition in cell lines and low $IC_{50}$ values in colony formation assays in the panel of patient-derived models)

Glioblastoma (low $IC_{50}$ values in colony formation assay).

Lymphoma Biology

As mentioned above, Compound C induced a potent cytotoxic response in a subset of mantle cell and diffuse large B-cell lymphoma cell lines (FIGS. 32-33). Since PRMT5 is frequently overexpressed in MCL and plays an important role in MCL pathways (such as cyclin D1 and p53), Compound C activity and mechanism were assessed in several cellular mechanistic studies. Compound C efficacy was evaluated in two xenograft models of mantle cell lymphoma.

Cellular Mechanistic Data (Lymphoma)

SDMA Inhibition

PRMT5 is responsible for the vast majority of cellular symmetric arginine dimethylation. To better understand the biological mechanisms linking PRMT5 inhibition to anticancer phenotypes, substrates were identified using an SDMA antibody recognizing a subset of cellular proteins that are symmetrically dimethylated at arginine residues. The identities of the proteins detected by the SDMA antibody were determined in Z138 cellular lysates (from control and PRMT5 inhibitor treated cells) by immunoprecipitating with the SDMA antibody and mass-spectrometric analysis (Methylscan™). Amongst SDMA containing proteins the vast majority were factors that are involved in cellular splicing and RNA processing (SmB, Lsm4, hnRNPH1 and others), transcription (FUBP1) and translation, highlighting the role of PRMT5 as an important regulator of cellular RNA homeostasis.

Figure 36:
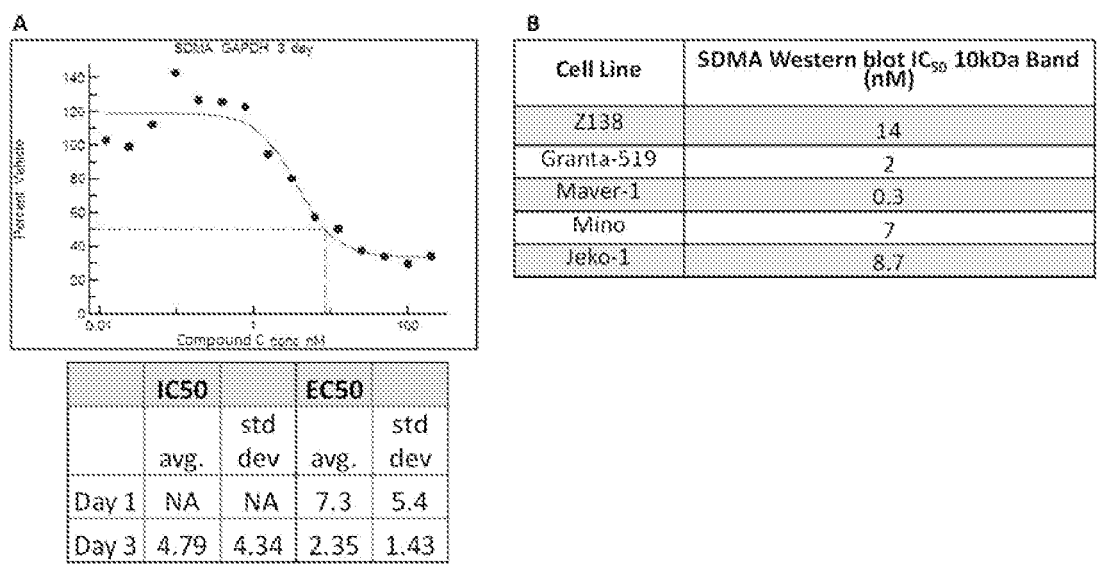
FIG. 36: Compound C inhibition of SDMA. (A) A representative SDMA dose-response curve (total SDMA normalized to GAPDH) on day 3 (top) and $IC_{50}$ values from Z138 cells on days 1 and 3 (bottom). (B) SDMA $IC_{50}$ values in a panel of MCL lines (EPIZYME data, day 4).

The SDMA antibody was then used in western and ELISA assays to measure Compound C dependent inhibition of methylation. First, Z138 MCL cells (Compound C $gIC_{50}$ 2.7 nM, $gIC_{95}$ 82 nM and $gIC_{100}$ 880 nM, cytotoxic response in a 6-day growth/death assay, FIGS. 32-33) were treated with increasing concentrations of Compound C to determine the cellular $IC_{50}$ of SDMA inhibition on days 1 and 3 post treatment (FIG. 36). An SDMA ELISA revealed time-dependent changes in SDMA levels with $IC_{50}$ values of 4.79 nM on day 3 and $EC_{50}$ of 7.3 and 2.35 on days 1 and 3, respectively (FIG. 36, panel A). Complete inhibition of SDMA was observed at concentrations above 19 nM ($EC_{90}$) on day 3. Complete growth inhibition in Z138 cells as observed between $gIC_{95}$ (82 nM) and $gIC_{100}$ (880 nM) (in a 6-day growth/death assay), concentrations that are above the $EC_{90}$ of SDMA inhibition. These data suggest that in order to trigger complete growth inhibition and cytotoxicity in Z138 cells, PRMT5 activity needs to be inhibited>90%.

In order to evaluate whether the inhibition of SDMA levels is predictive of cellular growth response to Compound C, SDMA $IC_{50}$ values were determined in a panel of MCL cell lines. SDMA $IC_{50}$ values were in a range of 0.3 to 14 nM in a panel of 5 MCL lines (FIG. 36, panel B) (sensitive Z138, Granta-519, Maver-1 and moderately resistant Mino, and Jeko-1, FIGS. 32-33) suggesting that SDMA is not a response marker, but rather a marker of PRMT5 activity that could be used to monitor PRMT5 inhibition in sensitive and resistant models.

Gene Expression Profiling of Lymphoma Cell Lines

PRMT5 methylates histones and proteins involved in RNA processing and therefore PRMT5 inhibition is expected to have a profound effect on cellular mRNA homeostasis. To further decipher cellular mechanisms that are regulated by PRMT5 and contribute to the cellular response to PRMT5 inhibitors, global gene expression changes were evaluated in lymphoma models sensitive to PRMT5 inhibition. To elucidate gene expression changes that occur in lymphoma cell lines upon PRMT5 inhibitor treatment, 4 sensitive lymphoma lines (2 MCL lines-Z138 and Granta-519 and 2 DLBCL lines-DOHH2 and RL) were profiled by RNA-sequencing.

Figure 37:
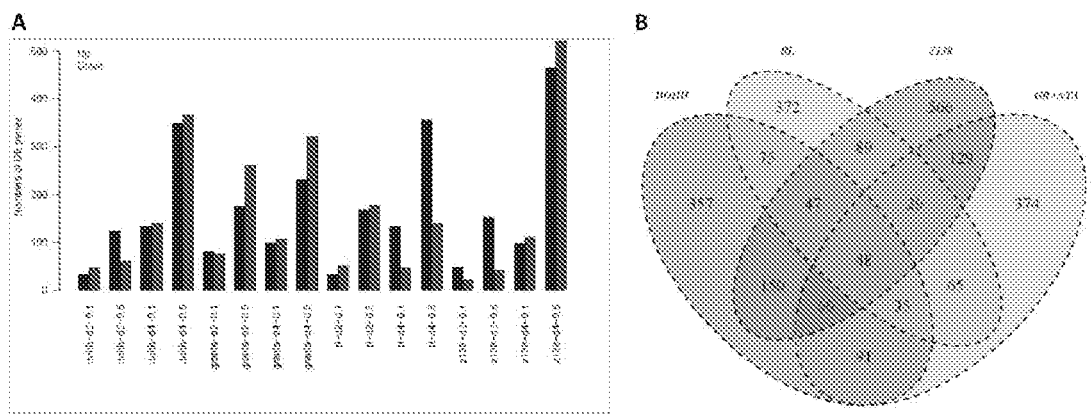
FIG. 37: Gene expression changes in lymphoma cell lines treated with a PRMT5 inhibitor. A. Quantification of differentially expressed (DE) genes in lymphoma cell lines after Compound B (0.1 and 0.5 µM) treatment (days 2 and 4). B. Overlap of DE genes across lymphoma lines.

Gene expression changes were evaluated in lymphoma lines treated with increasing concentrations of PRMT5 tool molecule for 2 and 4 days (FIG. 37). The effect on RNA expression was time- and dose-dependent and 48 genes were commonly regulated across 4 lymphoma lines. These data demonstrate that PRMT5 inhibition triggers expression changes in several hundred of genes and a subset of these changes is common for all 4 sensitive lymphoma lines tested. The relevance of these genes in the mechanism of cellular response to PRMT5 inhibition is being evaluated.

SDMA and Gene Expression Changes

Figure 38:
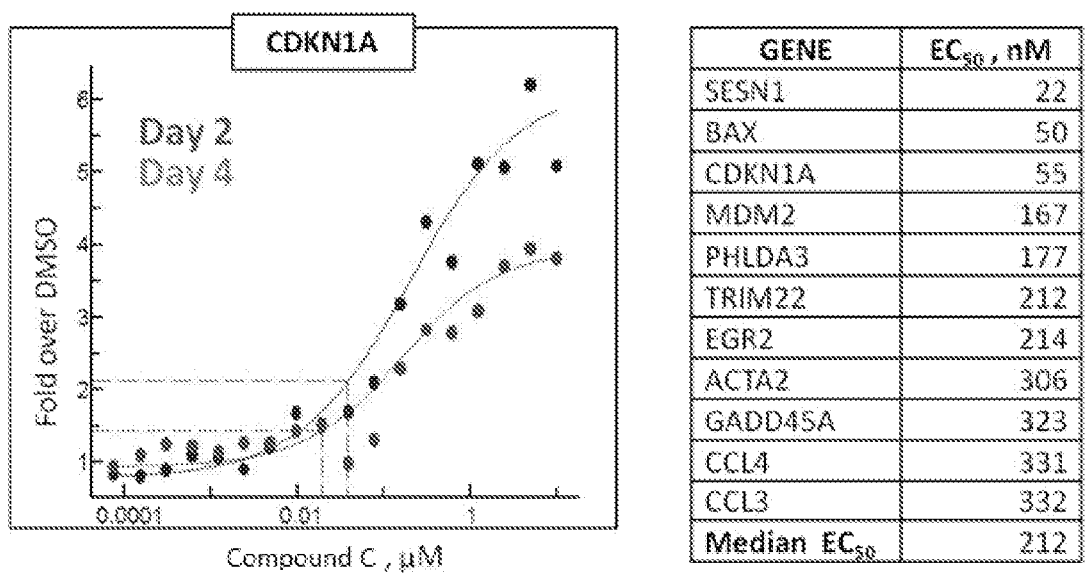
FIG. 38: Compound C gene expression $EC_{50}$ values in a panel of 11 genes identified by RNA-sequencing. Representative dose-response curves for CDKN1A (days 2 and 4, left panel) and gene panel $EC_{50}$ summary table (right panel, day 4).

To confirm the gene expression changes discovered by the RNA-seq experiment, qPCR analysis of the expression of a subset of genes was performed (genes with robust changes and genes involved in p53 pathway). Z138 cells were treated with increasing doses of Compound C for 2 and 4 days, RNA was isolated and analyzed by qPCR. FIG. 38 shows representative dose-response curves in the left panel and gene expression $EC_{50}$ values (day 4) are summarized in the right panel. Overall, all 11 genes tested showed time- and dose-dependent expression changes and the $EC_{50}$ values were in the range of 22 to 332 nM, with a median gene expression $EC_{50}$ of 212 nM. Importantly, the gene expression median $EC_{50}$ value corresponds to the Compound C concentration that results in the maximal inhibition of cellular methylation in Z138 (as measured by SDMA antibody ELISA, FIG. 36), suggesting that near complete inhibition of PRMT5 activity is required to establish changes in the gene expression program. These data highlight the connection of the extent of PRMT5 inhibition with changes in gene expression and growth phenotypes, where both require near complete inhibition of PRMT5 activity.

PRMT5 Inhibition and Splicing

Since PRMT5 methylates spliceosome subunits and PRMT5 inhibition attenuates arginine methylation of a number of proteins involved in splicing, the effect of PRMT5 inhibition on cellular splicing was studied. The changes in RNA splicing were assessed in the lymphoma RNA-seq dataset described above.

Figure 39:
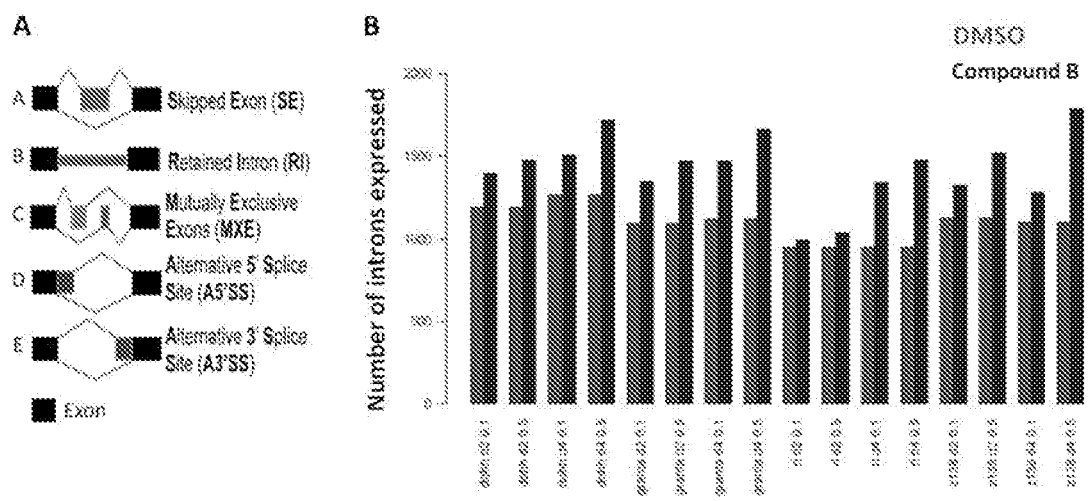
FIG. 39: Compound B attenuates the splicing of a subset of introns in lymphoma cell lines. A. Mechanisms of regulation of cellular splicing (adapted from Bezzi M. et al.). B. Analysis of intron expression in lymphoma lines treated with 0.1 or 0.5 µM Compound B.
Figure 40:
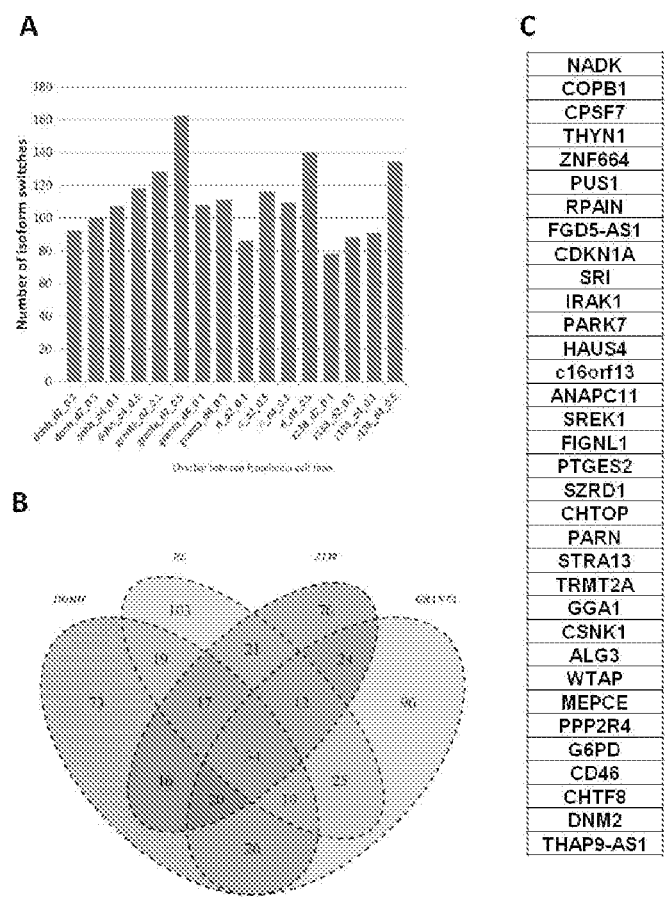
FIG. 40: Compound B induces isoform switching for a subset of genes in lymphoma cell lines. A. Quantification of isoform switches in 4 lymphoma cell lines treated with Compound B (0.1 and 0.5 µM) for 2 and 4 days. B. Overlap of isoform switches in 4 lymphoma lines. C. List of genes that undergo alternative splicing in all 4 lymphoma lines (overlap of 4 cell lines).

There are several molecular mechanisms by which cellular splicing might be regulated (FIG. 39, panel A), where retention of introns (B) usually results in changes of gene expression, while exon skipping or the usage of alternative splice sites lead to isoform switching (A, C-E). PRMT5 tool compound treatment resulted in a dose- and time-dependent increase of intron retention in all lymphoma lines tested (FIG. 39, panel B). Interestingly, splicing factor map analysis suggested that a subset of splicing factors binding sites were enriched at retained introns across all four cell lines, including hnRNPH1 (directly methylated by PRMT5), hnRNPF, SRSF1 and SRSF5, suggesting that PRMT5 effects on cellular splicing might be dependent on the methylation of multiple components of spliceosome machinery (Sm and hnRNP proteins). PRMT5 inhibition also induced isoform switching (alternative splicing) in lymphoma cell lines (FIG. 40, panel A) and 34 genes showed consistent alternative splicing changes across all cell lines tested (FIG. 40, panels B and C).

Overall, changes in the splicing of several hundred genes were observed, highlighting that PRMT5 effects on splicing are not global, but rather are specific to a limited number of RNAs. One likely explanation for such specificity could be that PRMT5 directly regulates RNA binding of specific splicing factors, such as hnRNPH1 and others. The role of alternative splicing changes in the mechanism of action of PRMT5 inhibitors is being explored and one particular example is discussed in the section below.

MDM4 Splicing and Activation of the p53 Pathway

Figure 41:
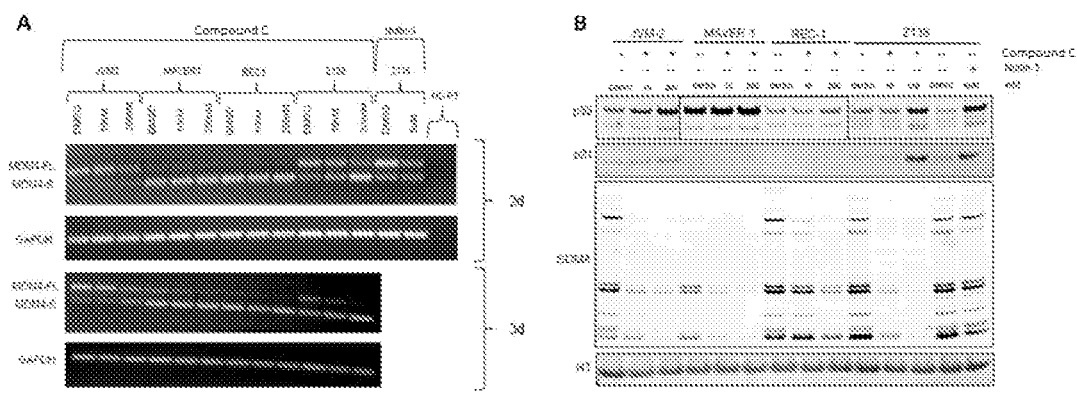
FIG. 41: MDM4 alternative splicing and p53 activation in MCL lines treated with Compound C. A. MDM4 isoform expression analysis in a panel of 4 mantle cell lymphoma lines treated with 10 and 200 nM Compound C or 5 µM Nutlin-3 for 2 and 3 days (MDM4-FL-long; MDM4-S-short). B. Western analysis of p53 and p21 expression in MCL lines treated with 10 and 200 nM Compound C or 5 µM Nutlin-3 for 3 days.

It has been reported that PRMT5 knockout or knockdown results in an MDM4 isoform switch, which leads to the inactivation of MDM4 ubiquitin ligase activity toward p53 (described in the BACKGROUND section). PRMT5 inhibition resulted in the activation of the p53 pathway in 4 lymphoma lines tested in an RNA-seq experiment (GSEA). To understand whether p53 activation is associated with MDM4 isoform switching, MDM4 alternative splicing was analyzed. The MDM4 isoform switch was observed in all 4 lymphoma lines. Next, changes in MDM4 splicing were confirmed in a panel of 4 MCL lines by RT-PCR (FIG. 41, panel A, Z138, JVM-2 and MAVER-1 MCL lines are sensitive to Compound C, while REC-1 is the most resistant MCL line). In Z138 and JVM-2 cells (both p53 wild-type) Compound C induced MDM4 isoform switching. In MAVER-1 and REC-1 cells (both p53 mutant), the basal expression of the MDM4 long form was low/undetectable and therefore, MDM4 isoform switching could not be detected. Subsequently, p53 and p21 (or CDKN1A, a p53 target gene) protein expression increased in JVM-2 and Z138 cells (FIG. 41, panel B). Importantly, in Z138 cells, 200 nM Compound C and 5 M MDM2 inhibitor (Nutlin-3) treatment increased p53 and p21 expression to similar levels. These data suggest that PRMT5 inhibition regulates MDM4 splicing in cell lines that express high levels of the MDM4 long isoform and induces the p53 pathway activity in p53 wild-type cell lines. The role of the p53 pathway in the biology of the response of p53 wild-type MCL cells to PRMT5 inhibition is being evaluated.

Figure 42:
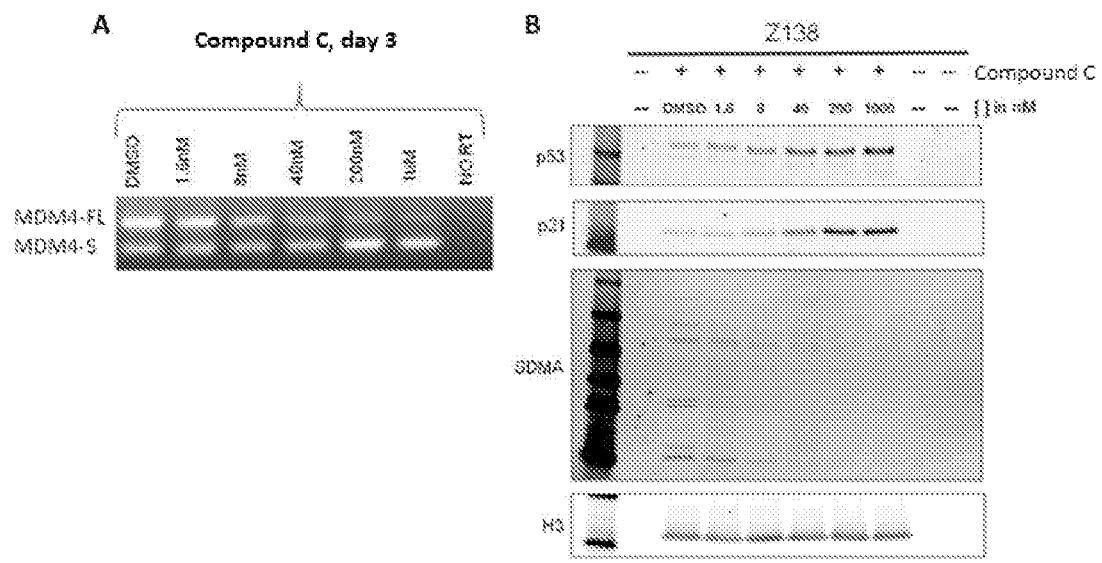
FIG. 42: Compound C induces dose-dependent changes in MDM4 RNA (A) splicing and SDMA/p53/p21 levels in Z138 cells (B).

Additionally, the dose-response of changes in MDM4 splicing, SDMA inhibition and p53 expression were evaluated in Z138 cells treated with increasing concentrations of Compound C to evaluate the relationship of PRMT5 inhibition, MDM4 splicing and p53 activation (FIG. 42, panel A and B). SDMA levels were undetectable by Western blot at the concentrations of Compound C above 8 nM. At the same time, changes in MDM4 splicing and p53/p21 protein expression were apparent at concentrations of Compound C above 8 nM. These results suggest that PRMT5 activity needs to be substantially inhibited (no SDMA levels detectable by Western) before changes in gene splicing and subsequent pathway activity will occur (MDM4/p53/p21).

These data suggest that PRMT5 inhibition activates wild-type p53 through the regulation of MDM4 splicing. Such a mechanism could be useful in cancer types where p53 is not frequently mutated, such as heme and pediatric malignancies. In lymphoma models, PRMT5 inhibition leads to significant (GSEA analysis) and relatively quick activation of the p53 pathway, which likely contributes to the growth/death phenotypes observed in cell lines treated with PRMT5 inhibitor. Knockdown/rescue experiments will be used to further evaluate the role of the MDM4/p53 pathway in the PRMT5 inhibitor induced cellular responses.

MDM4 isoform expression and p53 mutation are potential predictive biomarkers of response to PRMT5 inhibition in MCL. In an MCL cell line panel, the only two wild-type p53 lines, Z138 and JVM-2, were the most sensitive lines (the lowest $gIC_{50}$ values and the only two MCL lines that exhibit cytotoxicity in a 6-day growth/death assay). In both cell lines, Compound C treatment led to an MDM4 isoform switch and p53 pathway activation. The limited number of MCL cell lines and extremely low success rate of the establishment of primary MCL models precludes us from further evaluation of the p53 predictive biomarker hypothesis. While the p53 pathway could be important for the biology of the response of p53 wild-type cells to PRMT5 inhibitors, our data strongly underlines the importance of other pathways that can drive anti-tumor efficacy as well, since PRMT5 inhibition results in anti-proliferative effects in the absence of functional p53 (ex. Maver-1 cell line).

Mantle Cell Lymphoma: Comparison and Combination Activity of Compound C and Ibrutinib.

Figure 43:
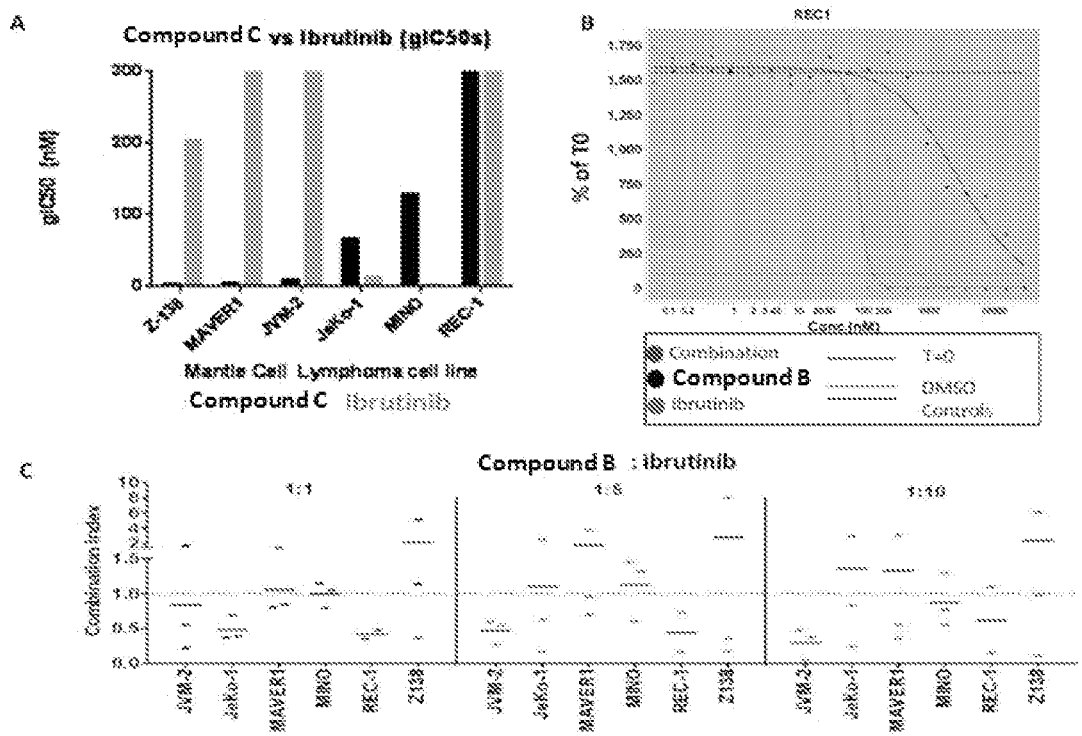
FIG. 43: Activity of PRMT5 inhibitor and ibrutinib as single agents and in combination in MCL cell lines. A. $gIC_{50}$ values for Compound C and ibrutinib in a 6-day growth/death CTG assay. B. Representative growth curve for the combination of Compound B and ibrutinib in REC1 cells (day 6, 1:1 ratio). C. Combination indexes (CI) for Compound B:ibrutinib in a 6-day growth/death CTG assay at the indicated ratios.

Bruton's tyrosine kinase (BTK) inhibitor ibrutinib was recently approved for use in MCL with an unprecedented overall response rate of nearly 70 percent in the relapsed/refractory setting (Wang M L, et al. N Engl J Med. 2013 Aug. 8; 369(6):507-16). The majority of patients treated with ibrutinib, however, do not achieve complete remission, and the median progression-free survival is approximately 14 months. To understand, whether Compound C could be used in ibrutinib resistant MCL, Compound C and ibrutinib sensitivity were assessed in a 6-day growth/death assay (FIG. 43, panel A). The cell lines that have low Compound C $gIC_{50}$ values (Z-138, Maver-1 and JVM-2) are resistant to ibrutinib, while ibrutinib sensitive lines (Mino, Jeko-1) are only moderately sensitive to Compound C (FIG. 43, panel A). This data suggests that the activity profiles of ibrutinib and Compound C do not overlap and that ibrutinib resistant MCL models are sensitive to PRMT5 inhibition. Additionally, the combination of PRMT5 inhibitor and ibrutinib demonstrated synergistic anti-proliferative activity in the majority of MCL lines tested (Combination Index (CI)<1) (FIG. 43, panels B and C), suggesting that the combination of the two compounds may provide increased therapeutic benefit. These data indicate that PRMT5 inhibitors could be used in an ibrutinib resistant MCL patient population and that the combination of PRMT5 inhibitors with ibrutinib could be explored in both ibrutinib refractory and sensitive settings.

Efficacy in Mantle Cell Lymphoma Models

Figure 44:
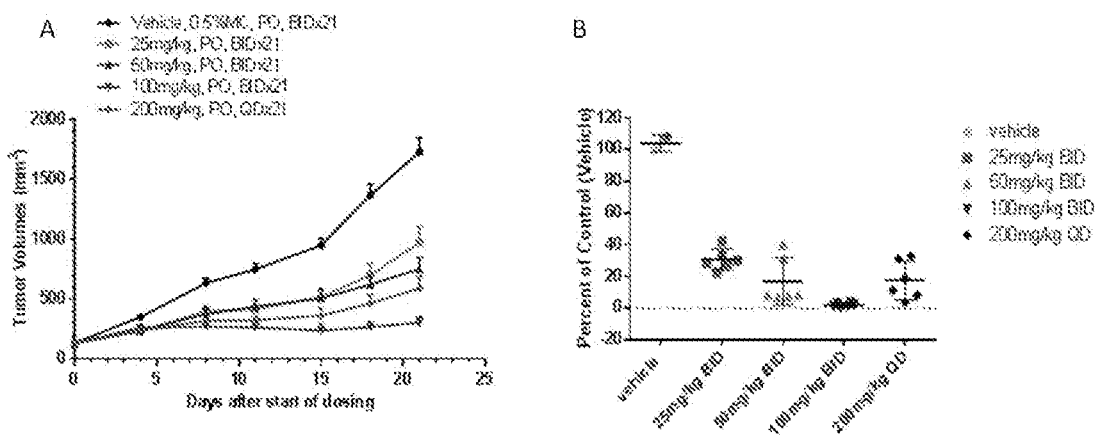
FIG. 44: Compound C efficacy and PD in a Z138 xenograft model. A. Compound C 21-day efficacy study in Z138 xenograft models. B. Quantified SDMA western data from tumors harvested at the end of the efficacy study (3 hours post last dose).

To test whether the efficacy observed in in vitro growth/death assays in lymphoma cell line models translates to an in vivo setting, Compound C efficacy studies were performed in xenograft models of mantle cell lymphoma (sensitive Z138 and Maver-1 cell lines). First, the therapeutic effects of Compound C treatment on tumor growth were tested in a 21-day efficacy study in a Z-138 MCL xenograft model. Tumors in all the Compound C dose groups showed significant differences in weight and volume compared to vehicle samples ranging from a minimum of 40% TGI at the lowest dose group (25 mg/kg BID) to as high as >90% in the top 100 mg/kg BID dose group (no body weight loss was observed in all groups in all efficacy studies presented, FIG. 44, panel A). PD analysis of tumors using the SDMA western showed that all dose groups had greater than 70% reduction of the methyl mark ranging as high as >98% in the top dose groups (FIG. 44, panel B).

Figure 45:
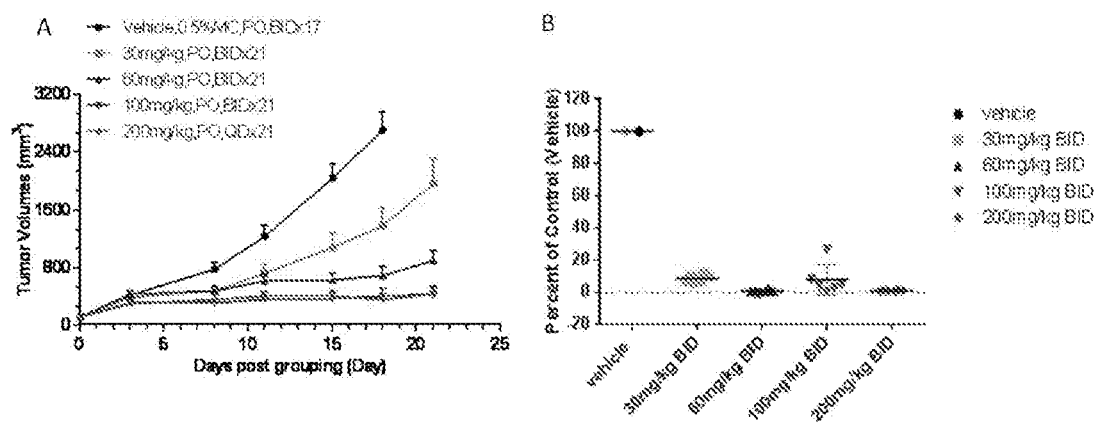
FIG. 45: Compound C efficacy and PD in a Maver-1 xenograft model. A. Compound C 21-day efficacy study in Maver-1 xenograft models. B. Quantified SDMA western data from tumors harvested at the end of the efficacy study (3 hours post last dose).

Next, efficacy of Compound C was assessed in a Maver-1 MCL xenograft model (FIG. 45). Tumors in all the Compound C dose groups measured on day 18 showed significant differences in volume compared to vehicle samples ranging from a minimum of 50% TGI at the lowest dose group to as high as >90% in the top dose groups. PD analysis of tumors using SDMA showed that all dose groups had 80-95% reduction of the methyl mark.

These data demonstrate that Compound C treatment results in significant tumor growth inhibition (close to 100% TGI) in xenograft models of mantle cell lymphoma. It appears that almost complete inhibition of the SDMA signal (>90%) is required for maximal TGI (>90%), suggesting that in order to obtain significant efficacy in tumors, PRMT5 activity needs to be inhibited>90%.

Lymphoma Biology Summary

The strongest mechanistic link currently described between PRMT5 and cancer is in MCL. PRMT5 is frequently overexpressed in MCL and is highly expressed in the nuclear compartment where it increases levels of histone methylation and silences a subset of tumor suppressor genes. Importantly, cyclin D1, the oncogene that is translocated in the vast majority of MCL patients, associates with PRMT5 and through a cdk4-dependent mechanism increases PRMT5 activity. PRMT5 mediates the suppression of key genes that negatively regulate DNA replication allowing for cyclin D1-dependent neoplastic growth. PRMT5 knockdown inhibits cyclin D1-dependent cell transformation causing death of tumor cells. These data highlight the important role of PRMT5 in MCL and suggest that PRMT5 inhibition could be used as a therapeutic strategy in MCL.

Compound C inhibits growth and induces death in MCL cell lines, which are amongst the most sensitive cell lines tested to date (in a 6-day growth/death assay). In a panel of MCL lines tested, 3 cell lines had $gIC_{50}$<10 nM, 2 lines exhibited $gIC_{50}$≤100 nM and 1 cell line had $gIC_{50}$>1 µM. Compound C effect on the downstream targets of PRMT5 and cyclin D1 is currently being investigated to evaluate whether it contributes to the anti-growth and proapoptotic response.

SDMA antibody Methylscan™ was used to evaluate PRMT5 substrates in MCL lines. The vast majority of SDMA containing proteins were factors that are involved in cellular splicing and RNA processing (SmB, Lsm4, hnRNPH1 and others), transcription (FUBP1) and translation highlighting the role of PRMT5 as an important regulator of cellular RNA homeostasis. The SDMA antibody was further used to evaluate PRMT5 inhibition in a panel of MCL lines where SDMA $IC_{50}$ values were similar in sensitive and resistant models, suggesting that SDMA is not a marker of response but rather a marker of PRMT5 inhibition.

Compound C treatment induced splicing changes in a subset of RNAs, in particular, an MDM4 isoform switch was observed in MCL and DLBCL lines, suggesting that PRMT5 inhibition activates the p53 pathway through the regulation of MDM4 splicing. Knockdown/rescue experiments will be used to further evaluate the role of the MDM4/p53 pathway in PRMT5 inhibitor induced cellular responses.

MDM4 isoform expression and p53 mutation are potential predictive biomarkers of response to PRMT5 inhibition in MCL. In a MCL cell line panel, the two wild-type p53 lines, Z138 and JVM-2, were the most sensitive lines (the lowest $gIC_{50}$ values and the only two MCL lines that exhibit cytotoxicity in a 6-day growth/death assay).

In recent years, the clinical exploration of ibrutinib drastically changed the approach to MCL treatment. In vitro data indicate that PRMT5 inhibitors could be used in an ibrutinib resistant MCL patient population and that the combination of PRMT5 inhibitors with ibrutinib could be explored in both ibrutinib refractory and sensitive settings.

In vivo studies demonstrate that Compound C treatment results in significant tumor growth inhibition (close to 100% TGI) in xenograft models of mantle cell lymphoma. It appears that in order to obtain maximal efficacy in tumors (TGI>90%), almost complete inhibition of PRMT5 activity (>90%) is required.

Breast Cancer Biology

The cell line screening data demonstrate that breast cancer cell lines are sensitive to PRMT5 inhibition and exhibit nearly complete growth inhibition in a 2D 6-day growth/death assay (low $Y_{min}$–T0, FIGS. 32-34). Additionally, the data from the colony formation assay in a panel of patient-derived (PDX) tumor models suggested that breast tumors are amongst the most sensitive tumors in the panel (based on the Compound E rel. $IC_{50}$ values, FIG. 35). Thus, breast cancer cell lines were assessed in several growth/death and mechanistic studies to assess the role and the therapeutic potential of PRMT5 inhibition in breast cancer.

Figure 46:
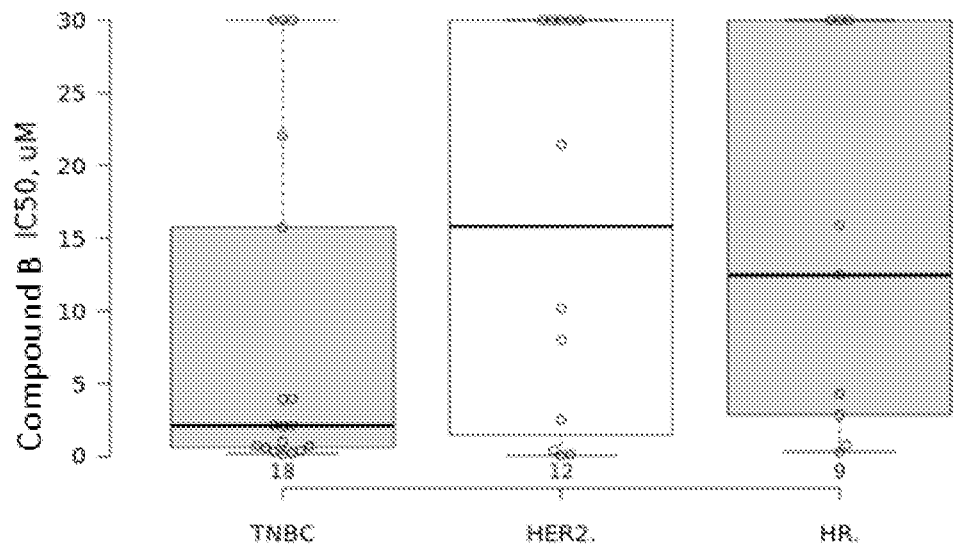
FIG. 46: Compound B growth $IC_{50}$ values in a panel of breast cancer cell lines from a 7-day growth 2D assay (TNBC-triple negative breast cancer, HER2-Her2 positive, HR-hormone receptor positive).

In order to understand PRMT5 inhibitor activity across different breast tumor subtypes, a panel of breast cancer cell lines was profiled in a 7-day growth assay using a PRMT5 tool compound (FIG. 46). PRMT5 inhibition attenuates cell growth with low $IC_{50}$ values across the various subtypes of breast cancer cell lines tested. The median $IC_{50}$ value was the lowest in TNBC (triple negative breast cancer) cell lines compared to the HER2 or hormone receptor (HR) positive lines.

Figure 47:
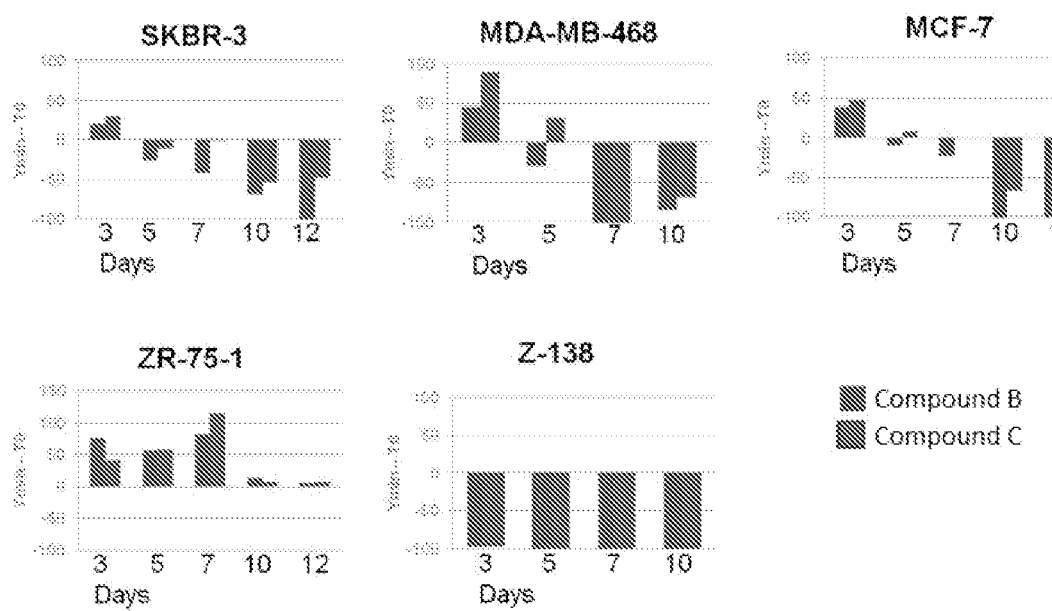
FIG. 47: $Y_{min}$-T0 values from 10-12 day growth/death assay in breast and MCL cell lines using the PRMT5 candidate, Compound C, and the PRMT5 tool molecule, Compound B.

In a 6-day growth/death assay, the majority of breast cancer cell lines exhibited cytostatic effect. To evaluate whether pro-longed exposure to Compound C will affect the cytostatic vs. cytotoxic nature of the response, PRMT5 inhibitors were evaluated in a longer-term growth/death assay (FIG. 47). In SKBR3, MDA-MB-468 and MCF-7 cells, treatment with Compound C (as well as tool molecule Compound B) led to a cytotoxic response upon prolonged exposure to compound (7-10 days). In ZR-75-1 cells, the PRMT5 inhibitors triggered a cytostatic response at all time points (days 3-12), while Z-138 (MCL, included as a control) cells exhibited profound overall net cell death at all time points (days 3-10) of the assay. These data suggest that PRMT5 inhibition leads to a net cell death (cytotoxic response) upon longer exposures (>5 days) in a subset of breast cancer cell lines.

Figure 48:
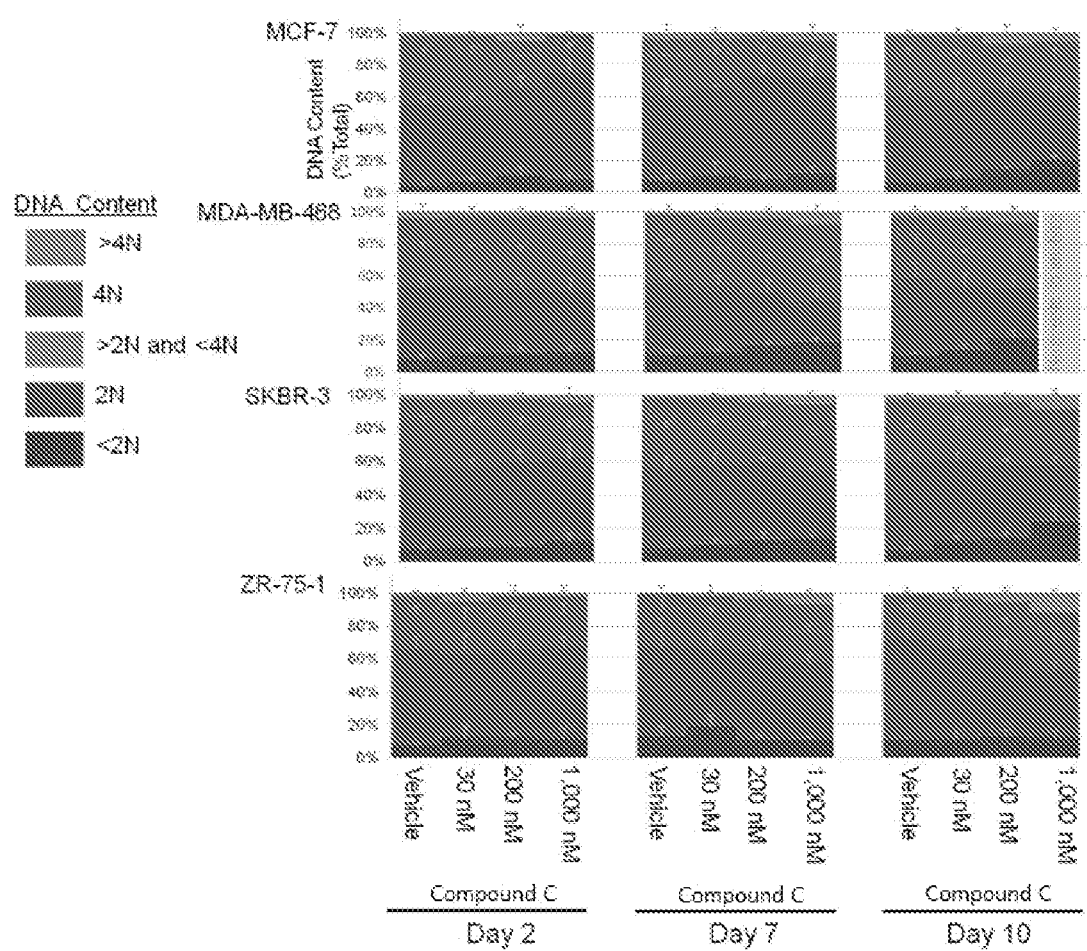
FIG. 48: Propidium iodide FACS analysis of breast cancer lines treated with 30, 200 and 1000 nM Compound C for various periods of time (day 2, 7 and 10, biological n=2, error bars represent standard deviation).

To test whether Compound C effects on cell growth were associated with changes in cell cycle distribution, the effects of Compound C on the cell cycle were evaluated using propidium iodide FACS (fluorescence activated cell sorting) analysis (FIG. 48). Overall, the FACS results are consistent with the long-term proliferation data, demonstrating that in 3 out of 4 breast cancer lines, long-term Compound C treatment resulted in the induction of cell death (increase in <2N) after 7-10 days of treatment. In MCF-7 cells (p53 wild-type), Compound C treatment led to the accumulation of cells in G1 phase (2N) and the loss of cells from S phase of the cell cycle (>2N and <4N) on day 2, with subsequent cell death as evidenced by the accumulation of cells in sub-G1 phase (<2N) on day 10. In ZR-75-1 cells (p53 wild-type), Compound C had minor effects on cell cycle distribution where there was a decrease in G1 (2N) and an increase in >4N cell fractions on days 7 and 10. MDA-MB-468 and SKBR-3 cell lines responded similarly to Compound C treatment with a decrease in G1 (2N) phase (day 7 or day 10), an increase in G2/M (4N) and >4N DNA content, which coincided with the accumulation of cells in subG1 (<2N), indicative of cell death. These data suggest that PRMT5 inhibition impacts the distribution of cells in the cell cycle and that the phenotypic outcome depends on the cellular context.

Figure 49:
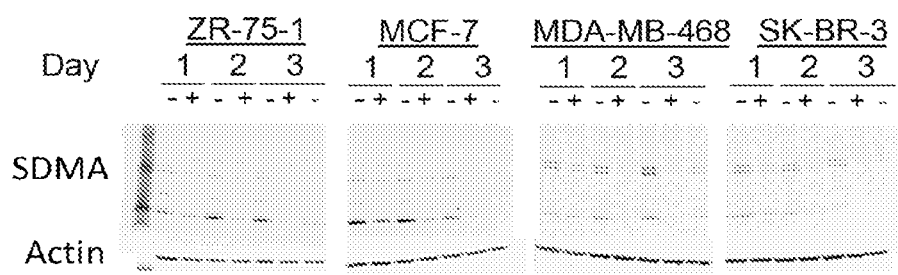
FIG. 49: Time course of SDMA inhibition following 1 µM Compound B treatment in a panel 10 of breast cancer cell lines. Cells were treated with DMSO or 1 µM Compound B for the indicated periods of time and cellular lysates were analyzed by western blot with SDMA and actin antibodies. The last lane on each blot is % of DMSO control.

In order to evaluate whether PRMT5 activity was equally inhibited in sensitive and resistant breast cancer lines, the levels of SDMA were measured in cells following PRMT5 inhibitor treatment (FIG. 49). Overall, the timing of the SDMA decrease was similar for all cell lines tested (sensitive and resistant). The maximal inhibition of SDMA was observed on day 3. The SDMA $IC_{50}$ in MDA-MB-468 cells was 5.4 nM, similar to the SDMA $IC_{50}$ in Z138 cells. These data indicate that SDMA is a marker of PRMT5 catalytic activity and is not predictive of antiproliferative response to PRMT5 inhibition. SDMA $IC_{50}$ values are being further evaluated in a panel of breast cancer lines.

Efficacy in In Vivo Breast Cancer Models

Figure 50:
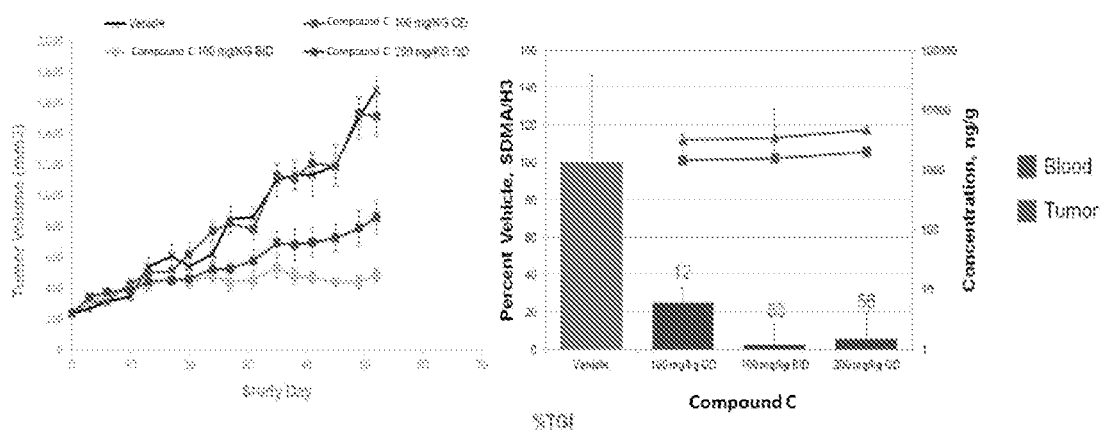
FIG. 50: Compound C efficacy (left) and PK/PD (right) in a MDA-MB-468 xenograft model.

Next, the efficacy of PRMT5 inhibition was evaluated in in vivo models of breast cancer. First, MDA-MB-468, a triple negative breast cancer xenograft model, was treated with 100 mg/kg (QD and BID) and 200 mg/kg (QD) of Compound C (FIG. 50). Maximal tumor growth inhibition (TGI=83%) was observed in the 100 mg/kg BID treated group, where SDMA inhibition was greater than 90%, while in the 100 mg/kg QD treated animals, Compound C treatment was not efficacious and SDMA inhibition was less than 80%. This data suggests that the SDMA levels need to be nearly completely inhibited (>90%) in order to see significant TGI in in vivo breast cancer xenograft models.

Breast Cancer Summary
- In breast cancer, high PRMT5 expression and high PDCD4 (programmed cell death 4) levels predict overall poor survival.
- Breast cancer cell lines and breast cancer patient-derived models were amongst the most sensitive models tested in a 2D growth/death and colony formation assays.
- Compound C treatment resulted in complete growth inhibition in a 6-day growth/death assay and pro-longed exposure to PRMT5 inhibitor induced cell death in 3 out of 4 cell lines tested.
- In a 7-day proliferation assay, TNBC cell lines were more sensitive to PRMT5 inhibition than Her2 and hormone receptor positive lines.
- SDMA levels were decreased in sensitive and resistant breast cancer lines treated with PRMT5 inhibitor, suggesting that SDMA is not a marker of response but rather a marker of PRMT5 activity.
- In a MDA-MB-468 xenograft model, Compound C treatment resulted in tumor growth inhibition (TGI=83%) in the 100 mg/kg BID treated group, where SDMA inhibition was greater than 90%, while in the 100 mg/kg QD treated animals, Compound C treatment was not efficacious and SDMA inhibition was less than 80%. This data suggests that SDMA levels need to be nearly completely inhibited (>90%) in order to see significant TGI in in vivo breast cancer xenograft models.
- Overall, these data suggest PRMT5 inhibition as a potential therapeutic strategy in breast cancer, in particular TNBC subtype.

Glioblastoma (GBM) Biology

PRMT5 protein is frequently overexpressed in glioblastoma tumors and high PRMT5 levels strongly correlate with both grade (grade IV) and poor survival in GBM patients (Yan F, et al. Cancer Res. 2014 Mar. 15; 74(6):1752-65). PRMT5 knockdown attenuates the growth and survival of GBM cell lines and significantly improves survival in an orthotopic Gli36 xenograft model (Yan F, et al. Cancer Res. 2014 Mar. 15; 74(6):1752-65). PRMT5 also plays an important role in normal mouse brain development through the regulation of growth and differentiation of neural progenitor cells (Bezzi M, et al. Genes Dev. 2013 Sep. 1; 27(17):1903-16).

Figure 51:
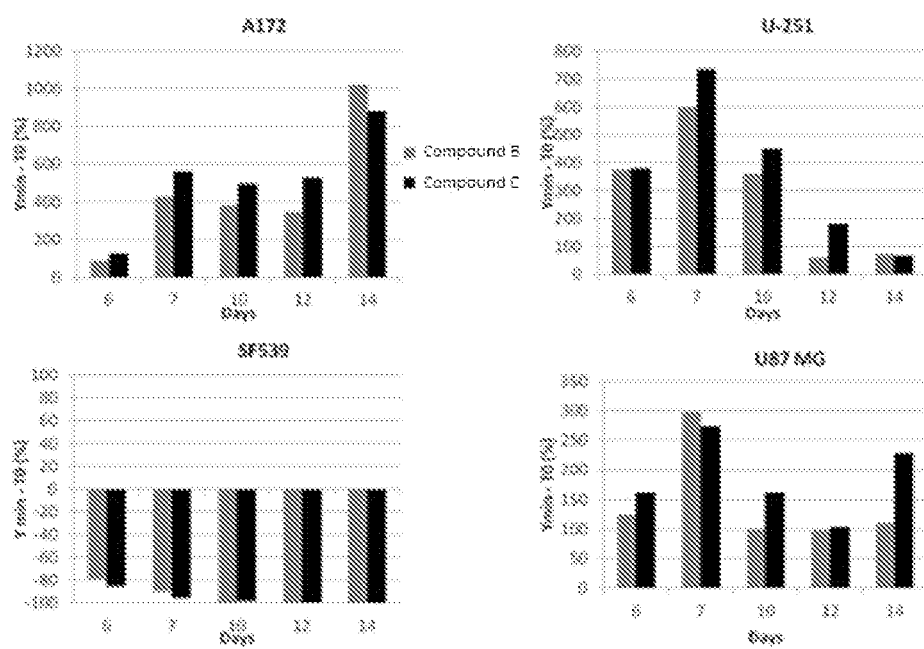
FIG. 51: 14 day growth/death CTG assay in GBM cell lines using the PRMT5 candidate, Compound C, and a PRMT5 tool molecule Compound B ($Y_{min}$-T0).

Glioblastoma cell line models were amongst the most sensitive tumor types in a soft agar colony formation assay (FIG. 35). In 2D, 6-day growth/death CTG assay, GBM cell lines had $gIC_{50}$ values in the 40-22000 nM range where the response was largely cytostatic, with the exception of the SF539 cell line (FIGS. 32 and 33). To understand the effects of PRMT5 inhibition on cell growth and survival upon longer exposure to a PRMT5 inhibitor, Compound C activity was tested in a 2D, 14-day growth/death CTG assay (FIG. 51). Overall, the nature of the cytostatic/cytotoxic response did not change upon longer exposure to the compound and the only cell line that underwent apoptosis in response to PRMT5 inhibition was SF539.

Figure 52:
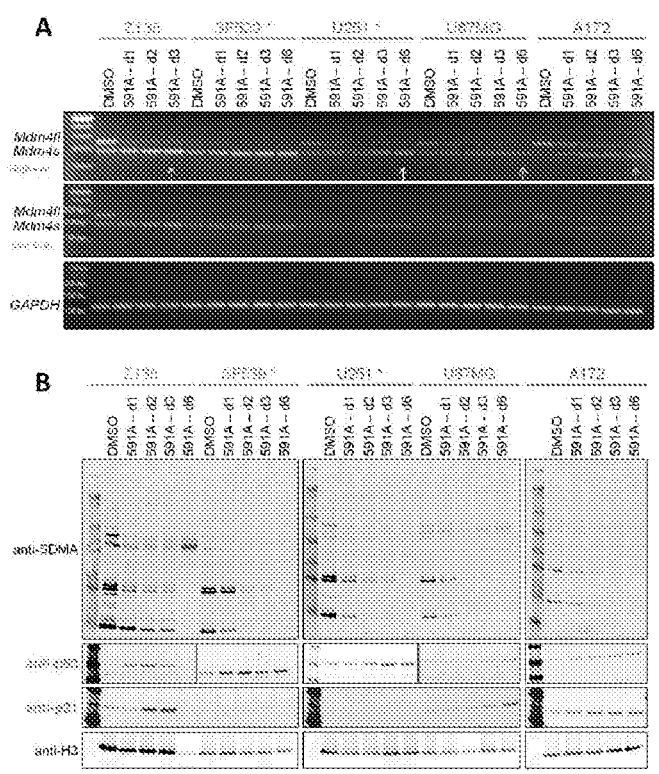
FIG. 52: Compound B (1 µM) decreases SDMA levels (B), induces alternative splicing of MDM4 (A), and activates p53 (B) in GBM and lymphoma cell lines.

Next, effects on cellular methylation and the p53 pathway were evaluated in GBM cells treated with a PRMT5 inhibitor by measuring SDMA, p53 and p21 protein levels and MDM4 splicing (FIG. 52). PRMT5 inhibition resulted in the reduction of the SDMA signal in all cell lines tested (FIG. 52, panel B), irrespective of their sensitivity to PRMT5 inhibition. Alternative MDM4 splicing was detected in all cell lines but SF539 which are p53 mutant and have low basal expression of the long MDM4 isoform (FIG. 52, panel A). p53 levels increased in all cell lines, while the induction of p21 protein was observed only in cell lines that have wild-type p53 (Z138 (MCL), U87-MG and A172 (GBM)). These data suggest that PRMT5 inhibitors can activate the p53 pathway in GBM models, potentially through the inactivation of MDM4 activity, similar to the effects observed in lymphoma models. Importantly, GBM cell line sensitivity did not correlate with p53 mutational status, suggesting that additional mechanisms contribute to the growth inhibitory phenotypes induced by PRMT5 inhibition. Interestingly, PRMT5 inhibition resulted in a cytostatic response in wild-type p53 GBM cell lines. The role of p53 in the response of GBM cell lines to PRMT5 inhibition will be further tested in future studies. Additionally, the effects of PRMT5 inhibition on cell cycle and neural differentiation in GBM models are being explored.

Glioblastoma Summary
- PRMT5 protein is frequently overexpressed in glioblastoma tumors and high PRMT5 levels strongly correlate with high grade (grade IV) and poor survival in GBM patients.
- Glioblastoma cell line models were amongst the most sensitive tumor types in a soft agar colony formation assay.
- In 2D, 6- and 14-day growth/death CTG assays, GBM response to PRMT5 inhibition was largely cytostatic (3 out of 4 lines, 1 cell line had a cytotoxic response).
- PRMT5 inhibition resulted in the reduction of the SDMA signal in all cell lines tested irrespective of their sensitivity to PRMT5 inhibition.

Additional Sensitive Tumor Types

Cell line and patient-derived model screening data suggest that PRMT5 inhibitors attenuate cell growth and survival in a broad range of tumor types (FIGS. 32-35).

Overall Biology Summary
- Compound C inhibits symmetric arginine dimethylation on a variety of cellular proteins including spliceosome components, histones, transcription factors, and kinases. Therefore, PRMT5 inhibitors impact RNA homeostasis through a multitude of mechanisms including changes in transcription, splicing, and mRNA translation.
- PRMT5 inhibition leads to gene expression and splicing changes ultimately resulting in the induction of p53. Compound C induces an isoform switch in the p53 ubiquitin ligase MDM4, stabilizes p53 protein, and induces p53 target gene expression signaling in mantle cell and diffuse large B-cell lymphoma as well as breast and glioma cancer cell lines (the only tumor types tested so far).
- Compound C inhibits proliferation in a broad range of solid and heme tumor cell lines and induces cell death in a subset of mantle cell and diffuse large B-cell lymphoma, breast, bladder, and glioma cell lines. The most potent growth inhibition was observed in mantle cell and diffuse large B-cell lymphoma cell lines. Compound C efficacy was tested in xenograft models of mantle cell lymphoma and breast cancer, where it significantly inhibited tumor growth. These data provide strong rationale for the use of Compound C as a therapeutic strategy in mantle cell lymphoma, diffuse large B-cell lymphoma, breast and brain cancer.

Example 3

Combinations

Figure 53:
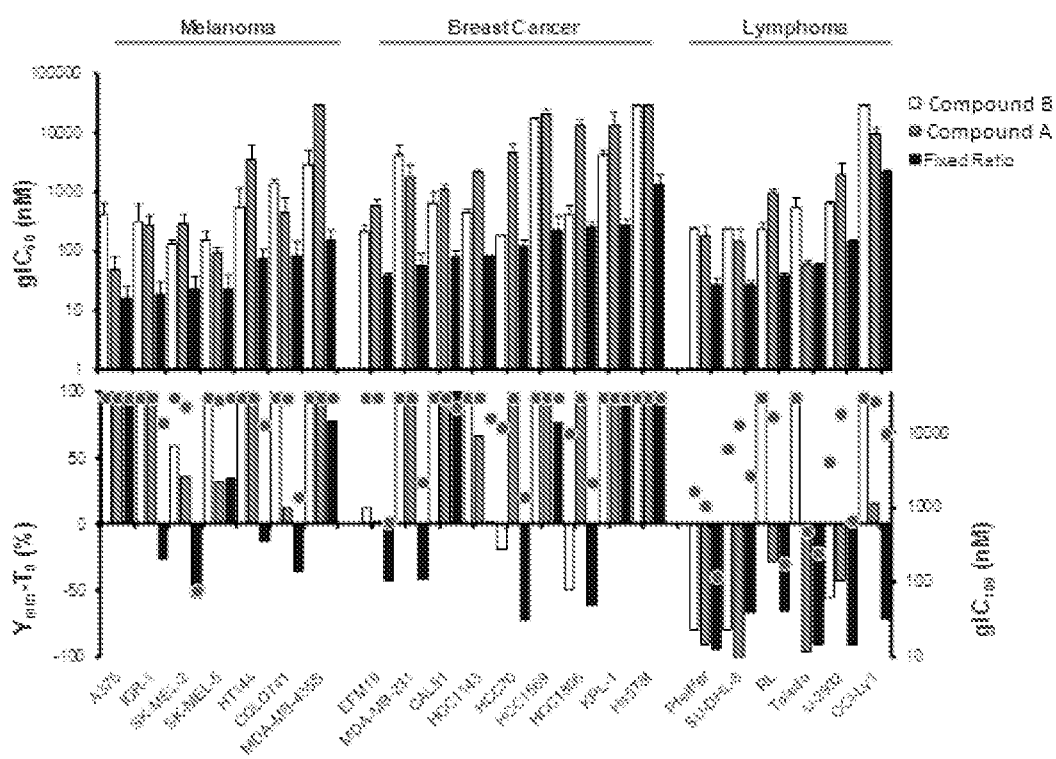
FIG. 53: Compound A and Compound B combinations in lymphoma, breast, and melanoma cancer cell lines. $gIC_{50}$, $gIC_{100}$, $Y_{min}$-$T_0$ from 6-day proliferation assays using Compound A, Compound B (PRMT5 inhibitor), or a fixed-ratio (1:1) combination of both compounds.

Two rational approaches were undertaken to investigate potential combinations with Compound A. First, the combined effects of inhibiting two distinct classes of arginine methyltransferases were explored using Compound A combined with an inhibitor of PRMT5, the major Type II PRMT inhibitor (Compound B). In these studies, melanoma, breast cancer, and lymphoma cell lines were treated with Compound A and Compound B single agent or in combination using a fixed 1:1 ratio of each inhibitor over a 20-point titration. Cell Titer Glo was used to measure growth inhibition as previously described. This combination resulted in ≥5-fold more potent $gIC_{50}$ in 15/22 cell lines relative to either single agent, with a ≥10-fold increase in 6 cell lines. In 15 cell lines showing cytostatic responses to both single agents, 7 had negative $Y_{min}$–$T_0$ with the combination, indicating a shift to cytotoxicity (FIG. 53, Table 8). Out of the 6 lymphoma cell lines tested, where 5 undergo cytotoxicity to either or both single agents, the combination treatment resulted in a ≥5 fold shift in $gIC_{100}$ in 3 lines These data indicate that a profound combination effect on inhibition of growth can be achieved through the simultaneous inhibition of Type I and the predominant Type II PRMT.

Compound C (a PRMT5 clinical candidate) is currently in Phase 1 clinical development; therefore evaluation of this combination will be possible if warranted. Additional preclinical testing of this combination will be performed using mouse xenograft models. Finally, this combination activity does not appear to be restricted to a specific tumor type suggesting it may offer an opportunity to expand into indications beyond which either Compound C or Compound A have potent single agent efficacy. Studies to investigate this hypothesis are underway.

TABLE 8

Fold shifts in potency with Compound A and Compound B combinations. Fold shifts are shown relative to the most potent single agent for each cell line.

| | | Fold Shift | |
|---|---|---|---|
| | | $gIC_{50}$ | $gIC_{100}$ |
| Melanoma | A375 | 3 | 1 |
| | IGR-1 | 15 | 2 |
| | SK-MEL-2* | 6 | 293 |
| | SK-MEL-5 | 4 | 1 |
| | HT144* | 7 | 2 |
| | COLO741* | 5 | 21 |
| | MDA-MB-435S* | 19 | 1 |
| Breast | EFM19* | 6 | 46 |
| | MDA-MB-231* | 32 | 13 |
| | CAL51* | 8 | 1 |
| | HCC1143 | 5 | 2 |
| | HCC70 | 2 | 8 |
| | HCC1569 | 80 | 1 |
| | HCC1806 | 2 | 5 |
| | KPL-1 | 15 | 1 |
| | Hs578t | 22 | 1 |

TABLE 8-continued

Fold shifts in potency with Compound A and Compound B combinations. Fold shifts are shown relative to the most potent single agent for each cell line.

| | | Fold Shift | |
|---|---|---|---|
| | | $gIC_{50}$ | $gIC_{100}$ |
| Lymphoma | Pfeiffer | 6 | 9 |
| | SU-DHL-8 | 5 | 2 |
| | RL | 6 | 96 |
| | Toledo | 1 | 2 |
| | U-2932 | 4 | 6 |
| | OCI-Ly1 * | 4 | 3 |

*Shift from cytostatic to cytotoxic
Bolded indicates >5 fold potency increase and italics indicates >10 fold.

Example 4

Combinations

The activity of combinations of Compound B with standard chemotherapeutic agents and Compound B with Compound D in triple negative breast cancer (TNBC) and bladder cell lines were determined.

FIG. 54 shows gIC50 and gIC100 fold changes relative to single agent (Compound B) treatment in various triple negative breast cancer (TNBC) cell lines treated with fixed ratio combinations of Compound B with Cisplatin, Carboplatin, Doxorubicin, a BET inhibitor, a MEK inhibitor, and Compound D. No synergy was observed with standard chemotherapeutic agents. In the Compound B and Compound D combination, 6 out of 7 TNBC cell lines exhibited a gIC50>3-fold change, with 4 out of the 6 exhibiting >5-fold change in gIC50.

FIG. 55 shows gIC50 and gIC100 fold changes relative to single agent (Compound B) treatment in various bladder cancer cell lines treated with fixed ratio combinations of Compound B with Cisplatin, Carboplatin, Doxorubicin, a BET inhibitor, a MEK inhibitor, and Compound D. In the Compound B and Compound D combination, 8 out of 10 bladder cancer cell lines exhibited a gIC50>3-fold change, with 3 out of the 8 exhibiting >5-fold change in gIC50.

Figures 56, 57:
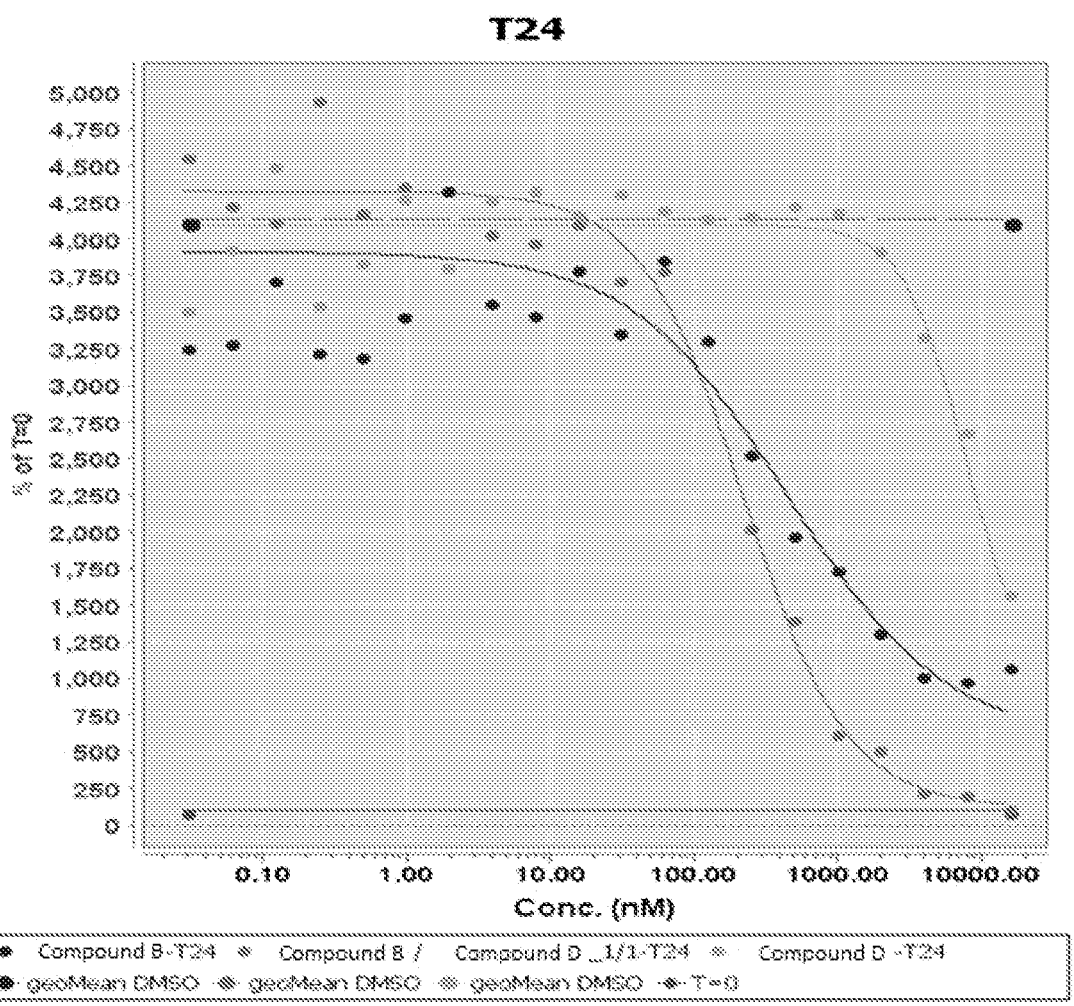
FIG. 56: Results of proliferation assays of a bladder cancer cell line (T24) treated with various concentrations of Compound B, Compound D, and a combination of Compound B and Compound D.
FIG. 57: Results of proliferation assays ($Y_{min}$-T0%) of bladder cancer cell lines SW-780 and T24 treated with Compound B and Compound D individually and in combination.

FIG. 56 shows results of proliferation assays of a bladder cancer cell line (T24) treated with various concentrations of Compound B, Compound D, and a combination of Compound B and Compound D.

FIG. 57 shows results of proliferation assays ($Y_{min}$–T0% change) of bladder cancer cell lines SW-780 and T24 treated with Compound B and Compound D individually and in combination.

FIG. 58 shows results of proliferation assays of 10 bladder cancer lines and 7 TNBC cell lines treated with a combination of Compound B and Compound D. The percentages of bladder cancer and TNBC cell lines that underwent cytotoxic (negative $Y_{min}$–T0%) and cytostatic responses are shown.

Results described in Example 4 were obtained using the following materials and methods.

Materials and Methods

Cell Lines

Cell lines were obtained from GSK BioCat, the American Type Culture Collection, or the Deutsche Sammlung von Mikroorganismen und Zellbulturen (DSMZ). All cell lines were maintained in the recommended cell culture media at 37° C. in 5% $CO_2$. In most cases this was RPMI-1640 medium supplemented with 10% fetal bovine serum (FBS; Sigma).

Standard 6-Day Growth-Death Assay

Cell proliferation assays were performed on a panel of cell lines according to the protocols referenced in AP12628v2 (384-well). Optimal cell seeding was determined for all cell lines by monitoring proliferation over a range of seeding densities in 384-well format and identifying the seeding density at which cells grew logarithmically through six days. 50 uL of cells were plated manually in 384-well plates at the optimal seeding density in culture media.

Cells were manually treated in duplicate with a 20-point, two-fold dilution series of Compound D and Compound B (≤15 μM top dose) and ≤0.15% DMSO. Plates were incubated for six days at the conditions described above. Cell growth was measured using an equal volume of CellTiter-Glo (Promega) and luminescence signal. A plate of untreated cells was read at the time of compound addition to determine the T=0 value representing the starting number of cells.

What is claimed is:

1. A combination of a Type I protein arginine methyltransferase (Type I PRMT) inhibitor and a Type II protein arginine methyltransferase (Type II PRMT) inhibitor; wherein the Type I PRMT inhibitor is a compound of Formula (I):

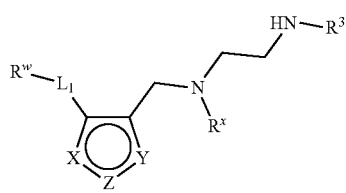

or a pharmaceutically acceptable salt thereof,
wherein
X is N, Z is $NR^4$, and Y is $CR^5$; or
X is $NR^4$, Z is N, and Y is $CR^5$; or
X is $CR^5$, Z is $NR^4$, and Y is N; or
X is $CR^5$, Z is N, and Y is $NR^4$;
$R^x$ is optionally substituted $C_{1-4}$ alkyl or optionally substituted $C_{3-4}$ cycloalkyl;
$L_1$ is a bond, —O—, —N($R^B$)—, —S—, —C(O)—, —C(O)O—, —C(O)S—, —C(O)N($R^B$)—, —C(O)N($R^B$)N($R^B$)—, —OC(O)—, —OC(O)N($R^B$)—, —$NR^B$C(O)—, —$NR^B$C(O)N($R^B$)—, —$NR^B$C(O)N($R^B$)N($R^B$)—, —$NR^B$C(O)O—, —SC(O)—, —C(=$NR^B$)—, —C(=$NNR^B$)—, —C(=$NOR^A$)—, —C(=$NR^B$)N($R^B$)—, —$NR^B$C(=$NR^B$)—, —C(S)—, —C(S)N($R^B$)—, —$NR^B$C(S)—, —S(O)—, —OS(O)$_2$—, —S(O)$_2$O—, —SO$_2$—, —N($R^B$)SO$_2$—, —SO$_2$N($R^B$)—, or an optionally substituted $C_{1-6}$ saturated or unsaturated hydrocarbon chain, wherein one or more methylene units of the hydrocarbon chain is optionally and independently replaced with —O—, —N($R^B$)—, —S—, —C(O)—, —C(O)O—, —C(O)S—, —C(O)N($R^B$)—, —C(O)N($R^B$)N($R^B$)—, —OC(O)—, —OC(O)N($R^B$)—, —$NR^B$C(O)—, —$NR^B$C(O)N($R^B$)—, —$NR^B$C(O)N($R^B$)N($R^B$)—, —$NR^B$C(O)O—, —SC(O)—, —C(=$NR^B$)—, —C(=$NNR^B$)—, —C(=$NOR^A$)—, —C(=$NR^B$)N($R^B$)—, —$NR^B$C(=$NR^B$)—, —C(S)—, —C(S)N($R^B$)—, —$NR^B$C(S)—, —S(O)—, —OS(O)$_2$—, —S(O)$_2$O—, —SO$_2$—, —N($R^B$)SO$_2$—, or —SO$_2$N($R^B$)—;
each $R^A$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;
each $R^B$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or an $R^B$ and $R^W$ on the same nitrogen atom may be taken together with the intervening nitrogen to form an optionally substituted heterocyclic ring;
$R^W$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; provided that when $L_1$ is a bond, $R^W$ is not hydrogen, optionally substituted aryl, or optionally substituted heteroaryl;
$R^3$ is hydrogen, $C_{1-4}$ alkyl, or $C_{3-4}$ cycloalkyl;
$R^4$ is hydrogen, optionally substituted $C_{1-6}$ alkyl, optionally substituted $C_{2-6}$ alkenyl, optionally substituted $C_{2-6}$ alkynyl, optionally substituted $C_{3-7}$ cycloalkyl, optionally substituted 4- to 7-membered heterocyclyl; or optionally substituted $C_{1-4}$ alkyl-Cy;
Cy is optionally substituted $C_{3-7}$ cycloalkyl, optionally substituted 4- to 7-membered heterocyclyl, optionally substituted aryl, or optionally substituted heteroaryl; and
$R^5$ is hydrogen, halo, —CN, optionally substituted $C_{1-4}$ alkyl, or optionally substituted $C_{3-4}$ cycloalkyl;
and wherein the Type II PRMT inhibitor is a compound of Formula (III):

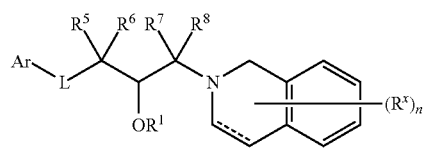

or a pharmaceutically acceptable salt thereof,
wherein
〰〰〰 represents a single or double bond;
$R^1$ is hydrogen, $R^z$, or —C(O)$R^z$, wherein $R^z$ is optionally substituted $C_{1-6}$ alkyl;
L is —N(R)C(O)—, —C(O)N(R)—, —N(R)C(O)N(R)—, —N(R)C(O)O—, or —OC(O)N(R)—;
each R is independently hydrogen or optionally substituted $C_{1-6}$ aliphatic;
Ar is a monocyclic or bicyclic aromatic ring having 0-4 heteroatoms independently selected from nitrogen, oxygen, and sulfur, wherein Ar is substituted with 0, 1, 2, 3, 4, or 5 Ry groups, as valency permits;
each $R^y$ is independently selected from the group consisting of halo, —CN, —NO$_2$, optionally substituted aliphatic, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_1$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NRBC(=NR$^B$)R$^B$, —C(=S)R$^A$, —C(=S)N(R$^B$)$_2$, —NR$^B$C(=S)R$^A$, —S(O)R$^A$, —OS(O)$_2$ R$^A$, —SO$_2$R$^A$, —NR$^B$SO$_2$R$^A$, or —SO$_2$N(R$^B$)$_2$;

each R$^A$ is independently selected from the group consisting of hydrogen, optionally substituted aliphatic, optionally substituted carbocyclyl, optionally substituted heterocyclyl, optionally substituted aryl, and optionally substituted heteroaryl;

each R$^B$ is independently selected from the group consisting of hydrogen, optionally substituted aliphatic, optionally substituted carbocyclyl, optionally substituted heterocyclyl, optionally substituted aryl, and optionally substituted heteroaryl, or two R$^B$ groups are taken together with their intervening atoms to form an optionally substituted heterocyclic ring;

R$^5$, R$^6$, le, and R$^8$ are independently hydrogen, halo, or optionally substituted aliphatic;

each R$^X$ is independently selected from the group consisting of halo, —CN, optionally substituted aliphatic, —OR', and —N(R")$_2$;

R' is hydrogen or optionally substituted aliphatic;

each R" is independently hydrogen or optionally substituted aliphatic, or two R" are taken together with their intervening atoms to form a heterocyclic ring; and n is 0, 1, 2, 3, 4, 5, 6, 7, 8, 9, or 10, as valency permits.

2. The combination of claim 1, wherein the Type I PRMT inhibitor is Compound A:

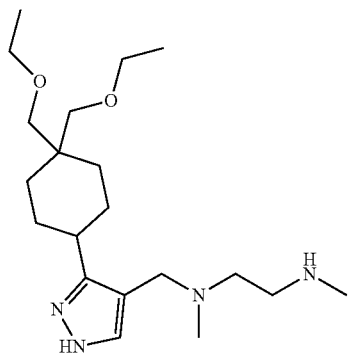

(A)

or a pharmaceutically acceptable salt thereof.

3. The combination of claim 1, wherein the Type II PRMT inhibitor is Compound C:

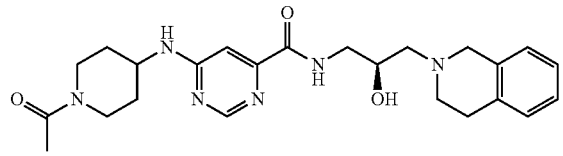

(C)

or a pharmaceutically acceptable salt thereof.

4. A pharmaceutical composition comprising a therapeutically effective amount of a Type I protein arginine methyltransferase 1 (PRMT1) inhibitor, and a therapeutically effective amount of a Type II protein arginine methyltransferase (Type II PRMT) inhibitor; wherein the Type I PRIVIT inhibitor is a compound of Formula (I):

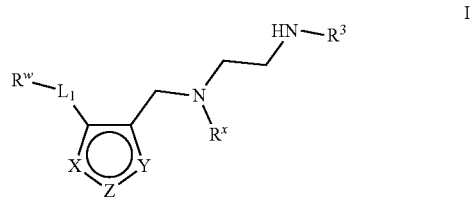

I or a pharmaceutically acceptable salt thereof,
wherein
X is N, Z is NR$^4$, and Y is CR$^5$; or
X is NR$^4$, Z is N, and Y is CR$^5$; or
X is CR$^5$, Z is NR$^4$, and Y is N; or
X is CR$^5$, Z is N, and Y is NR$^4$;

R$^x$ is optionally substituted C$_{1-4}$ alkyl or optionally substituted C$_{3-4}$ cycloalkyl;

L$_1$ is a bond, —O—, —N(R$^B$)—, —C(O)—, —C(O)O—, —C(O)S—, —C(O)N(R$^B$)—, —C(O)N(R$^B$)N(R$^B$)—, —OC(O)—, —OC(O)N(R$^B$)—, —NR$^B$C(O)—, —NR$^B$C(O)N(R$^B$)—, —NR$^B$C(O)N(R$^B$)N(R$^B$)—, —NR$^B$C(O)O—, —SC(O)—, —C(=NR$^B$)—, —C(=NNR$^B$)—, —C(=NOR$^A$)—, —C(=NR$^B$)N(R$^B$)—, —NR$^B$C(=NR$^B$)—, —C(S)—, —C(S)N(R$^B$)—, —NR$^B$C(S)—, —S(O)—, —OS(O)$_2$—, —S(O)$_2$O—, —SO$_2$—, —N(R$^B$)SO$_2$—, —SO$_2$N(R$^B$)—, or an optionally substituted C$_{1-6}$ saturated or unsaturated hydrocarbon chain, wherein one or more methylene units of the hydrocarbon chain is optionally and independently replaced with —O—, —N(R$^B$)—, —N(R$^B$)—, —C(O)—, —C(O)O—, —C(O)S—, —C(O)N(R$^B$)—, —C(O)N(R$^B$)N(R$^B$)—, —OC(O)—, —OC(O)N(R$^B$)—, —NR$^B$C(O)—, —NR$^B$C(O)N(R$^B$)—, —NR$^B$C(O)N(R$^B$)N(R$^B$)—, —NR$^B$C(O)O—, —SC(O)—, —C(=NR$^B$)—, —C(=NNR$^B$)—, —C(=NOR$^A$)—, —C(=NR$^B$)N(R$^B$)—, —NR$^B$C(=NR$^B$)—, —C(S)—, —C(S)N(R$^B$)—, —NR$^B$C(S)—, —S(O)—, —OS(O)$_2$—, —S(O)$_2$O—, —SO$_2$—, —N(R$^B$)SO$_2$—, or —SO$_2$N(R$^B$)—;

each R$^A$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

each R$^B$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or an R$^B$ and R$^W$ on the same nitrogen atom may be taken together with the intervening nitrogen to form an optionally substituted heterocyclic ring;

R$^W$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; provided that when L₁ is a bond, $R^W$ is not hydrogen, optionally substituted aryl, or optionally substituted heteroaryl;

$R^3$ is hydrogen, $C_{1-4}$ alkyl, or $C_{3-4}$ cycloalkyl;

$R^4$ is hydrogen, optionally substituted $C_{1-6}$ alkyl, optionally substituted $C_{2-6}$ alkenyl, optionally substituted $C_{2-6}$ alkynyl, optionally substituted $C_{3-7}$ cycloalkyl, optionally substituted 4- to 7-membered heterocyclyl; or optionally substituted $C_{1-4}$ alkyl-Cy;

Cy is optionally substituted $C_{3-7}$ cycloalkyl, optionally substituted 4- to 7-membered heterocyclyl, optionally substituted aryl, or optionally substituted heteroaryl; and $R^5$ is hydrogen, halo, —CN, optionally substituted $C_{1-4}$ alkyl, or optionally substituted $C_{3-4}$ cycloalkyl and wherein the Type II PRMT inhibitor is a compound of Formula (III):

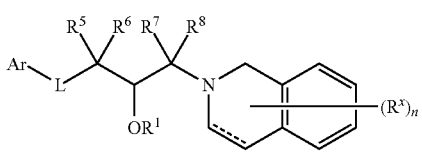

or a pharmaceutically acceptable salt thereof,
wherein

═════ represents a single or double bond;

$R^1$ is hydrogen, $R^2$, or —C(O)$R^z$, wherein $R^z$ is optionally substituted $C_{1-6}$ alkyl;

L is —N(R)C(O)—, —C(O)N(R)—, —N(R)C(O)N(R)—, —N(R)C(O)O—, or —OC(O)N(R)—;

each R is independently hydrogen or optionally substituted $C_{1-6}$ aliphatic;

Ar is a monocyclic or bicyclic aromatic ring having 0-4 heteroatoms independently selected from nitrogen, oxygen, and sulfur, wherein Ar is substituted with 0, 1, 2, 3, 4, or 5 Ry groups, as valency permits;

each $R^y$ is independently selected from the group consisting of halo, —CN, —NO₂, optionally substituted aliphatic, optionally substituted carbocyclyl, optionally substituted aryl, optionally substituted heterocyclyl, optionally substituted heteroaryl, —O$R^A$, —N($R^B$)₂, —S$R^A$, —C(═O)$R^A$, —C(O)O$R^A$, —C(O)S$R^A$, —C(O)N($R^B$)₂, —C(O)N($R^B$)N($R^B$)₂, —OC(O)$R^A$, —OC(O)N($R^B$)₂, —$NR^B$C(O)$R^A$, —$NR^B$C(O)N($R^B$)₂, —$NR^B$C(O)N($R^B$)N($R^B$)₂, —$NR^B$C(O)O$R^A$, —SC(O)$R^A$, —C(═$NR^B$)$R^A$, —C(═$NNR^B$)$R^A$, —C(═$NOR^A$)$R^A$, —C(═$NR^B$)N($R^B$)₂, —NRBC(═$NR^B$)$R^B$, —C(═S)$R^A$, —C(═S)N($R^B$)₂, —$NR^B$C(═S)$R^A$, —S(O)$R^A$, —OS(O)₂$R^A$, —SO₂$R^A$, —$NR^B$SO₂$R^A$, or —SO₂N($R^B$)₂;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring;

$R^5$, $R^6$, $R^7$, and $R^8$ are independently hydrogen, halo, or optionally substituted aliphatic;

each $R^X$ is independently selected from the group consisting of halo, —CN, optionally substituted aliphatic, —OR', and —N(R'')₂;

R' is hydrogen or optionally substituted aliphatic;

each R'' is independently hydrogen or optionally substituted aliphatic, or two R'' are taken together with their intervening atoms to form a heterocyclic ring; and n is 0, 1, 2, 3, 4, 5, 6, 7, 8, 9, or 10, as valency permits.

5. The pharmaceutical composition of claim 4 wherein the PRMT1 inhibitor is Compound A:

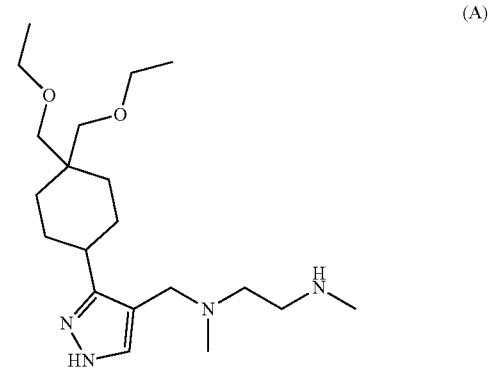 [SMILES: CCOCC1(COCC)CCC(c2n[nH]cc2CN(C)CCNC)CC1]

or a pharmaceutically acceptable salt thereof.

6. The pharmaceutical composition of claim 4, wherein the Type II PRMT inhibitor is Compound C:

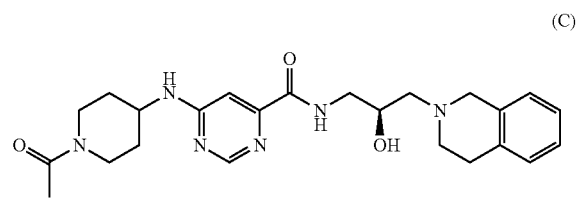 [SMILES: CC(=O)N1CCC(Nc2cc(C(=O)NC[C@H](O)CN3CCc4ccccc4C3)ncn2)CC1]

or a pharmaceutically acceptable salt thereof.

7. A pharmaceutical composition comprising a therapeutically effective amount of a Type I protein arginine methyltransferase (Type I PRMT) inhibitor and a therapeutically effective amount of a Type II protein arginine methyltransferase (Type II PRMT) inhibitor, wherein the PRMT1 inhibitor is Compound A:

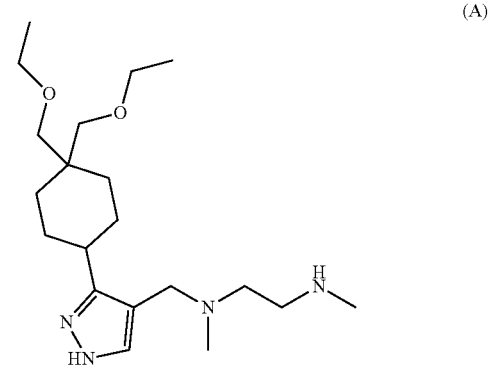 [SMILES: CCOCC1(COCC)CCC(c2n[nH]cc2CN(C)CCNC)CC1]

or a pharmaceutically acceptable salt thereof, and wherein the Type II PRMT inhibitor is Compound C:
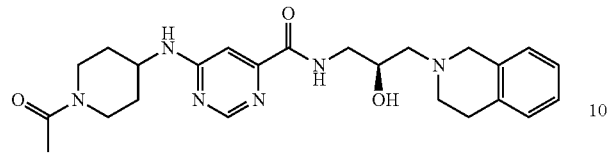
(C)
or a pharmaceutically acceptable salt thereof.
* * * * *